(12) United States Patent
Marugan et al.

(10) Patent No.: US 9,974,789 B2
(45) Date of Patent: *May 22, 2018

(54) SUBSTITUTED PYRAZOLOPYRIMIDINES AS GLUCOCEREBROSIDASE ACTIVATORS

(71) Applicant: The United States of America, as Represented by the Secretary, Department of Health and Human, Washington, DC (US)

(72) Inventors: Juan Jose Marugan, Gaithersburg, MD (US); Noel Southall, Potomac, MD (US); Ehud Goldin, Rockville, MD (US); Wei Zheng, Potomac, MD (US); Samarjit Patnaik, Gaithersburg, MD (US); Ellen Sidransky, Bethesda, MD (US); Omid Motabar, Darnestown, MD (US); Wendy Westbroek, Rockville, MD (US)

(73) Assignee: THE UNITED STATES OF AMERICA, AS REPRESENTED BY THE SECRETARY, DEPARTMENT OF HEALTH AND HUMAN SERVICES, Washington, DC (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/141,275

(22) Filed: Apr. 28, 2016

(65) Prior Publication Data

US 2016/0346284 A1    Dec. 1, 2016

Related U.S. Application Data

(63) Continuation of application No. 13/991,816, filed as application No. PCT/US2011/063928 on Dec. 8, 2011, now Pat. No. 9,353,117.

(60) Provisional application No. 61/420,946, filed on Dec. 8, 2010.

(51) Int. Cl.
| | | |
|---|---|---|
| *C07D 487/04* | (2006.01) | |
| *A61K 31/519* | (2006.01) | |
| *A61K 31/5377* | (2006.01) | |

(52) U.S. Cl.
CPC ........ *A61K 31/519* (2013.01); *A61K 31/5377* (2013.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 7,741,340 | B2 | 6/2010 | Fan et al. |
| 8,454,954 | B2 | 6/2013 | Schlossmacher et al. |
| 9,353,117 | B2 | 5/2016 | Marugan et al. |
| 2005/0130972 | A1 | 6/2005 | Fan et al. |
| 2005/0137223 | A1 | 6/2005 | Fan et al. |
| 2006/0008862 | A1 | 1/2006 | Mahuran et al. |
| 2006/0293345 | A1 | 12/2006 | Steeneck et al. |
| 2008/0287463 | A1 | 11/2008 | Herrmann et al. |
| 2009/0075960 | A1 | 3/2009 | Mahuran et al. |
| 2009/0163545 | A1 | 6/2009 | Goldfarb |
| 2010/0189708 | A1 | 7/2010 | Fan et al. |
| 2013/0177549 | A1 | 7/2013 | Schlossmacher et al. |
| 2014/0249145 | A1 | 9/2014 | Marugan et al. |

FOREIGN PATENT DOCUMENTS

| | | |
|---|---|---|
| JP | 2004277337 A | 10/2004 |
| WO | 2004037373 A2 | 5/2004 |
| WO | 2004089471 A2 | 10/2004 |
| WO | 2005046611 A2 | 5/2005 |
| WO | 2005046612 A2 | 5/2005 |
| WO | 2005123738 A1 | 6/2005 |
| WO | 2005113004 A2 | 12/2005 |
| WO | 2007008541 A2 | 1/2007 |
| WO | 2007020194 A1 | 2/2007 |
| WO | 2007046548 A1 | 4/2007 |
| WO | 2007048066 A2 | 4/2007 |

(Continued)

OTHER PUBLICATIONS

Sardi, S.P., et al. "Gaucher-related synucleinopathies: The examination of sporadic neurodegeneration from a rare (disease) angle." Progress in Neurobiology. (2015), vol. 125, pp. 47-62.*
National Organization for Rare Disorders. "Gaucher Disease." © 2008. Available from: < http://rarediseases.org/rare-diseases/gaucher-disease/ >.*
Chemical Abstract RN 1031931-42-6, Retreived from STN on Jul. 27, 2015.
Chemical Abstract RN 1197934-26-1, Retreived from STN on Jul. 27, 2015.
Chemical Abstract RN 309745-60-6, Retreived from STN on Jul. 27, 2015.

(Continued)

*Primary Examiner* — Noble E Jarrell
*Assistant Examiner* — John S Kenyon
(74) *Attorney, Agent, or Firm* — Cantor Colburn LLP

(57) ABSTRACT

Substituted pyrazolopyrimidines and dihydropyrazolopyrimidines and related compounds, their methods of manufacture, compositions containing these compounds, and methods of use of these compounds in treating lysosomal storage disorders such as Gaucher disease are described herein. The compounds are of general Formula (I)

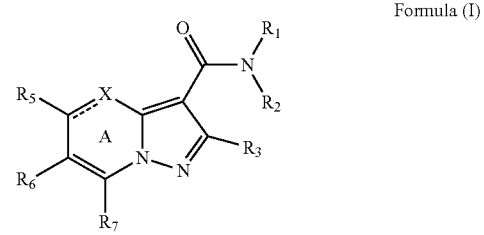

Formula (I)

in which variables $R_1$-$R_7$ and X are described in the application.

20 Claims, No Drawings

(56) References Cited

FOREIGN PATENT DOCUMENTS

| WO | 2007139860 A2 | 12/2007 |
| --- | --- | --- |
| WO | 2008045664 A2 | 4/2008 |
| WO | 2008054947 A2 | 5/2008 |
| WO | 2008063671 A2 | 5/2008 |
| WO | 2008154207 A1 | 6/2008 |
| WO | 2008128106 A1 | 10/2008 |
| WO | 2008134035 A1 | 11/2008 |
| WO | 2009038695 A1 | 3/2009 |
| WO | 2009049421 A1 | 4/2009 |
| WO | 2009049422 A1 | 4/2009 |
| WO | 2009152083 A1 | 12/2009 |
| WO | 2010003023 A2 | 1/2010 |
| WO | 2010086040 A1 | 8/2010 |
| WO | WO 2016/073895 A1 * | 5/2016 |

OTHER PUBLICATIONS

Chemical Abstract RN 492456-14-1, Retreived from STN on Jul. 27, 2015.
Chemical Abstract RN 515849-24-8, Retreived from STN on Jul. 27, 2015.
Chemical Abstract RN 664985-15-3. Retreived from STN on Jul. 27, 2015.
Chemical Abstract RN 725696-63-9, Retreived from STN on Jul. 27, 2015.
Chemical Abstract RN 797806-31-6, Retreived from STN on Jul. 27, 2015.
Chemical Abstract RN 797806-32-7, Retreived from STN on Jul. 27, 2015.
Chemical Abstract RN 836662-06-7; Retreived from STN on Jul. 27, 2015.
Chemical Abstract RN 933237-02-6, Retreived from STN on Jul. 27, 2015.
Chemical Abstract RN 951532-32-4, Retreived from STN on Jul. 27, 2015.
Zinc [online], Mar. 23, 2006 [retrieved on Sep. 14, 2015], ZINC ID: ZINC06359057, http://zinc.docking.org/substance/6359057.
Ahmed et al., "Synthesis of Some Pyrazolopyrimidines as Purina Analogues" Journal of Heterocyclic Chemistry, 44 (4), (2007), pp. 803-810.
Ammar et al., "Cyanoacetanilides Intermediates in Heterocyclic synthesis. Part 5: Preparation of Hitherto Unknown 5-aminopyrazole and Pyrazolo[1,5-a]pyrimidine Derivatives Containing Sulfamoyl Moiety" Journal of the Chinese Chemical Society (Taipei, Taiwan); 56; (2009); pp. 1064-1071.
Chebanov et al., "Cyclocondensation Reactions of 5-Aminopyrazoles, Pyruvic Acids and Aldehydes" Tetrahedron (2006), 63(5), (2007), pp. 1229-1242.
Dalinger et al., "Liquid-phase Synthesis of Combinatorial Libraries Based on 7-trifluoromethyl-substituted Pyrazolo [1,5-a]pyrimidine Scaffold" Journal of Combinatorial Chemistry, 7(2), (2005), pp. 236-245.
Grabowski, "Phenotype, Diagnosis, and treatment of Gaucher's Diseases" The Lancet, 2008, 372, 1263.
International Preliminary Report on Patentability and Written Opinion for International Application No. PCT/US2013/032253; International Filing Date: Mar. 15, 2013; Date of Issuance: Oct. 1, 2014; 7 Pages.
Marugan et al., "Evaluation of Quinazoline Analogues as Glucocerebrosidase Inhibitors with Chaperone Activity" J. Med. Chem., 54 (4); (2011); pp. 1033-1058.
Marugan et al., "New Non-Iminosugar Glucocerebrosidase Chaperone Series" MedChemComm, Med. Chem. Commun., 31(1), (2012), pp. 56-60.
Motabar et al., "A High Throughput Glucocerebrosidase Assay Using the Natural Substrate Glucosylceramide" Anal. Bloanal. Chem. 402, (2012), pp. 731-739.
Schulze et al. "Principles of Lysosomal Membrane Degradition Cellular Topology and biochemistry of Lysosomal Lipid Degradation" Blochimica et Biophysica Acta; 1793 (2009) pp. 674-683.
Aguilar et al. "Molecular Basis for Beta-Glucosidase Inhibition by Ring-Modified Calystegine Analogues" Nov. 3, 2008; 9(16): 2612.
Huppatz "Systemic Fungicides. The Synthesis of Pyrazolo[1,5-a]pyrimidine Analogues of Carboxin" Australian Journal of Chemistry; vol. 38, No. 1; Published Jan. 1, 1985; pp. 221-230.
International Search Report of the International Searching Authority for International Application No. PCT/US2011/063928; International Filing Date: Dec. 12, 2011.
Written Opinion of the International Searching Authority for International Application No. PCT/US2011/063928; International Filing Date: Dec. 8, 2011; 13 Pages.
Schulze et al. "Principles of Lysosomal Membrane Degradition Cellular Topology and biochemistry of Lysosomal Lipid Degradation" Biochimica et Biophysica Acta; 1793 (2009) pp. 674-683.
Toshihiko "Pyrazolo[1,5-a]pyrimidine Derivative" Japanese Patent Publication No. 2004277337; Date of Publication: Oct. 7, 2004. With English Abstract.
Tropak et al. "Identification of Pharmacological Chaperones for Gaucher Disease and Characterization of their Effects on Beta-Glucocerebrosidase by Hydrogen/Deuterium Exchange Mass Spectrometry." Nov. 3, 2008; 9(16): 2650.
Chemical Abstract; XP002670249; Oct. 7, 2004; 6 Pages.
Chemical Abstract; XP002670250; Jun. 25, 2009.
Chemical Abstract; XP002670251; Jun. 25, 2009; 2 Pages.
Chemical Abstract; XP002670252; Jun. 25, 2009; 2 Pages.
Chemical Abstract; XP002670253; Jun. 25, 2009; 2 Pages.
Chemical Abstract; XP002670254; Jun. 25, 2009; 2 Pages.
Chemical Abstract; XP002670255; Jun. 25, 2009; 3 Pages.
Chemical Abstract; XP 002670256; Jun. 25, 2009; 2 Pages.
Chemical Abstract; XP002670257; Jun. 25, 2009; 2 Pages.
Chemical Abstract; XP002670258; Jun. 25, 2009; 3 Pages.
Chemical Abstract; XP002670259; Jun. 25, 2009; 2 Pages.
Chemical Abstract; XP002670260; Jun. 25, 2009; 2 Pages.
Chemical Abstract; XP002670261; Jun. 25, 20109; 3 Pages.
Chemical Abstract; XP002670262; Jun. 25, 2009; 2 Pages.
Chemical Abstract; XP002670263; Jun. 25, 2009; 3 Pages.
Chemical Abstract; XP002670264; Jun. 25, 2009; 2 Pages.
Chemical Abstract XP002670265; Jun. 25, 2009; 2 Pages.
Chemical Abstract; XP002670266; Jun. 29, 2009; 2 Pages.
Chemical Abstract; XP002670267; Jun. 25, 2009; 2 Pages.
Chemical Abstract; XP002670268; 2005; 9 Pages.
Chemical Abstract; XP002670270; Apr. 29, 2007; 1 Page.
Zheng et al. "Three Classes of Glucocerebrosidase Inhibitors Identified by Quantitative High-Thorughput Screening are Chaperone Leads for Gaucher Disease" PNAS; vol. 104, No. 32 (Aug. 7, 2007), pp. 13192-13197.
Chemical Abstract RN 1031620-34-4, Retrived from STN Aug. 5, 2016.
Chemical Abstract RN 1031628-81-5, Retrived from STN Aug. 5, 2016.
Chemical Abstract RN 1089991-65-0, Retrived from STN Aug. 5, 2016.
Chemical Abstract RN 1311818-32-2, Retrived from STN Aug. 5, 2016.
Chemical Abstract RN 306475-46-8, Retrived from STN Aug. 5, 2016.
Chemical Abstract RN 309745-44-6, Retrived from STN Aug. 5, 2016.
Chemical Abstract RN 309745-50-4, Retrived from STN Aug. 5, 2016.
Chemical Abstract RN 361467-69-8, Retrived from STN Aug. 5, 2016.
Chemical Abstract RN 361467-73-4, Retrived from STN Aug. 5, 2016.
Chemical Abstract RN 361467-77-8, Retrived from STN Aug. 5, 2016.
Chemical Abstract RN 361467-97-2, Retrived from STN Aug. 5, 2016.
Chemical Abstract RN 361468-01-1, Retrived from STN Aug. 5, 2016.

(56) References Cited

OTHER PUBLICATIONS

Chemical Abstract RN 361468-10-2, Retrived from STN Aug. 5, 2016.
Chemical Abstract RN 361468-14-6, Retrived from STN Aug. 5, 2016.
Chemical Abstract RN 361468-18-0, Retrived from STN Aug. 5, 2016.
Chemical Abstract RN 361468-22-6, Retrived from STN Aug. 5, 2016.
Chemical Abstract RN 402940-14-1, Retrived from STN Aug. 5, 2016.
Chemical Abstract RN 725696-50-4. Retreived from STN on Sep. 20, 2016.
Chemical Abstract RN 725696-59-3, Retrived from STN Aug. 5, 2016.
Chemical Abstract RN 725696-72-0, Retrived from STN Aug. 5, 2016.
Chemical Abstract RN 832728-86-6, Retrived from STN Aug. 5, 2016.
Johnston et al., "Development and Implementation of a 384-Well Homogeneous Fluorescence Intensity High-Throughput Screening Assay to Identify Mitogen-Activated Protein Kinase Phosphatase-1 Dual-Specificty Protein Phosphatase Inhibitors", ASSAY and Drug.
Mitsos, "Isosteres in Medicinal Chemistry", (2006); Downloaded from: Http://www.scripps.edu/bran/images/grpmtgpdf/Mitsos_Feb_06.pdf.
Moss, "Glossary of Class Names of Organic Compounds and Reactive Intermediates Based on Structure", Pure & Applied Chemistry, 67, 8-9, pp. 1307-1375, 1995.
Patani et al., "Bioisosterism: A Rational Approach in Drug Design", Chem. Rev. 96; (1996); pp. 3147-3176.

\* cited by examiner

SUBSTITUTED PYRAZOLOPYRIMIDINES AS GLUCOCEREBROSIDASE ACTIVATORS

CROSS REFERENCE TO RELATED APPLICATION

This application is a continuation of application Ser. No. 13/991,816 filed on Aug. 28, 2013, which is the National Stage of International Application No. PCT/US2011/063928 filed on Dec. 8, 2011, which claims priority of U.S. provisional patent application no. 61/420,946 filed on Dec. 8, 2010, which is hereby incorporated by reference in its entirety.

STATEMENT OF GOVERNMENT SUPPORT

This invention was made in part with government support from the National Institutes of Health. The government has certain rights in this invention.

BACKGROUND

Gaucher disease is a rare disease affecting 1 in 40,000 babies born with a particular high frequency in the Ashkenazi Jews of eastern European descent (about 1 in 800 live births). It is caused by inherited genetic mutations in the GBA (glucosidase, beta acid) gene, which result in reduced activity of glucocerebrosidease (GCase or acid beta-glucocerebrosidase), an enzyme present in cellular organelles called lysosomes, responsible for the breakdown of a fatty material called glucocerebroside (or glucosyl ceramide). The accumulation of this lipid inside cells causes them to swell abnormally creating problems throughout the body. The disease has been categorized into three types: Neuronopathic (types 2, 3) and non-neuronopathic (type 1) with mild to severe symptoms that can appear at anytime from infancy to adulthood. Clinical manifestations include enlarged spleen/liver, anemia, lack of platelets, neurodegeneration, and bone disease with varying severity depending on the type of disease and time of diagnosis. The reduction in GCase activity has been attributed to the lack of protein in the lysosome. After production in the endoplasmic reticulum (ER) proteins that do not fold properly are degraded in the ER and not transported to the lysosome where they can hydrolyze glucocerebroside.

Existing treatment options for Gaucher disease include enzyme replacement (CEREZYME) or substrate reduction therapy (ZAVESCA) which cost between $100,000 to >$200,000 per year. The development of the iminosugar isofagomine (PLICERA) as a molecular chaperone was halted after Phase 2 clinical trials showed an increase in the amount of GCase in white blood cells but a lack in the reduction of visceral symptoms. Thus there is an unmet need for the development of novel chaperone therapy for Gaucher disease. The present disclosure fulfills this need and provides additional advantages set forth in the following disclosure.

SUMMARY

Described herein are substituted pyrazolopyrimidines and dihydropyrazolopyrimidines and related compounds, their methods of manufacture, compositions containing the described compounds, and methods of use of the described compounds. Thus in a first aspect, a compound of Formula (I) and the pharmaceutically acceptable salts of a compound of Formula (I) is provided

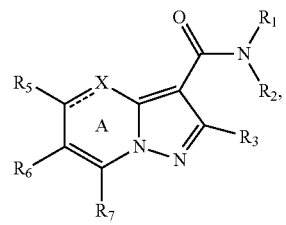

Formula (I)

wherein the ring

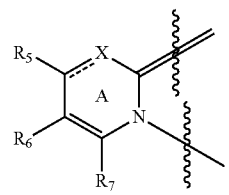

is a ring system of the formula (i)

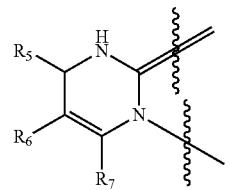

in which $R_5$ is an optionally substituted alkylidene group and $R_6$ and $R_7$ carry the definitions set forth below, or (ii)

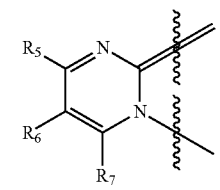

in which $R_5$, $R_6$, and $R_7$ carry the definitions set forth below.

$R_1$ is $C_1$-$C_6$alkyl, $C_2$-$C_6$alkenyl, $C_2$-$C_6$alkynyl, (mono- or bicyclic carbocycle)$C_0$-$C_4$alkyl or (mono- or bicyclic heterocycle) $C_0$-$C_4$alkyl, each of which $R_1$ is unsubstituted or substituted with one or more substituents independently chosen from halogen, hydroxyl, cyano, nitro, amino, —CHO, —COOH, $C_1$-$C_6$alkyl, $C_2$-$C_6$alkenyl, $C_2$-$C_6$alkynyl, $C_1$-$C_6$alkoxy, $C_2$-$C_6$alkanoyl, (mono- or di-$C_1$-$C_6$alkylamino)$C_0$-$C_4$alkyl, mono- or di-$C_1$-$C_6$alkylcarboxamide, $C_1$-$C_6$alkylester, $C_1$-$C_6$alkylthio, $C_1$-$C_6$alkylsulfonyl, $C_1$-$C_2$haloalkyl, and $C_1$-$C_2$haloalkoxy, and with 0 or 1 substituents chosen from Y—Z— where Z is a covalent bond, $C_1$-$C_4$alkylene, $C_2$-$C_4$alkenylene, $C_2$-$C_4$alkynylene, —S—, —O—, —NR—, —C(O)—, —NHC(O)—, or —C(O)NH—, where R is hydrogen or $C_1$-$C_4$alkyl, and Y is phenyl pyrimidinyl, 5- or 6-membered heterocycloalkyl, or pyridyl, each of which is unsubstituted or substituted with 1 to 3 substituents independently chosen from halogen, hydroxyl, cyano, nitro, amino, $C_1$-$C_4$alkyl, $C_1$-$C_4$alkoxy, mono- or di-$C_1$-$C_4$alkylamino, trifluoromethyl, difluoromethyl, trifluoromethoxy, and phenyl; and $R_2$ is hydrogen, $C_1$-$C_6$alkyl, $C_3$-$C_7$cycloalkyl, and (phenyl)$C_0$-$C_2$alkyl.

Or, $R_1$ and $R_2$ are joined to form a 5- to 7-membered heterocycloalkyl ring having 0 or 1 additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$alkyl, and $C_1$-$C_2$alkoxy.

$R_3$ is hydrogen or $C_1$-$C_2$alkyl.

$R_5$ is halogen, hydroxyl, amino, cyano, $C_1$-$C_4$alkyl, vinyl, cyclopropyl, cyclopropylidenyl, $C_1$-$C_4$alkoxy, difluoromethyl, trifluoromethyl, or phenyl.

$R_6$ is halogen, hydroxyl, $C_1$-$C_4$alkyl, or $C_1$-$C_4$alkoxy.

$R_7$ is halogen, hydroxyl, amino, cyano, $C_1$-$C_4$alkyl, $C_1$-$C_4$alkoxy, difluoromethyl, or trifluoromethyl, or $R_7$ is phenyl or a 5- to 7-membered heterocycloalkyl ring having 1 or 2 heteroatoms chosen from N, O, and S, each of which $R_7$ is directly attached via a covalent bond or attached via a $C_1$-$C_4$ alkyl, $C_1$-$C_4$alkoxy, or $C_1$-$C_4$alkylamino group, and each of which $R_7$ is unsubstituted or substituted with 1 to 3 substituents independently chosen from halogen, hydroxyl, $C_1$-$C_4$alkyl, $C_1$-$C_4$alkoxy, (mono- and di-$C_1$-$C_2$alkylamino)$C_0$-$C_4$alkyl, $C_1$-$C_2$haloalkyl, and $C_1$-$C_2$haloalkoxy; or $R_6$ and $R_7$ are taken together to form a 5- or 6-membered carbocyclic ring with no additional points of unsaturation, which ring is unsubstituted or substituted with 1 to 3 substituents independently chosen from $C_1$-$C_2$alkyl and $C_1$-$C_2$alkoxy.

In certain embodiments $R_1$ is not unsubstituted phenyl, dihydroindenyl, benzy[b][1,4]dioxolyl, benzo[d][1,3]dioxol-5-yl, cyclohexyl, pyridyl, or phenyl substituted with 1 or 2 substituents independently chosen from chloro, fluoro, $C_1$-$C_4$alkyl, $C_1$-$C_2$alkoxy, acetyl, and trifluoromethyl, when $R_6$ is hydrogen, $R_5$ and $R_7$ are both methyl, or when $R_6$ is hydrogen and one $R_5$ and $R_7$ is methyl and the other is phenyl. Also $R_1$ is not 1-(4-fluorobenzyl)-1H-pyrazol-4-yl when $R_6$ is hydrogen and one $R_5$ and $R_7$ is methyl and the other is phenyl.

In another aspect a pharmaceutical composition comprising a compound of Formula I, or salt thereof, together with a pharmaceutically acceptable carrier, is provided.

Also provided herein is a method of treating Gaucher disease in a patient or preventing or reducing the severity of the symptoms of Gaucher disease in a patient having a GBA gene mutation comprising providing an effective amount of a compound of Formula (I) or pharmaceutically acceptable salt thereof to the patient.

Yet another aspect provides a method of increasing the amount of beta glucocerebrosidase in the white blood cells of patient having a GBA gene mutation, comprising providing an effective amount of a compound of Formula (I) to the patient.

DETAILED DESCRIPTION

Described herein are substituted pyrazolopyrimidines and dihydropyrazolopyrimidines and related compounds useful as chaperones of glucocerebrosidase. Certain substituted pyrazolopyrimidines and dihydropyrazolopyrimidines and related compounds disclosed in this application are potent and selective activators of glucocerebrosidase. These compounds are useful in treating Gaucher disease and preventing the symptoms of Gaucher disease in persons who have a mutated GBA gene.

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene groups replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group.

A dash ("-") that is not between two letters or symbols is used to indicate a point of attachment for a substituent.

"Alkyl" includes both branched and straight chain saturated aliphatic hydrocarbon groups, having the specified number of carbon atoms. The term $C_1$-$C_2$alkyl means an alkyl group having from 1 to about 2 carbon atoms, e.g., methyl and ethyl, respectively Likewise "alkenyl" is a branched or straight chain unsaturated hydrocarbon group having the specified number of carbon atoms and at least one carbon-carbon double bond and alkynyl is a branched or straight chain unsaturated hydrocarbon group having the specified number of carbon atoms and at least one carbon-carbon triple bond.

"Alkylene" is a straight or branched saturated bivalent carbon chain having the indicated number of carbon atoms.

"Alkylester" is an alkyl group as defined above attached through an ester linkage. The ester linkage may be in either orientation, e.g., a group of the formula —O(C=O)alkyl or a group of the formula —(C=O)Oalkyl.

"Alkylester" is an alkyl group as defined above attached through an ester linkage. The ester linkage may be in either orientation, e.g., a group of the formula —O(C=O)alkyl or a group of the formula —(C=O)Oalkyl.

"Alkylester" is an alkyl group as defined above attached through an ester linkage. The ester linkage may be in either orientation, e.g., a group of the formula —O(C=O)alkyl or a group of the formula —(C=O)Oalkyl.

"Alkanoyl" is an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkylsulfonyl" is a group of the formula alkyl-($SO_2$)—, where the alkyl group is an alkyl group as defined above having the defined number of carbon atoms. An exemplary alkylsulfonyl group is methylsulfonyl.

"Alkylthio" indicates an alkyl group as defined above attached through a sulfur linkage, i.e. a group of the formula alkyl-S—. Examples include ethylthio and pentylthio.

"Alkoxy" means an alkyl group, as defined above, with the indicated number of carbon atoms attached via an oxygen bridge.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

A "mono- or bicyclic carbocycle" is a 3- to 8-membered saturated, partially unsaturated, or aromatic ring containing only carbon ring atoms or a 6 to 11 membered saturated, partially unsaturated, or aromatic bicyclic carbocyclic ring system containing only carbon ring atoms. Unless otherwise indicated, the carbocyclic group may be attached to its pendant group at any carbon atom that results in a stable structure. When indicated the carbocyclic rings described herein may be substituted on any available ring carbon if the resulting compound is stable. Carbocyclic groups include cycloalkyl groups, such as cyclopropyl and cyclohexyl; cycloalkenyl groups, such as cyclohexenyl, bridged cycloalkyl groups; and aryl groups, such as phenyl.

"Halo" or "halogen" means fluoro, chloro, bromo, or iodo.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Mono- or bicyclic-heterocycle" is a 5- to 8-membered saturated, partially unsaturated, or aromatic ring containing from 1 to about 4 heteroatoms chosen from N, O, and S, with remaining ring atoms being carbon, or a 7 to 11 membered bicyclic saturated, partially unsaturated, or aromatic heterocylic ring system, each containing at least 1 heteroatom in the multiple ring system chosen from N, O, and S and containing up to about 4 heteroatoms independently chosen from N, O, and S in each ring of the multiple ring system. Unless otherwise indicated, the heterocyclic ring may be attached to the group it substitutes at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

"Mono- and/or di-alkylamino" means secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino.

"Mono- or di-alkylcarboxamide" is a group of the formula —(C=O)Nalkyl$_1$alkyl$_2$, where the alkyl$_1$ and alkyl$_2$ groups are independently chosen alkyl groups as defined herein, attached through a carboxamide linkage. The carboxamide linkage may be in either orientation, e.g., —NH(C=O)— or —(C=O)NH—.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

"Pharmaceutical compositions" means compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any symptom of a beta-glucocerebrosidase mediated disorder, e.g., cause regression of the disorder, liver function, reduce anemia, increase platelet count, or decrease the rate of neurodegeneration or bone degeneration. In certain embodiments treatment of Gaucher disease may be commenced before the patient presents symptoms of the disease.

A "therapeutically effective amount" of a pharmaceutical composition means an amount effective, when administered to a patient, to provide a therapeutic benefit such as an amelioration of symptoms, e.g., an amount effective to decrease the symptoms of Gaucher disease.

A significant change is any detectable change that is statistically significant in a standard parametric test of statistical significance such as Student's T-test, where $p<0.05$.

Chemical Description

Compounds of formula I may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

Small molecules which activate the GCase enzyme are disclosed herein. The data suggests these small molecules may be acting as chaperones which help the misfolded enzyme to fold properly and be trafficked from the endoplasmic reticulum to the lysosome. Most small molecule chaperones described in literature are inhibitors of GCase and thus can potentially inhibit enzyme activity in the lysosome. The present chemical series is advantageous as the compounds do not inhibit, but rather activate GCase. The chemical class of pyrazolo[1,5-a]pyrimidine-3carboxamides is also structurally distinct from iminosugars, often described as chaperones in literature, and holds promise towards selectivity against other glycosidases.

In addition to compounds of Formula (I) shown above in the SUMMARY section, Compounds of II and III, which are subformulae of Formula I, and compounds in which the variables, e.g., $R_1$-$R_7$ carry the following definitions are also disclosed.

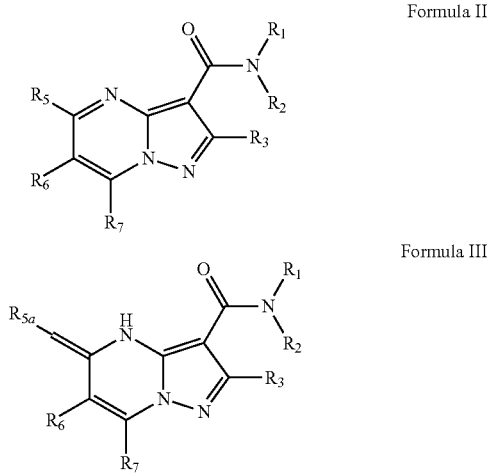

Formula II

Formula III

In Formula III, $R_{5a}$ is hydrogen, $C_1$-$C_4$alkyl, $C_3$-$C_7$cycloalkyl, or 4- to 7-membered carbon attached heterocycloalkyl, having 1 or 2 heteroatoms independently chosen from N, S, and O.

In certain embodiments of Formula III, $R_{5a}$ is hydrogen or cyclopropyl.

Included herein are compounds and salts for Formula I and II in which:

$R_2$ is hydrogen or methyl; and
$R_5$ is $C_1$-$C_4$alkyl, difluoromethyl, or phenyl;
$R_7$ is $C_1$-$C_4$alkyl, difluoromethyl, or phenyl; and
$R_5$ and $R_7$ are not both phenyl.

Further included herein are compounds and salts for Formula I and II in which:

$R_5$ and $R_7$ are both methyl; or
one of $R_5$ and $R_7$ is methyl and the other is phenyl; or
one of $R_5$ and $R_7$ is methyl and the other is difluoromethyl.

Included herein are compounds and salts of Formula I, II, and III in which:

$R_1$ is (phenyl)$C_0$-$C_4$alkyl, (pyridyl)$C_0$-$C_4$alkyl, (pyrimidinyl) $C_0$-$C_4$alkyl, ($C_3$-$C_7$cycloalkyl)$C_0$-$C_4$alkyl, (pyrazolyl)$C_0$-$C_2$alkyl, (pyrrolyl)$C_0$-$C_2$alkyl, (imidazolyl)$C_0$-$C_2$alkyl, (thienyl)$C_0$-$C_2$alkyl, (furanyl)$C_0$-$C_2$alkyl, (oxazolyl)$C_0$-$C_2$alkyl, (thiazolyl)$C_0$-$C_2$alkyl, pyrolidinyl, naphthyl, quinolinyl, isoquinolinyl, tetrahydronaphthyl, tetrahydroquinolinyl, tetrahydroisoquinolinyl, tetrahydrofuranyl, piperazinyl, morpholinyl, piperidinyl, thiomorpholinyl, dihydroindenyl, benzo[b][1,4]dioxinyl, or benzo[d][1,3]dioxolyl, each of which is unsubstituted or substituted with one or more substituents independently chosen from halogen, hydroxyl, cyano, nitro, amino, —CHO, —COOH, $C_1$-$C_6$alkyl, $C_1$-$C_6$alkoxy, $C_2$-$C_6$alkanoyl, mono- or di-$C_1$-$C_6$alkylamino, mono- or di-$C_1$-$C_6$alkylcarboxamide, $C_1$-$C_6$alkylester, $C_1$-$C_6$alkylthio, $C_1$-$C_6$alkylsulfonyl, $C_1$-$C_2$haloalkyl, and $C_1$-$C_2$haloalkoxy, and with 0 or 1 substituents chosen from Y—Z— where Z is a covalent bond, $C_1$-$C_4$alkylene, —S—, —O—, —NR—, —C(O)—, —NHC(O)—, or —C(O)NH—, where R is hydrogen or $C_1$-$C_4$alkyl, and Y is phenyl or pyridyl, each of which is unsubstituted or substituted with 1 to 3 substituents independently chosen from halogen, hydroxyl, cyano, nitro, amino, $C_1$-$C_4$alkyl, and $C_1$-$C_4$alkoxy.

Also included herein are compounds and salts of Formula I, II, and III in which:

$R_1$ and $R_2$ are joined to form a 5- to 7-membered heterocycloalkyl ring having 0 or additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$alkyl, and $C_1$-$C_2$alkoxy.

Further included herein are compounds and salts of Formula I, II, and III in which $R_1$ is (phenyl)$C_0$-$C_2$alkyl, substituted with at least one substituent chosen from cyano, trifluoromethyl, $CH_3C(O)NH$—, orn$R_1$ is cyclohexyl, substituted with at least one trifluoromethyl, $C_3$-$C_6$alkyl; or $R_1$ is dihydroindenyl, quinolinyl, or isoquinolinyl; each of which $R_1$ may be substituted with one or more substituents independently chosen from halogen, hydroxyl, cyano, nitro, amino, —CHO, —COOH, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, and $C_1$-$C_2$haloalkoxy.

Included herein are compounds and salts of Formula I, II, and III in which:

$R_2$ is hydrogen or methyl; and $R_7$ is $C_1$-$C_4$alkyl, difluoromethyl, or phenyl. In some embodiments it is preferred that $R_7$ is difluoromethyl.

Included herein are compounds and salts of Formula I, II, and III in which:

$R_2$ is hydrogen or methyl; and $R_7$ is methyl or difluoromethyl; and
$R_1$ is (phenyl)$C_0$-$C_2$alkyl, (pyridyl)$C_0$-$C_2$alkyl, (cyclohexyl)$C_0$-$C_2$alkyl, pyrazolyl, furanylnaphthyl, quinolinyl, isoquinolinyl, tetrahydronaphthyl, tetrahydroquinolinyl, tetrahydroisoquinolinyl tetrahydrofuranyl, morpholinyl, piperidinyl, piperazinyl, thiomorpholinyl, dihydroindenyl, benzo[b][1,4]dioxinyl, or benzo[d][1,3]dioxolyl, each of which is unsubstituted or substituted with one or more substituents independently chosen from halogen, hydroxyl, cyano, nitro, amino, —CHO, —COOH, $C_1$-$C_4$alkyl, $C_1$-$C_4$alkoxy, $C_2$-$C_4$alkanoyl, mono- or di-$C_1$-$C_4$alkylamino, mono- or di-$C_1$-$C_4$alkylcarboxamide, $C_1$-$C_4$alkylester, $C_1$-$C_2$alkylsulfonyl, trifluoromethyl, trifluoromethoxy, and difluoromethyl, and with 0 or 1 substituents chosen from Y—Z— where Z is a covalent bond, $C_1$-$C_4$alkylene, —S—, —O—, —NR—, —C(O)—, —NHC(O)—, or —C(O)NH—, where R is hydrogen or $C_1$-$C_4$alkyl, and Y is phenyl or pyridyl, each of which is unsubstituted or substituted with 1 to 3 substituents independently chosen from halogen, hydroxyl, $C_1$-$C_2$alkyl, and $C_1$-$C_2$alkoxy.

Compounds of Formula I have the following tautomeric formulas:

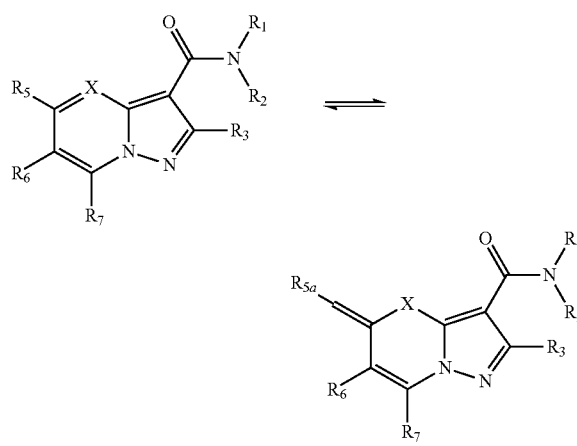

Pharmaceutical Preparations

The substituted pyrazolopyrimidines and dihydropyrazolopyrimidines disclosed herein can be administered as the neat chemical, but are specifically administered as a pharmaceutical composition, for example a pharmaceutical formulation comprising a substituted pyrazolopyrimidines or dihydropyrazolopyrimidine compound of Formula I or pharmaceutically acceptable salt thereof, together with at least one pharmaceutically acceptable carrier. The pharmaceutical composition can be is formulated as an injectable fluid, an aerosol, a cream, a gel, a tablet, a pill, a capsule, a syrup, or a transdermal patch.

The substituted pyrazolopyrimidines and dihydropyrazolopyrimidines may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorings, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active and/or inactive agents may be included in the pharmaceutical compositions, provided that such agents do not substantially interfere with the activity of the hydrazone and diacyl hydrazine compounds used in the pharmaceutical compositions. The optional active is an additional active agent that is not a compound or salt of Formula I.

The pharmaceutical compositions can be formulated for oral administration. These compositions contain between 0.1 and 99 weight % (wt. %) of a hydrazone or a diacyl hydrazine compound and usually at least about 5 wt. % of a hydrazone or a diacyl hydrazine compound. Some embodiments contain from about 25 wt. % to about 50 wt. % or from about 5 wt. % to about 75 wt. % of the hydrazone or diacyl hydrazine compound.

Treatment Methods

The compounds of Formula I or a salt thereof, as well as pharmaceutical compositions comprising the compounds, are useful for treating lysosomal storage diseases, including Gaucher disease. The compounds of Formula I or a salt thereof, as well as pharmaceutical compositions comprising the compounds, are also useful for preventing the occurrence of symptoms of a lysosomal storage disorder, such as Gaucher disease, in a patient having GBA gene mutation. The method of treating a lysosomal storage disease in a patient comprises providing to the patient an effective amount of a compound or salt of Formula I: In an embodiment the patient is a mammal, specifically a primate, more specifically a human. An effective amount of a pharmaceutical composition may be an amount sufficient to inhibit the progression of a disease or disorder; or cause a regression of a disease or disorder.

An effective amount of a compound or pharmaceutical composition described herein will also provide a sufficient concentration of a substituted pyrazolopyrimidines or dihydropyrazolopyrimidines compound when administered to a patient. A sufficient concentration is a concentration of the compound or salt of Formula I in the patient's body necessary to prevent or combat the disorder. Such an amount may be ascertained experimentally, for example by assaying blood concentration of the compound, or theoretically, by calculating bioavailability.

Methods of treatment include providing certain dosage amounts of a substituted pyrazolopyrimidine or dihydropyrazolopyrimidine compound or salt to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

In an embodiment, the invention provides a method of treating a lysosomal storage disorder in a patient identified as in need of such treatment, the method comprising providing to the patient an effective amount of a compound of Formula I. The compounds and salts of Formula I provided herein may be administered alone, or in combination with one or more other active agent.

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

EXAMPLES

The following Examples are offered by way of illustration and not by way of limitation. Unless otherwise specified, all reagents and solvent are of standard commercial grade and are used without further purification. Starting materials are available from commercial suppliers, such as Sigma-Aldrich (St. Louis, Mo.), or are synthesized using procedures that are known in the art.

Example 1

Synthetic Scheme for Preparing Substituted Pyrazolopyrimidines and Dihydropyrazolopyrimidines The synthetic sequence (Scheme 1) used to generate the substituted pyrazolopyrimidines and dihydropyrazolopyrimidines provided herein starts with the condensation of a 1,3-diketone 6 with ethyl 3-amino-1H-pyrazole-4-carboxylate 7 in acetic acid. Such reactions have been reported previously. See for example WO 2008/134035 and Huppatz, J. L. *Aust. J Chem.* 1985, 38, 221-230. Initial efforts to simplify the evaluation of the amide SAR centered on the use of acetylacetone as the diketone to eliminate the formation of regioisomers ($R_1$=$R_2$=$CH_3$). With unsymmetrical ketones a mixture of regioisomers (8, 9) forms which is typically separated by chromatography. Ester hydrolysis then provides an acid, which is coupled with amines or anilines to generate compounds (10, 11) for biological analysis.

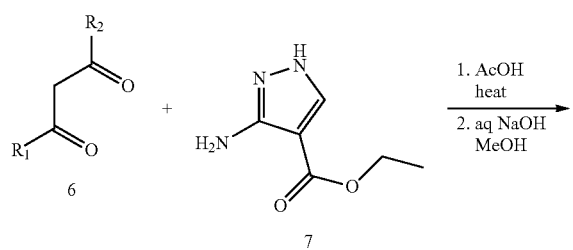

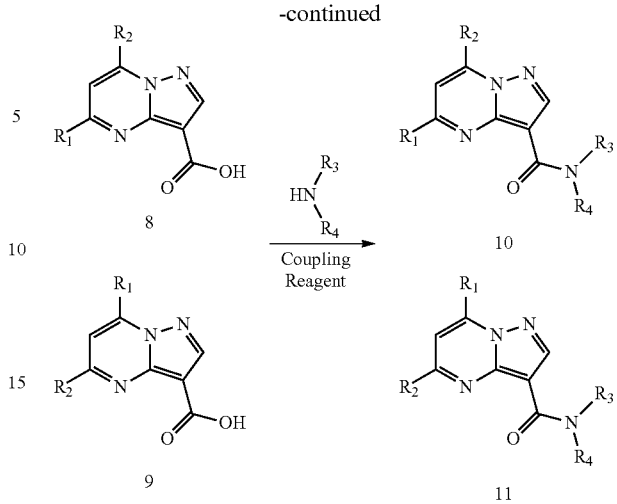

Example 2

Synthesis of N-(4-Ethynylphenyl)-5,7-dimethyl-pyrazolo[1,5-a]pyrimidine-3-carboxamide Step 1. Synthesis of 5,7-Dimethylpyrazolo[1,5-a]pyrimidine-3-carboxylic acid (12)

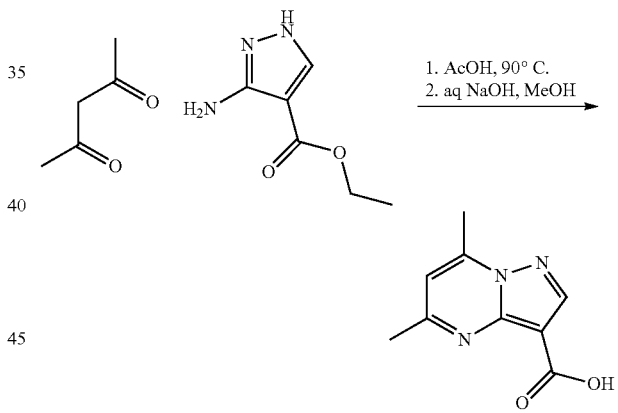

Pentane-2,4-dione (1.46 ml, 14.2 mmol), ethyl 3-amino-1H-pyrazole-4-carboxylate (2.00 g, 12.9 mmol) were heated in a sealed tube with acetic acid (10 ml) at 110° C. overnight. The reaction reached completion by LCMS (LC-MS: rt (min)=3.08). The acetic acid was removed by blowing air with the flask being heated to 75° C. The crude residue of ethyl 5,7-dimethylpyrazolo[1,5-a]pyrimidine-3-carboxylate (assumed to be 12.89 mmol) was suspended in MeOH (15 ml) and treated with 7.2 M sodium hydroxide (5.37 ml, 38.7 mmol). The mixture was heated to 80° C. (at this temperature the solid dissolved) and then stirred for 3 h. The reaction was cooled and the neutralized to pH 6-7. The slurry was filtered via a Büchner funnel under house vacuum, the solid residue was washed with water and then diethyl ether to obtain 5,7-dimethylpyrazolo[1,5-a]pyrimidine-3-carboxylic acid (1.4 g, 7.3 mmol, 57% yield). LC-MS: rt (min)=2.61. 1H NMR (400 MHz, DMSO-$d_6$) δ ppm 2.57 (s, 3 H), 2.71 (s, 3 H), 7.10 (s, 1 H), 8.50 (s, 1 H).

Step 2. Synthesis of N-(4-Ethynylphenyl)-5,7-dimethylpyrazolo[1,5-a]pyrimidine-3-carboxamide (13)

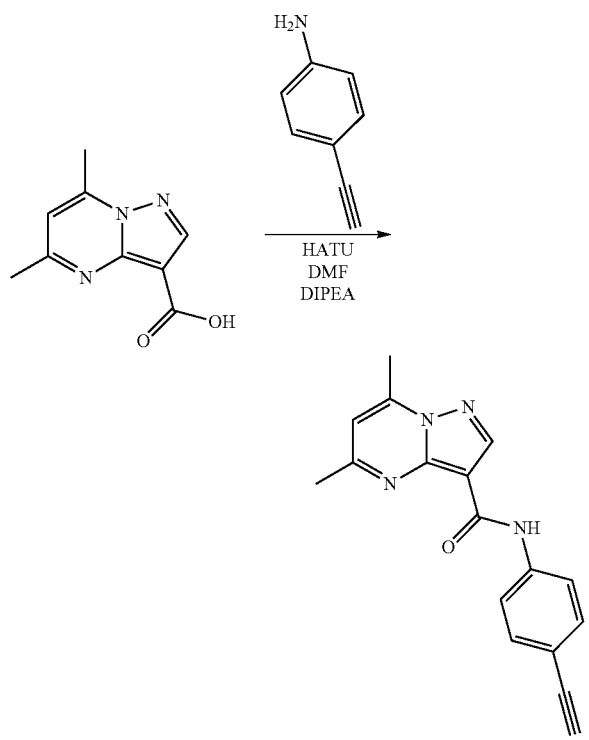

5,7-Dimethylpyrazolo[1,5-a]pyrimidine-3-carboxylic acid (722 mg, 3.78 mmol), 4-ethynylaniline (442 mg, 3.78 mmol), and HATU (1436 mg, 3.78 mmol) were taken up in DMF (10 ml) and then treated with diisopropylethylamine (1.979 ml, 11.33 mmol). The contents stirred at room temperature overnight. The product had precipitated from reaction mixture. The reaction was diluted with water, filtered through a Büchner funnel under house vacuum. The residue was washed with water (×2), then $CH_2Cl_2$, diethyl ether, and air dried to obtain N-(4-ethynylphenyl)-5,7-dimethylpyrazolo[1,5-a]pyrimidine-3-carboxamide (500 mg, 1.72 mmol, 46% yield). LC-MS: rt (min)=3.65. 1H NMR (400 MHz, DMSO-$d_6$) δ ppm 2.71 (s, 3 H), 2.77 (s, 3 H), 4.11 (s, 1 H), 7.21 (s, 1 H), 7.49 (d, J=8.6 Hz, 2 H), 7.77 (d, J=8.6 Hz, 2 H), 8.65 (s, 1 H), 10.31 (s, 1 H).

Example 3

Assay Protocol for Glucocerebrosidase Activity qHTS Assay for Inhibitors and Activators of N370S glucocerebrosidase as a Potential Chaperone Treatment of Gaucher Disease: Primary Screen Confirmation This is a fluorogenic enzyme assay with 4-methylumbelliferyl-beta-D-glucopyranoside as the substrate and N370S glucocerebrosidase from human spleen homogenate as the enzyme preparation. Upon the hydrolysis of this fluorogenic substrate, the resulting product, 4-methyllumbelliferone, can be excited at 365 nm and emits at 440 nm which can be detected by a standard fluorescence plate reader. Data were normalized to the controls for basal activity (without enzyme) and 100% activity (with enzyme). The AC50 values were determined from concentration-response data modeled with the standard Hill equation.

Human spleen homogenate is prepared as follows by homogenizing spleen with assay buffer containing 50 mM citric acid (titrated with potassium phosphate to pH 5.0), 100 mM potassium chloride, 10 mM sodium chloride, 1 mM magnesium chloride, 0.01% Tween-20. The protein concentration of the human spleen homogenate is approximated 1.35 ug/ul.

The assay is performed in 1536 well plates according to the following protocol. (1) 2 ul spleen homogenate (27 ug final) is added to each well. (2) 23 nL test compound in DMSO solution is added to each well. The final concentration of compound in the test well is 0.5 nM to 58 uM. (3) 2 ul of substrate (1 mM final) are added to each well. (4) Incubate assay plates at 37° C. for 40 min. (5) Add 2 ul stop solution (1M NaOH and 1M Glycine mixture, pH 10) to each well. (6) Detect the assay plate in a ViewLux plate reader (PerkinElmer) using 365 nm excitation with emission at 440 nm.

Example 4

Chaperone activity of N-(4-ethynylphenyl)-5,7-dimethylpyrazolo[1,5-a]pyrimidine-3-carboxamide (NGC00188758-01)

Chaperone activity of NGC00188758-1 (1 μM and 5 μM), isofagomine (1 μM), and a vehicle control were evaluated in a N370S patient derived fibroblast for chaperone activity. GCase was visualized with red stain (anti GCase R386 antibody), lysosome with green (LAMP), and nucleus with blue (DAPI). An overlay of all stains shows bright yellow color (due to overlap of red and green color) color indicating the presence of GCase in the lysosome. All laser settings were held constant across all of the fields imaged. Both isofagomine and NGC00188758-1 showed significantly increased GCase activity in the lysosome relative to vehicle control.

Example 5

Selectivity Assay: qHTS Assay for Inhibitors and Activators of N370S glucocerebrosidase as a Potential Chaperone Treatment of Gaucher Disease: Alpha-Glucosidase Counterscreen To characterize compound selectivity, selected hits from the primary screen were screened against purified alpha-glucosidase, a related sugar hydrolase. Alpha-glucosidase is responsible for hydrolysis of terminal, non-reducing 1,4-linked alpha-D-glucose residues with release of alpha-D-glucose. This is a fluorogenic enzyme assay using 4-methylumbelliferyl-alpha-D-pyranoside as the substrate and human alpha-glucosidase as the enzyme preparation. Upon the hydrolysis of this fluorogenic substrate, the resulting product, 1.4-methyllumbelliferone, can be excited at 365 nm and emits at 440 nm. Emission is detected by a standard fluorescence plate reader. Data were normalized to the controls for basal activity (without enzyme) and 100% activity (with enzyme). The AC50 values were determined from concentration-response data modeled with the standard Hill equation.

The assay is performed in 1536 well plates according to the following protocol. (1) Add 2 ul/well of human alpha-glucosidase enzyme (4 nM final) in assay buffer (50 mM citric acid (titrated with potassium phosphate to pH 5.0), 0.005% Tween-20, pH 5.0) to each well. (2) Add 23 nL compounds in DMSO solution. The final compound titration is 0.7 nM to 77 uM. (3) Add 1 ul of substrate (400 uM final). (4) Incubate at room temperature for 20 min. (5) Add 2 ul stop solution (1M NaOH and 1M Glycine mixture, pH 10) (6) Detect the assay plate in a ViewLux plate reader (PerkinElmer) with Ex=365 nm and Em=440 nm.

Example 6

Lysosomal Translocation Assay: Chaperone Activity in Gaucher Fibroblasts after Multi-day Incubation with Compound This assay quantitates translocated glucocerebrosidase protein in patient-derived fibroblasts following extended compound incubation. The fibroblasts tested in this experiment were homozygous for N370S glucocerebrosidase.

Primary dermal fibroblasts derived from skin biopsies from two previously described N370S/N370S Gaucher patients (Goker-Alpan et al, 2008) and a control were seeded in Lab-Tek 4 chamber slides (Fisher Scientific, Pittsburgh, Pa.). After compound treatment fibroblasts were fixed in 3% paraformaldehyde. The cells were permeabelized with 0.1% Triton-X for 10 min. and blocked in PBS containing 0.1% saponin, 100 µM glycine, 0.1% BSA and 2% donkey serum followed by incubation with mouse monoclonal anti-LAMP1 or LAMP-2 (1:100, Developmental Studies Hybridoma bank, University of Iowa, Iowa City, Iowa) and the rabbit polyclonal anti-GCase R386 antibody (1:500). The cells were washed and incubated with secondary donkey anti-mouse or anti-rabbit antibodies conjugated to ALEXA-488 or ALEXA-555, respectively (Invitrogen, Carlsbad, Calif.), washed again, and mounted in VectaShield with DAPI (Vector Laboratories, Burlingame, Calif.).

Cells were imaged with a Zeiss 510 META confocal laser-scanning microscope (Carl Zeiss, Microimaging Inc., Germany) using an Argon (458, 477, 488, 514 nm) 30 mW laser, a HeNe (543 nm) 1 mW laser, and a laser diode (405 nm). Low and high magnification images were acquired using a Plan-Apochromat 20×/0.75 objective and a Plan-Apochromat 100×/1.4 oil DIC objective, respectively. Images were taken with the same laser settings and all the images are collapsed z-stacks. Images suggested significant translocation of glucocerebrosidase protein to lysosomes in compound treated fibroblasts relative to untreated fibroblasts.

Example 8

Additional Compounds

The following compounds are prepared according to the procedures provided in Examples 1 and 2. Those of skill in the art will recognize that reagents and reaction conditions will need to be varied to achieve the listed compounds. Such variations will be readily apparent to those of skill in the art of organic chemical synthesis.

LCMS retention time data was obtained as follows:

Method 1. Column: Phenomenex Luna C18 (3 micron, 3×75 mm). Run time: 8 min. Gradient: 4% to 100% Acetonitrile in water over 7 min. Mobile phase: Acetonitrile (0.025% TFA), water (0.05% TFA). Flow rate: 1 mL/min. Temperature: 50° C. UV wavelength: 220 nm, 254 nm 2. Method 2: detection UV214, Gemini column, Solvent A is water, Solvent B is 90% acetonitrile, 10% water; 0.1% AcOH modifier. Gradient initial condition is 100% A with hold time 0.5 min; gradient time is 3 min. Gradient final conc. is 100% B. gradient final hold is 0.5 min. Run time 5 min. Flow rate 1.5 ml/min.

Method 3. detection UV220, Phenomenex Luna 2.5 micron $C_{18}$ $100 \times 2.00$ mm column, Solvent A is water (0.05% TFA), Solvent B is acetonitrile (0.025% TFA). Gradient initial condition is 95% A, 5% B with hold time 0.1 min; gradient time is 2.1 min. Gradient final conc. is 100% B, 5% A. gradient final hold is 0.5 min. Then another hold for further 0.3 min with 98% A, 2% B. Run time 3 min. Flow rate 0.30 to 0.5 ml/min.

The LCMS retention times are from Method 1 unless indicated otherwise.

| Cmpd. # | Structure | Name | AC50 | LCMS ret. time (min.) |
|---|---|---|---|---|
| NCGC00188758-01 | 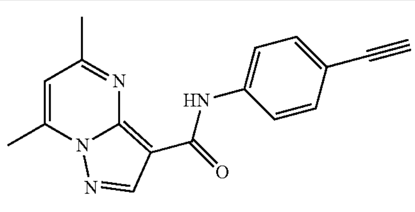 [SMILES: C#Cc1ccc(NC(=O)c2cnn3c(C)cc(C)nc23)cc1] | N-(4-ethynylphenyl)-5,7-dimethylpyrazolo[1,5-a]pyrimidine-3-carboxamide | 0.3659 | 5.784 |
| NCGC00188783-01 | 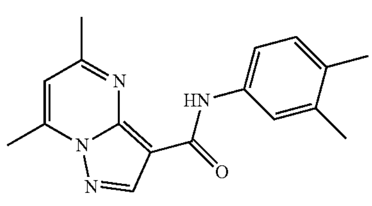 | N-(3,4-dimethylphenyl)-5,7-dimethylpyrazolo[1,5-a]pyrimidine-3-carboxamide | 1.4566 | 6.094 |

| Cmpd. # | Structure | Name | AC50 | LCMS ret. time (min.) |
|---|---|---|---|---|
| NCGC00188787-01 | 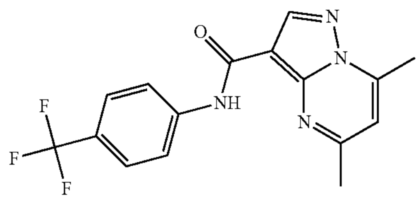 [SMILES: Cc1cc(C)n2ncc(C(=O)Nc3ccc(C(F)(F)F)cc3)c2n1] | 5,7-dimethyl-N-(4-(trifluoromethyl)phenyl)pyrazolo[1,5-a]pyrimidine-3-carboxamide | 1.4566 | 6.434 |
| NCGC00188776-01 | 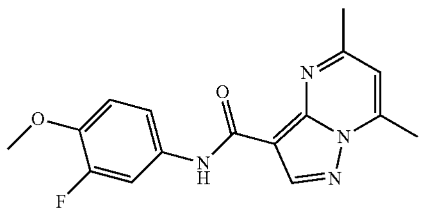 | N-(3-fluoro-4-methoxyphenyl)-5,7-dimethylpyrazolo[1,5-a]pyrimidine-3-carboxamide | 1.4566 | 5.519 |
| NCGC00188772-01 | 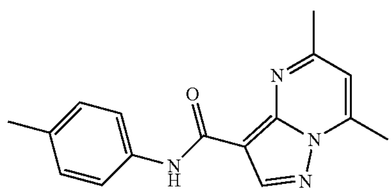 | 5,7-dimethyl-N-p-tolylpyrazolo[1,5-a]pyrimidine-3-carboxamide | 1.6343 | 5.823 |
| NCGC00188782-01 | 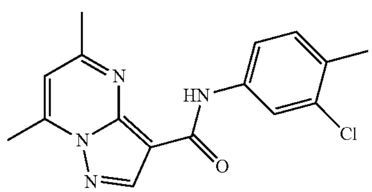 | N-(3-chloro-4-methylphenyl)-5,7-dimethylpyrazolo[1,5-a]pyrimidine-3-carboxamide | 1.8338 | 6.437 |
| NCGC00188756-01 | 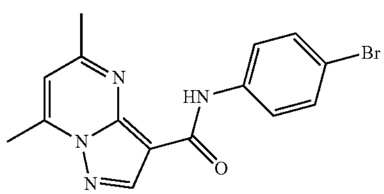 [SMILES: Cc1cc(C)n2ncc(C(=O)Nc3ccc(Br)cc3)c2n1] | N-(4-bromophenyl)-5,7-dimethylpyrazolo[1,5-a]pyrimidine-3-carboxamide | 2.0575 | 6.208 |
| NCGC00188780-01 | 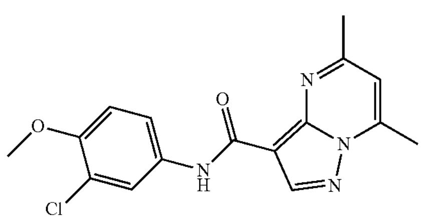 | N-(3-chloro-4-methoxyphenyl)-5,7-dimethylpyrazolo[1,5-a]pyrimidine-3-carboxamide | 2.0575 | 5.793 |
| NCGC00229708-01 | 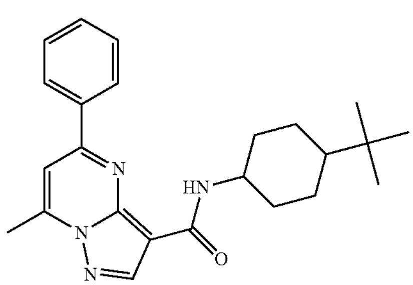 [SMILES: Cc1cc(-c2ccccc2)nc2c(C(=O)NC3CCC(C(C)(C)C)CC3)cnn12] | N-(4-tert-butylcyclohexyl)-7-methyl-5-phenylpyrazolo[1,5-a]pyrimidine-3-carboxamide | 2.0575 | 7.439 |

-continued

| Cmpd. # | Structure | Name | AC50 | LCMS ret. time (min.) |
|---|---|---|---|---|
| MLS000708974-01 | 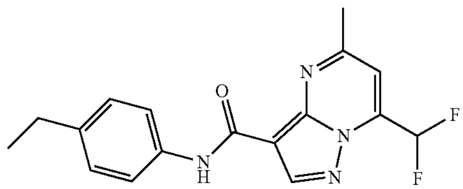 [SMILES: CCc1ccc(NC(=O)c2cnn3c(C(F)F)cc(C)nc23)cc1] | 7-(difluoromethyl)-N-(4-ethylphenyl)-5-methylpyrazolo[1,5-a]pyrimidine-3-carboxamide | 2.2387 | 2.47 Method 2 |
| NCGC00188764-01 | 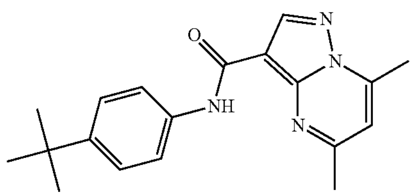 [SMILES: Cc1cc(C)n2ncc(C(=O)Nc3ccc(C(C)(C)C)cc3)c2n1] | N-(4-tert-butylphenyl)-5,7-dimethylpyrazolo[1,5-a]pyrimidine-3-carboxamide | 2.3086 | 6.745 |
| NCGC00182141-01 | 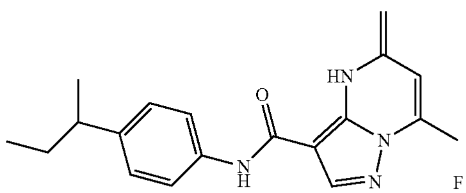 | N-(4-sec-butylphenyl)-7-(difluoromethyl)-5-methylene-4,5-dihydropyrazolo[1,5-a]pyrimidine-3-carboxamide | 2.5119 | 2.67 Method 3 |
| NCGC00182160-01 | 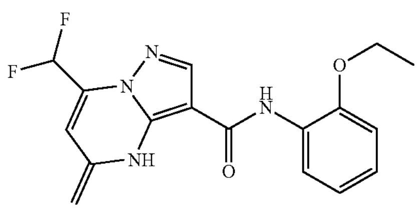 [SMILES: C=C1C=C(C(F)F)n2ncc(C(=O)Nc3ccccc3OCC)c2N1] | 7-(difluoromethyl)-N-(2-ethoxyphenyl)-5-methylene-4,5-dihydropyrazolo[1,5-a]pyrimidine-3-carboxamide | 2.5119 | 2.44 Method 3 |
| NCGC00182179-01 | 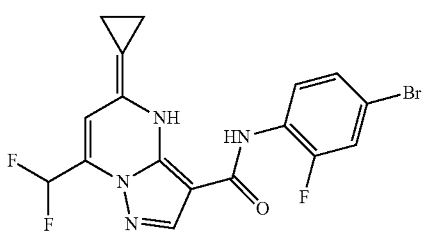 [SMILES: O=C(Nc1ccc(Br)cc1F)c1cnn2c1NC(=C1CC1)C=C2C(F)F] | N-(4-bromo-2-fluorophenyl)-5-cyclopropylidene-7-(difluoromethyl)-4,5-dihydropyrazolo[1,5-a]pyrimidine-3-carboxamide | 2.5119 | 2.71 Method 3 |
| NCGC00187969-01 | 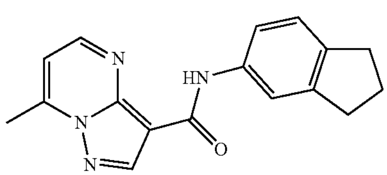 [SMILES: Cc1ccnc2c(C(=O)Nc3ccc4c(c3)CCC4)cnn12] | N-(2,3-dihydro-1H-inden-5-yl)-5,7-dimethylpyrazolo[1,5-a]pyrimidine-3-carboxamide | 2.5902 | 6.328 |
| NCGC00182133-01 | 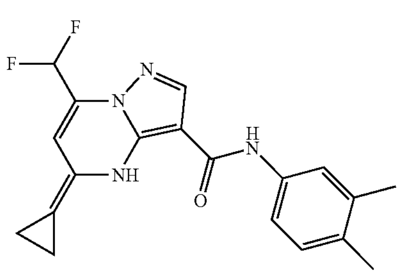 [SMILES: Cc1ccc(NC(=O)c2cnn3c2NC(=C2CC2)C=C3C(F)F)cc1C] | 5-cyclopropylidene-7-(difluoromethyl)-N-(3,4-dimethylphenyl)-4,5-dihydropyrazolo[1,5-a]pyrimidine-3-carboxamide | 3.1623 | 2.59 Method 3 |

-continued

| Cmpd. # | Name | AC50 | LCMS ret. time (min.) |
|---|---|---|---|
| NCGC00182171-01 | N-(5-chloropyridin-2-yl)-5-cyclopropylidene-7-(difluoromethyl)-4,5-dihydropyrazolo[1,5-a]pyrimidine-3-carboxamide | 3.1623 | 2.58 Method 3 |
| NCGC00182172-01 | 5-cyclopropylidene-7-(difluoromethyl)-N-(2,5-difluorophenyl)-4,5-dihydropyrazolo[1,5-a]pyrimidine-3-carboxamide | 3.1623 | 2.57 Method 3 |
| NCGC00187970-01 | N-(4-ethylphenyl)-5,7-dimethylpyrazolo[1,5-a]pyrimidine-3-carboxamide | 3.2609 | 6.231 |
| MLS000662187-01 | 7-(difluoromethyl)-N-(1-(4-fluorobenzyl)-1H-pyrazol-4-yl)-5-phenylpyrazolo[1,5-a]pyrimidine-3-carboxamide | 3.2609 | 2.34 Method 2 |
| NCGC00229713-01 | N-(3,4-dichlorophenyl)-5,7-dimethylpyrazolo[1,5-a]pyrimidine-3-carboxamide | 3.6588 | 6.462 |
| NCGC00182174-01 | 5-cyclopropylidene-7-(difluoromethyl)-N-(2,3-dihydro-1H-inden-5-yl)-4,5-dihydropyrazolo[1,5-a]pyrimidine-3-carboxamide | 3.9811 | 2.64 Method 3 |
| NCGC00182166-01 | N-(2,4-difluorophenyl)-7-methyl-5-methylene-4,5-dihydropyrazolo[1,5-a]pyrimidine-3-carboxamide | 3.9811 | |

-continued

| Cmpd. # | Structure | Name | AC50 | LCMS ret. time (min.) |
|---|---|---|---|---|
| NCGC00188755-01 | 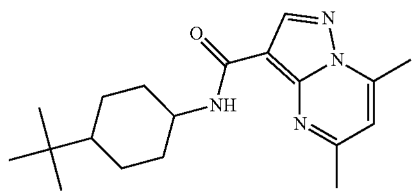 [SMILES: Cc1cc(C)n2ncc(C(=O)NC3CCC(C(C)(C)C)CC3)c2n1] | N-(4-tert-butylcyclohexyl)-5,7-dimethylpyrazolo[1,5-a]pyrimidine-3-carboxamide | 4.1053 | 6.939 |
| MLS000662237-01 | 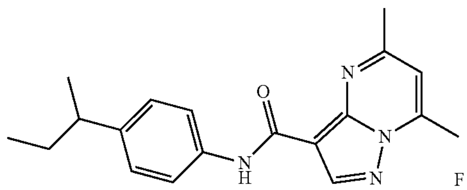 | N-(4-sec-butylphenyl)-7-(difluoromethyl)-5-methylpyrazolo[1,5-a]pyrimidine-3-carboxamide | 5.0119 | 2.76 Method 2 |
| NCGC00188766-01 | 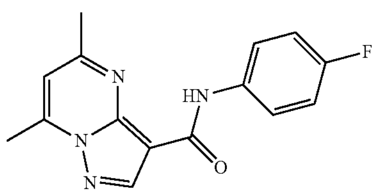 [SMILES: Cc1cc(C)n2ncc(C(=O)Nc3ccc(F)cc3)c2n1] | N-(4-fluorophenyl)-5,7-dimethylpyrazolo[1,5-a]pyrimidine-3-carboxamide | 5.7988 | 5.581 |
| NCGC00229707-01 | 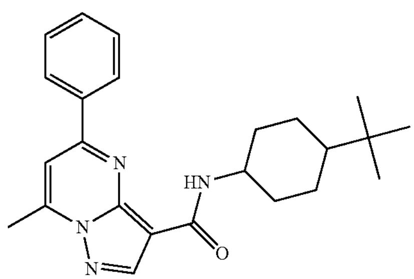 [SMILES: Cc1cc(-c2ccccc2)nc2c(C(=O)NC3CCC(C(C)(C)C)CC3)cnn12] | N-(4-tert-butylcyclohexyl)-7-methyl-5-phenylpyrazolo[1,5-a]pyrimidine-3-carboxamide | 5.7988 | 7.298 |
| NCGC00187967-01 | 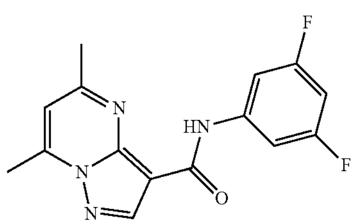 [SMILES: Cc1cc(C)n2ncc(C(=O)Nc3cc(F)cc(F)c3)c2n1] | N-(3,5-difluorophenyl)-5,7-dimethylpyrazolo[1,5-a]pyrimidine-3-carboxamide | 6.1783 | 6.129 |
| NCGC00054856-02 | 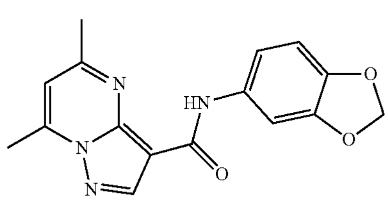 [SMILES: Cc1cc(C)n2ncc(C(=O)Nc3ccc4c(c3)OCO4)c2n1] | N-(benzo[d][1,3]dioxol-5-yl)-5,7-dimethylpyrazolo[1,5-a]pyrimidine-3-carboxamide | 6.5064 | 5.329 |
| NCGC00188771-01 | 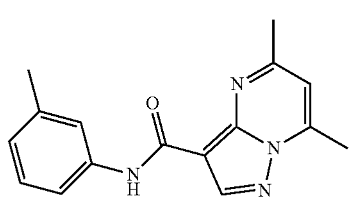 [SMILES: Cc1cccc(NC(=O)c2cnn3c(C)cc(C)nc23)c1] | 5,7-dimethyl-N-m-tolylpyrazolo[1,5-a]pyrimidine-3-carboxamide | 6.5064 | 5.841 |

-continued

| Cmpd. # | Structure | Name | AC50 | LCMS ret. time (min.) |
|---|---|---|---|---|
| NCGC00229715-01 | 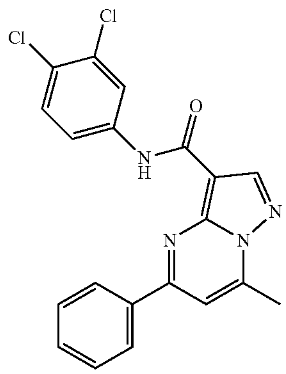 [SMILES: Cc1cc(-c2ccccc2)nc2c(C(=O)Nc3ccc(Cl)c(Cl)c3)cnn12] | N-(3,4-dichlorophenyl)-7-methyl-5-phenylpyrazolo[1,5-a]pyrimidine-3-carboxamide | 6.5064 | 7.257 |
| MLS000765493-01 | 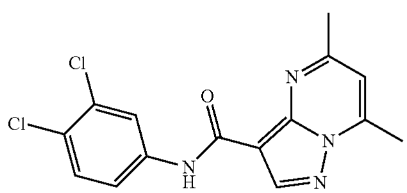 [SMILES: Cc1cc(C)n2ncc(C(=O)Nc3ccc(Cl)c(Cl)c3)c2n1] | N-(3,4-dichlorophenyl)-5,7-dimethylpyrazolo[1,5-a]pyrimidine-3-carboxamide | 7.0795 | 2.66 Method 2 |
| NCGC00182186-01 | 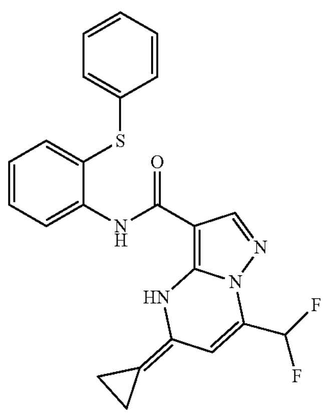 [SMILES: O=C(Nc1ccccc1Sc1ccccc1)c1cnn2c1NC(=C1CC1)C=C2C(F)F] | 5-cyclopropylidene-7-(difluoromethyl)-N-(2-(phenylthio)phenyl)-4,5-dihydropyrazolo[1,5-a]pyrimidine-3-carboxamide | 7.0795 | 2.72 Method 3 |
| NCGC00229719-01 | 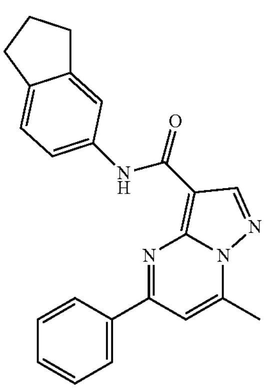 [SMILES: Cc1cc(-c2ccccc2)nc2c(C(=O)Nc3ccc4c(c3)CCC4)cnn12] | N-(2,3-dihydro-1H-inden-5-yl)-7-methyl-5-phenylpyrazolo[1,5-a]pyrimidine-3-carboxamide | 8.1911 | 7.025 |

-continued

| Cmpd. # | Structure | Name | AC50 | LCMS ret. time (min.) |
|---|---|---|---|---|
| NCGC00187975-01 | 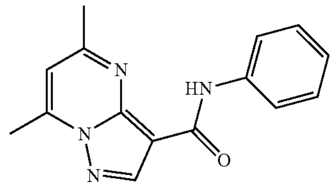 [SMILES: Cc1cc(C)n2ncc(C(=O)Nc3ccccc3)c2n1] | 5,7-dimethyl-N-phenylpyrazolo[1,5-a]pyrimidine-3-carboxamide | 8.1911 | 5.522 |
| NCGC00188768-01 | 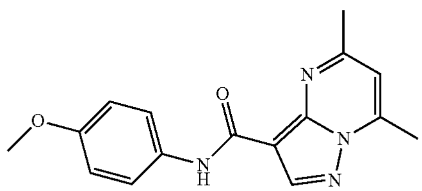 | N-(4-methoxyphenyl)-5,7-dimethylpyrazolo[1,5-a]pyrimidine-3-carboxamide | 8.1911 | 5.328 |
| NCGC00182167-01 | 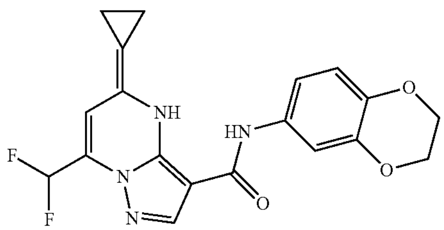 [SMILES: O=C(Nc1ccc2c(c1)OCCO2)c1cnn2c1NC(=C1CC1)C=C2C(F)F] | 5-cyclopropylidene-7-(difluoromethyl)-N-(2,3-dihydrobenzo[b][1,4]dioxin-6-yl)-4,5-dihydropyrazolo[1,5-a]pyrimidine-3-carboxamide | 8.9125 | 2.37 Method 3 |
| NCGC00229717-01 | 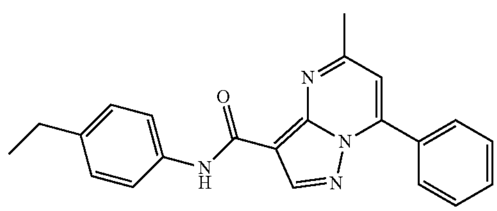 [SMILES: CCc1ccc(NC(=O)c2cnn3c(-c4ccccc4)cc(C)nc23)cc1] | N-(4-ethylphenyl)-5-methyl-7-phenylpyrazolo[1,5-a]pyrimidine-3-carboxamide | 9.1905 | 6.884 |
| NCGC00182142-01 | 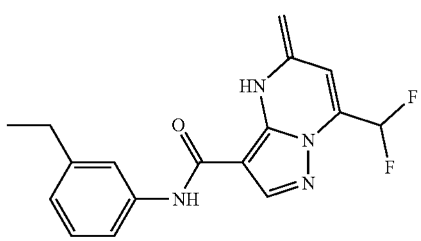 [SMILES: C=C1C=C(C(F)F)n2ncc(C(=O)Nc3cccc(CC)c3)c2N1] | 7-(difluoromethyl)-N-(3-ethylphenyl)-5-methylene-4,5-dihydropyrazolo[1,5-a]pyrimidine-3-carboxamide | 10 | 2.50 Method 3 |
| NCGC00182146-01 | 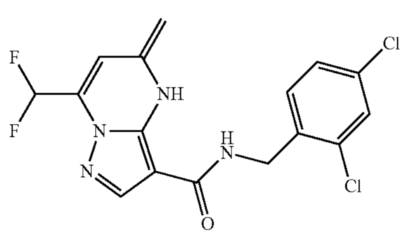 [SMILES: C=C1C=C(C(F)F)n2ncc(C(=O)NCc3ccc(Cl)cc3Cl)c2N1] | N-(2,4-dichlorobenzyl)-7-(difluoromethyl)-5-methylene-4,5-dihydropyrazolo(1,5-a]pyrimidine-3-carboxamide | 10 | 2.48 Method 3 |
| NCGC00182165-01 | 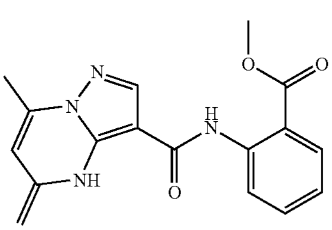 [SMILES: C=C1C=C(C)n2ncc(C(=O)Nc3ccccc3C(=O)OC)c2N1] | methyl 2-(7-methyl-5-methylene-4,5-dihydropyrazolo[1,5-a]pyrimidine-3-carboxamido)benzoate | 10 | 2.36 Method 3 |

| Cmpd. # | Structure | Name | AC50 | LCMS ret. time (min.) |
|---|---|---|---|---|
| NCGC00188773-01 | 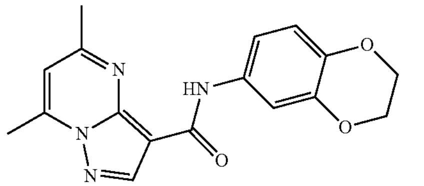 [SMILES: Cc1cc(C)n2ncc(C(=O)Nc3ccc4c(c3)OCCO4)c2n1] | N-(2,3-dihydrobenzo[b][1,4]dioxin-6-yl)-5,7-dimethylpyrazolo[1,5-a]pyrimidine-3-carboxamide | 10.3119 | 5.301 |
| NCGC00187971-01 | 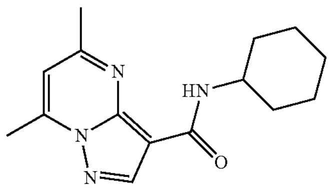 [SMILES: Cc1cc(C)n2ncc(C(=O)NC3CCCCC3)c2n1] | N-cyclohexyl-5,7-dimethylpyrazolo[1,5-a]pyrimidine-3-carboxamide | 10.3119 | 5.551 |
| NCGC00182182-01 | 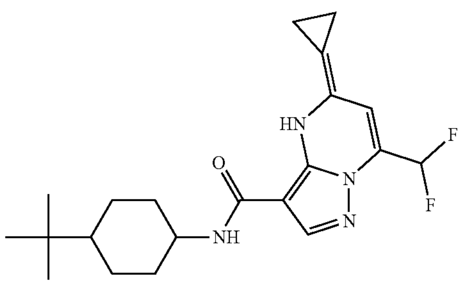 [SMILES: CC(C)(C)C1CCC(NC(=O)c2cnn3c2NC(=C2CC2)C=C3C(F)F)CC1] | N-(4-tert-butylcyclohexyl)-5-cyclopropylidene-7-(difluoromethyl)-4,5-dihydropyrazolo[1,5-a]pyrimidine-3-carboxamide | 11.2202 | 2.83 Method 3 |
| NCGC00182154-01 | 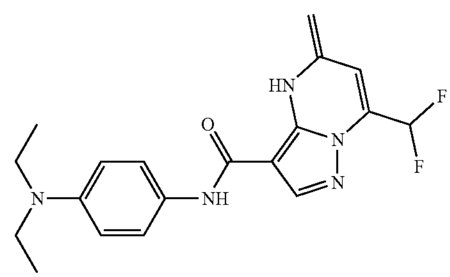 [SMILES: C=C1C=C(C(F)F)n2ncc(C(=O)Nc3ccc(N(CC)CC)cc3)c2N1] | N-(4-(diethylamino)phenyl)-7-(difluoromethyl)-5-methylene-4,5-dihydropyrazolo[1,5-a]pyrimidine-3-carboxamide | 11.2202 | 1.75 Method 3 |
| NCGC00188779-01 | 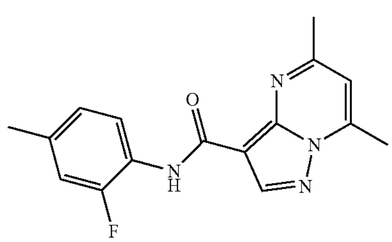 | N-(2-fluoro-4-methylphenyl)-5,7-dimethylpyrazolo[1,5-a]pyrimidine-3-carboxamide | 11.5702 | 6.112 |
| NCGC00182170-01 | 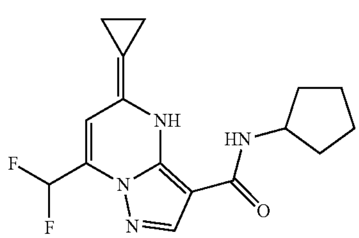 [SMILES: O=C(NC1CCCC1)c1cnn2c1NC(=C1CC1)C=C2C(F)F] | N-cyclopentyl-5-cyclopropylidene-7-(difluoromethyl)-4,5-dihydropyrazolo[1,5-a]pyrimidine-3-carboxamide | 12.5893 | 2.39 Method 3 |

| Cmpd. # | Structure | Name | AC50 | LCMS ret. time (min.) |
|---|---|---|---|---|
| NCGC00182175-01 | 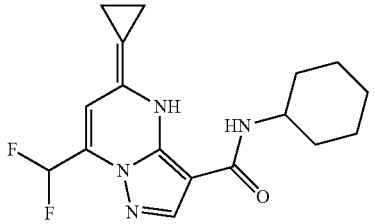 [SMILES: O=C(NC1CCCCC1)c1cnn2c1NC(=C1CC1)C=C2C(F)F] | N-cyclohexyl-5-cyclopropylidene-7-(difluoromethyl)-4,5-dihydropyrazolo[1,5-a]pyrimidine-3-carboxamide | 12.5893 | 2.48 Method 3 |
| NCGC00182139-01 | 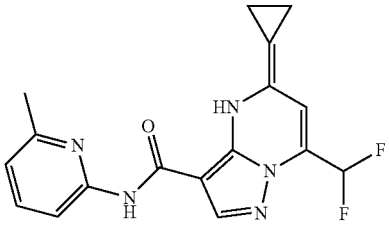 [SMILES: Cc1cccc(NC(=O)c2cnn3c2NC(=C2CC2)C=C3C(F)F)n1] | 5-cyclopropylidene-7-(difluoromethyl)-N-(6-methylpyridin-2-yl)-4,5-dihydropyrazolo[1,5-a]pyrimidine-3-carboxamide | 12.5893 | 2.15 Method 3 |
| NCGC00182185-01 | 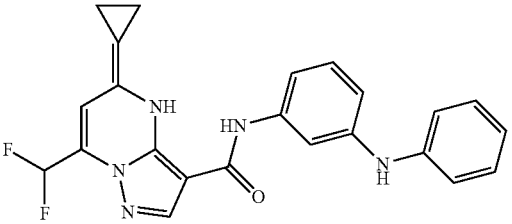 [SMILES: O=C(Nc1cccc(Nc2ccccc2)c1)c1cnn2c1NC(=C1CC1)C=C2C(F)F] | 5-cyclopropylidene-7-(difluoromethyl)-N-(3-(phenylamino)phenyl)-4,5-dihydropyrazolo[1,5-a]pyrimidine-3-carboxamide | 12.5893 | 2.55 Method 3 |
| NCGC00182188-01 | 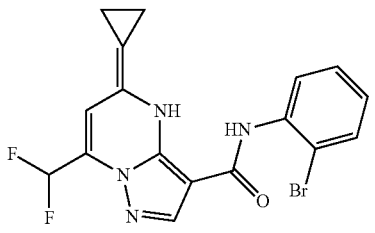 [SMILES: O=C(Nc1ccccc1Br)c1cnn2c1NC(=C1CC1)C=C2C(F)F] | N-(2-bromophenyl)-5-cyclopropylidene-7-(difluoromethyl)-4,5-dihydropyrazolo[1,5-a]pyrimidine-3-carboxamide | 12.5893 | 2.60 Method 3 |
| NCGC00182186-01 | 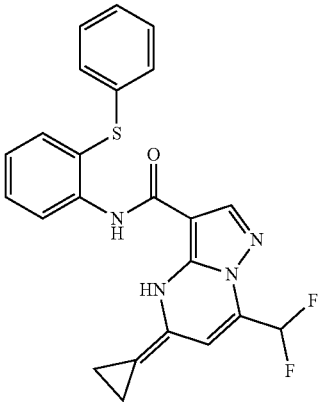 [SMILES: O=C(Nc1ccccc1Sc1ccccc1)c1cnn2c1NC(=C1CC1)C=C2C(F)F] | 5-cyclopropylidene-7-(difluoromethyl)-N-(2-(phenylthio)phenyl)-4,5-dihydropyrazolo[1,5-a]pyrimidine-3-carboxamide | 12.982 | 2.72 Method 3 |

| Cmpd. # | Structure | Name | AC50 | LCMS ret. time (min.) |
|---|---|---|---|---|
| NCGC00188778-01 | 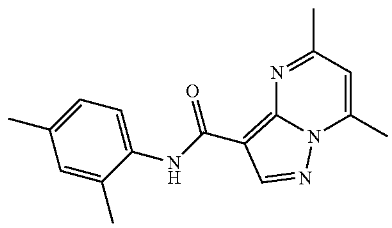 | N-(2,4-dimethylphenyl)-5,7-dimethylpyrazolo[1,5-a]pyrimidine-3-carboxamide | 12.982 | 6.112 |
| NCGC00229714-01 | 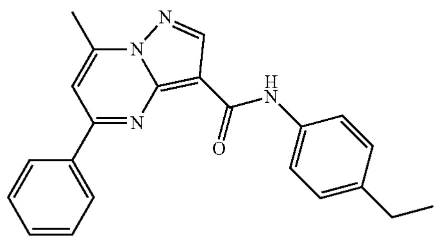 [SMILES: CCc1ccc(NC(=O)c2cnn3c(C)cc(-c4ccccc4)nc23)cc1] | N-(4-ethylphenyl)-7-methyl-5-phenylpyrazolo[1,5-a]pyrimidine-3-carboxamide | 12.982 | 6.914 |
| NCGC00182162-01 | 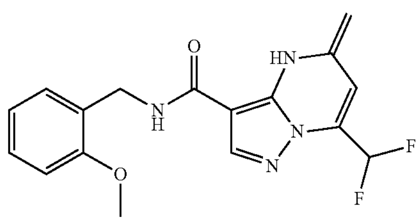 [SMILES: C=C1C=C(C(F)F)n2ncc(C(=O)NCc3ccccc3OC)c2N1] | 7-(difluoromethyl)-N-(2-methoxybenzyl)-5-methylene-4,5-dihydropyrazolo]1,5-a]pyrimidine-3-carboxamide | 14.1254 | 2.26 Method 3 |
| NCGC00182190-01 | 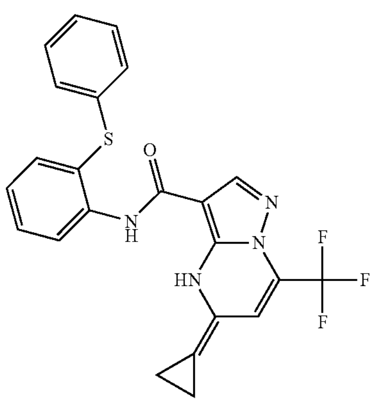 [SMILES: O=C(Nc1ccccc1Sc1ccccc1)c1cnn2c1NC(=C1CC1)C=C2C(F)(F)F] | 5-cyclopropylidene-N-(2-(phenylthio)phenyl)-7-(trifluoromethyl)-4,5-dihydropyrazolo[1,5-a]pyrimidine-3-carboxamide | 14.1254 | 2.76 Method 3 |
| NCGC00182176-01 | 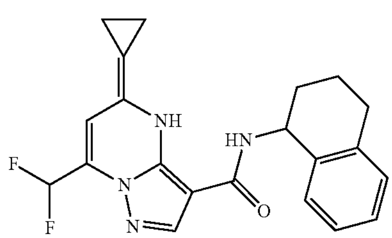 [SMILES: O=C(NC1CCCc2ccccc21)c1cnn2c1NC(=C1CC1)C=C2C(F)F] | 5-cyclopropylidene-7-(difluoromethyl)-N-(1,2,3,4-tetrahydronaphthalen-1-yl)-4,5-dihydropyrazolo[1,5-a]pyrimidine-3-carboxamide | 14.1254 | |

| Cmpd. # | Structure | Name | AC50 | LCMS ret. time (min.) |
|---|---|---|---|---|
| NCGC00182148-01 | 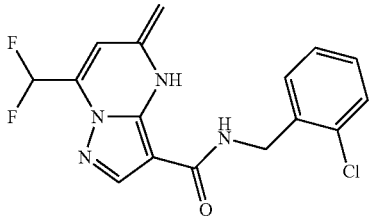 | N-(2-chlorobenzyl)-7-(difluoromethyl)-5-methylene-4,5-dihydropyrazolo(1,5-a]pyrimidine-3-carboxamide | 14.1254 | 2.35 Method 3 |
| NCGC00182132-01 | 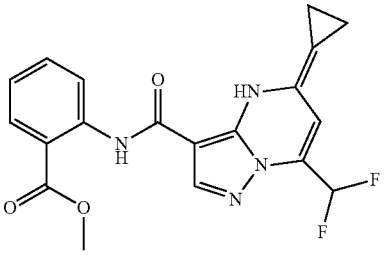 [SMILES: COC(=O)c1ccccc1NC(=O)c1cnn2c1NC(=C1CC1)C=C2C(F)F] | methyl 2-(5-cyclopropylidene-7-(difluoromethyl)-4,5-dihydropyrazolo[1,5-a]pyrimidine-3-carboxamido)benzoate | 15.8489 | 2.54 Method 3 |
| NCGC00182159-01 | 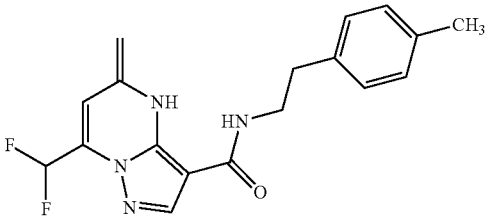 [SMILES: C=C1C=C(C(F)F)n2ncc(C(=O)NCCc3ccc(C)cc3)c2N1] | N-(4-chlorophenethyl)-7-(difluoromethyl)-5-methylene-4,5-dihydropyrazolo[1,5-a]pyrimidine-3-carboxamide | 15.8489 | 2.40 Method 3 |
| NCGC00182161-01 | 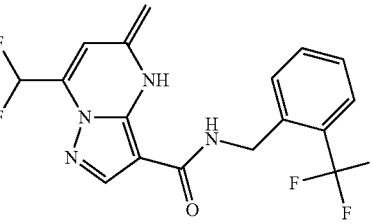 | 7-(difluoromethyl)-5-methylene-N-(2-(trifluoromethyl)benzyl)-4,5-dihydropyrazolo[1,5-a]pyrimidine-3-carboxamide | 15.8489 | 2.39 Method 3 |
| NCGC00182197-01 | 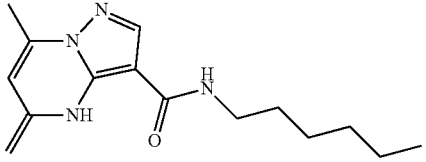 [SMILES: C=C1C=C(C)n2ncc(C(=O)NCCCCCC)c2N1] | N-hexyl-7-methyl-5-methylene-4,5-dihydropyrazolo[1,5-a]pyrimidine-3-carboxamide | 15.8489 | 2.47 Method 3 |
| NCGC00182198-01 | 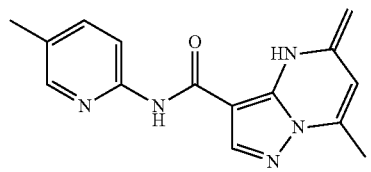 | 7-methyl-5-methylene-N-(5-methylpyridin-2-yl)-4,5-dihydropyrazolo[1,5-a]pyrimidine-3-carboxamide | 15.8489 | 1.78 Method 3 |
| NCGC00188770-01 | 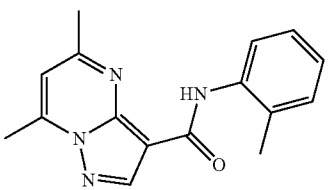 [SMILES: Cc1cc(C)n2ncc(C(=O)Nc3ccccc3C)c2n1] | 5,7-dimethyl-N-o-tolylpyrazolo[1,5-a]pyrimidine-3-carboxamide | 16.3433 | 5.730 |

-continued

| Cmpd. # | Structure | Name | AC50 | LCMS ret. time (min.) |
|---|---|---|---|---|
| NCGC00188762-01 | 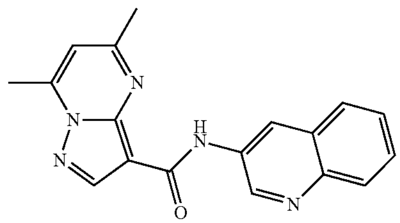 [SMILES: Cc1cc(C)n2ncc(C(=O)Nc3cnc4ccccc4c3)c2n1] | 5,7-dimethyl-N-(quinolin-3-yl)pyrazolo[1,5-a]pyrimidine-3-carboxamide | 16.3433 | 4.266 |
| NCGC00187965-01 | 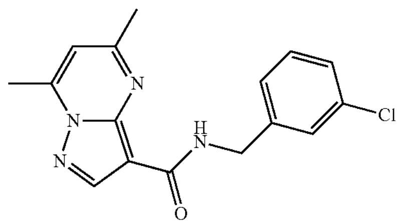 [SMILES: Cc1cc(C)n2ncc(C(=O)NCc3cccc(Cl)c3)c2n1] | N-(3-chlorobenzyl)-5,7-dimethylpyrazolo[1,5-a]pyrimidine-3-carboxamide | 18.3375 | 5.639 |
| NCGC00229712-01 | 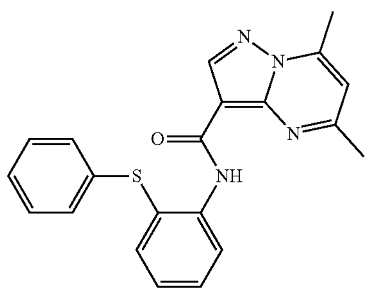 [SMILES: Cc1cc(C)n2ncc(C(=O)Nc3ccccc3Sc3ccccc3)c2n1] | 5,7-dimethyl-N-(2-(phenylthio)phenyl)pyrazolo[1,5-a]pyrimidine-3-carboxamide | 18.3375 | 6.590 |
| NCGC00188763-01 | 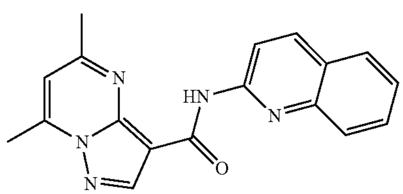 [SMILES: Cc1cc(C)n2ncc(C(=O)Nc3ccc4ccccc4n3)c2n1] | 5,7-dimethyl-N-(quinolin-2-yl)pyrazolo[1,5-a]pyrimidine-3-carboxamide | 20.575 | 4.637 |
| NCGC00188769-01 | 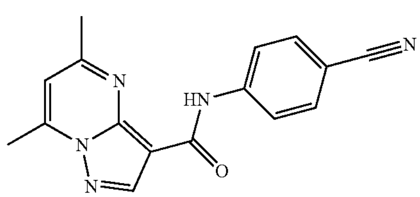 [SMILES: Cc1cc(C)n2ncc(C(=O)Nc3ccc(C#N)cc3)c2n1] | N-(4-cyanophenyl)-5,7-dimethylpyrazolo[1,5-a]pyrimidine-3-carboxamide | 20.575 | 5.441 |
| NCGC00182147-01 | 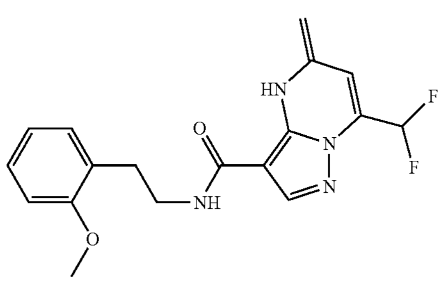 [SMILES: C=C1C=C(C(F)F)n2ncc(C(=O)NCCc3ccccc3OC)c2N1] | 7-(difluoromethyl)-N-(2-methoxyphenethyl)-5-methylene-4,5-dihydropyrazolo[1,5-a]pyrimidine-3-carboxamide | 25.1189 | 2.31 Method 3 |

-continued

| Cmpd. # | Structure | Name | AC50 | LCMS ret. time (min.) |
|---|---|---|---|---|
| NCGC00188754-01 | 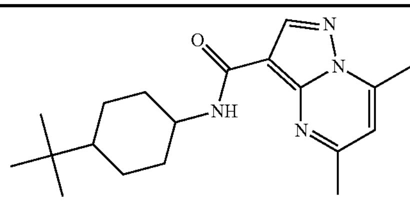 | N-(4-tert-butylcyclohexyl)-5,7-dimethylpyrazolo[1,5-a]pyrimidine-3-carboxamide | 25.9024 | 6.816 |
| NCGC00188781-01 | 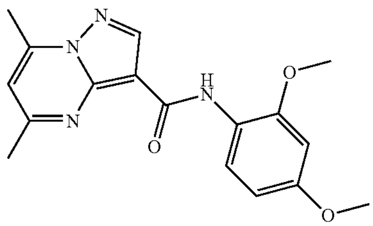 [SMILES: COc1ccc(NC(=O)c2cnn3c(C)cc(C)nc23)c(OC)c1] | N-(2,4-dimethoxyphenyl)-5,7-dimethylpyrazolo[1,5-a]pyrimidine-3-carboxamide | 25.9024 | 5.483 |
| NCGC00229716-01 | 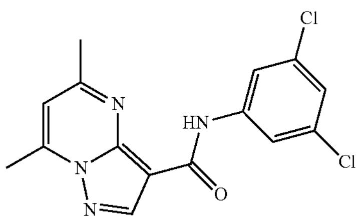 [SMILES: Cc1cc(C)n2ncc(C(=O)Nc3cc(Cl)cc(Cl)c3)c2n1] | N-(3,5-dichlorophenyl)-5,7-dimethylpyrazolo[1,5-a]pyrimidine-3-carboxamide | 25.9024 | 6.715 |
| NCGC00182145-01 | 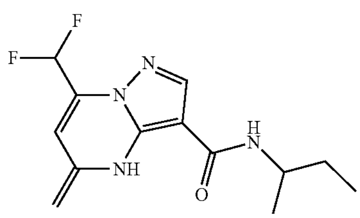 [SMILES: C=C1C=C(C(F)F)n2ncc(C(=O)NC(C)CC)c2N1] | N-sec-butyl-7-(difluoromethyl)-5-methylene-4,5-dihydropyrazolo[1,5-a]pyrimidine-3-carboxamide | 31.6228 | 2.22 Method 3 |
| NCGC00182151-01 | 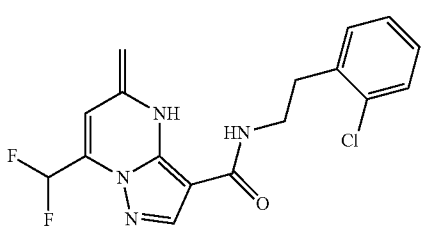 [SMILES: C=C1C=C(C(F)F)n2ncc(C(=O)NCCc3ccccc3Cl)c2N1] | N-(2-chlorophenethyl)-7-(difluoromethyl)-5-methylene-4,5-dihydropyrazolo[1,5-a]pyrimidine-3-carboxamide | 31.6228 | 2.38 Method 3 |
| NCGC00182152-01 | 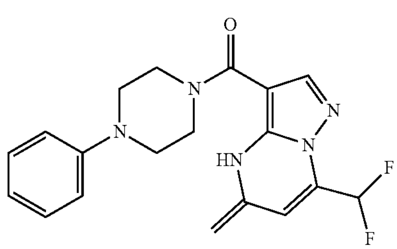 [SMILES: C=C1C=C(C(F)F)n2ncc(C(=O)N3CCN(c4ccccc4)CC3)c2N1] | (7-(difluoromethyl)-5-methylene-4,5-dihydropyrazolo[1,5-a]pyrimidin-3-yl)(4-phenylpiperazin-1-yl)methanone | 31.6228 | 2.08 Method 3 |
| NCGC00187978-01 | 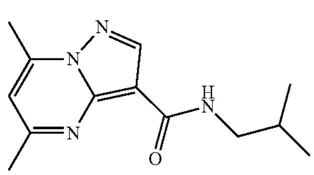 [SMILES: Cc1cc(C)n2ncc(C(=O)NCC(C)C)c2n1] | N-isobutyl-5,7-dimethylpyrazolo[1,5-a]pyrimidine-3-carboxamide | 32.6092 | 5.075 |

-continued

| Cmpd. # | Structure | Name | AC50 | LCMS ret. time (min.) |
|---|---|---|---|---|
| NCGC00188785-01 | 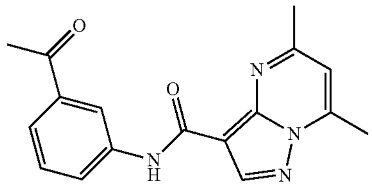 [SMILES: CC(=O)c1cccc(NC(=O)c2cnn3c(C)cc(C)nc23)c1] | N-(3-acetylphenyl)-5,7-dimethylpyrazolo[1,5-a]pyrimidine-3-carboxamide | 32.6092 | 5.266 |
| NCGC00229711-01 | 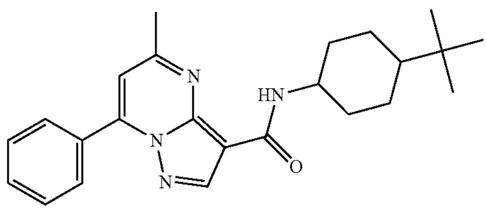 [SMILES: Cc1cc(-c2ccccc2)n2ncc(C(=O)NC3CCC(C(C)(C)C)CC3)c2n1] | N-(4-tert-butylcyclohexyl)-5-methyl-7-phenylpyrazolo[1,5-a]pyrimidine-3-carboxamide | 32.6092 | 7.407 |
| NCGC00182144-01 | 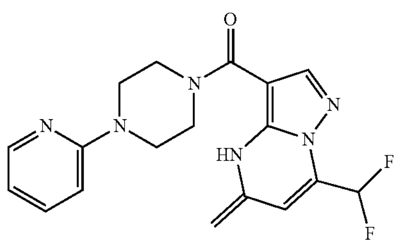 [SMILES: C=C1C=C(C(F)F)n2ncc(C(=O)N3CCN(c4ccccn4)CC3)c2N1] | (7-(difluoromethyl)-5-methylene-4,5-dihydropyrazolo[1,5-a]pyrimidin-3-yl)(4-(pyridin-2-yl)piperazin-1-yl)methanone | 35.4813 | 1.59 |
| NCGC00188786-01 | 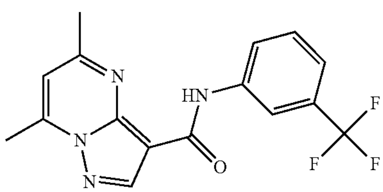 [SMILES: Cc1cc(C)n2ncc(C(=O)Nc3cccc(C(F)(F)F)c3)c2n1] | 5,7-dimethyl-N-(3-(trifluoromethyl)phenyl)pyrazolo[1,5-a]pyrimidine-3-carboxamide | 41.0526 | 6.364 |
| NCGC00187976-01 | 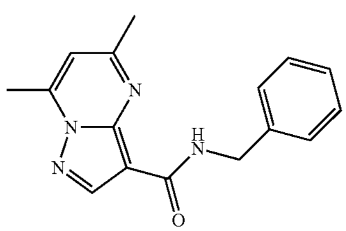 [SMILES: Cc1cc(C)n2ncc(C(=O)NCc3ccccc3)c2n1] | N-benzyl-5,7-dimethylpyrazolo[1,5-a]pyrimidine-3-carboxamide | 51.6821 | 5.189 |
| NCGC00188759-01 | 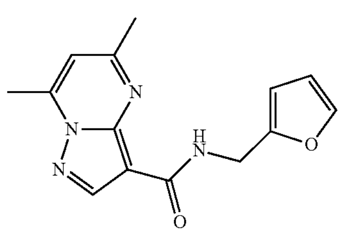 [SMILES: Cc1cc(C)n2ncc(C(=O)NCc3ccco3)c2n1] | N-(furan-2-ylmethyl)-5,7-dimethylpyrazolo[1,5-a]pyrimidine-3-carboxamide | 51.6821 | 4.723 |

-continued

| Cmpd. # | Structure | Name | AC50 | LCMS ret. time (min.) |
|---|---|---|---|---|
| NCGC00188774-01 | 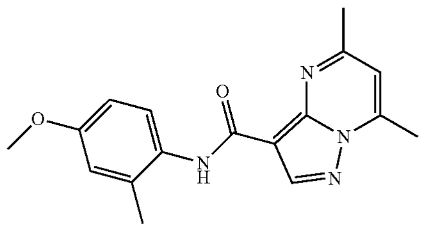 | N-(4-methoxy-2-methylphenyl)-5,7-dimethylpyrazolo[1,5-a]pyrimidine-3-carboxamide | 51.6821 | 5.530 |
| NCGC00188784-01 | 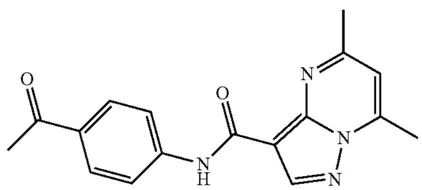 [SMILES: CC(=O)c1ccc(NC(=O)c2cnn3c(C)cc(C)nc23)cc1] | N-(4-acetylphenyl)-5,7-dimethylpyrazolo[1,5-a]pyrimidine-3-carboxamide | 163.4332 | 5.250 |
| NCGC00229718-01 | 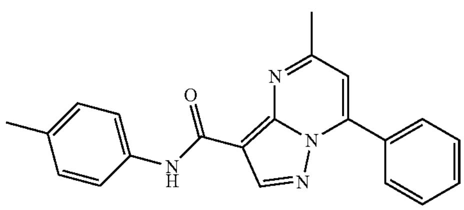 [SMILES: Cc1ccc(NC(=O)c2cnn3c(-c4ccccc4)cc(C)nc23)cc1] | 5-methyl-7-phenyl-N-p-tolylpyrazolo[1,5-a]pyrimidine-3-carboxamide | 205.7502 | 6.585 |
| MLS000663265-01 | 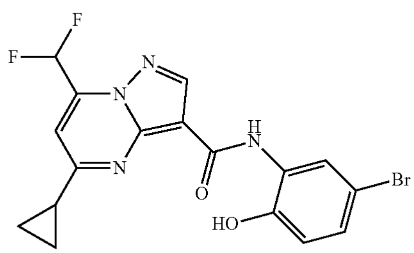 [SMILES: O=C(Nc1cc(Br)ccc1O)c1cnn2c(C(F)F)cc(C3CC3)nc12] | N-(5-bromo-2-hydroxyphenyl)-5-cyclopropyl-7-(difluoromethyl)pyrazolo[1,5-a]pyrimidine-3-carboxamide | 2.36 | Method 2 |
| MLS000716072-01 | 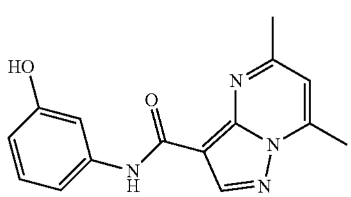 [SMILES: Cc1cc(C)n2ncc(C(=O)Nc3cccc(O)c3)c2n1] | N-(3-hydroxyphenyl)-5,7-dimethylpyrazolo[1,5-a]pyrimidine-3-carboxamide | 1.86 | Method 2 |
| NCGC00182126-01 | 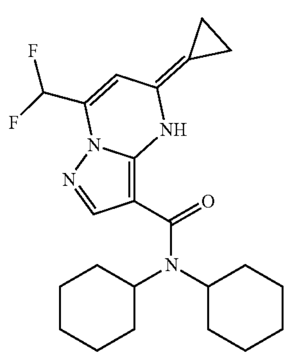 [SMILES: O=C(c1cnn2c1NC(=C1CC1)C=C2C(F)F)N(C1CCCCC1)C1CCCCC1] | N,N-dicyclohexyl-5-cyclopropylidene-7-(difluoromethyl)-4,5-dihydropyrazolo[1,5-a]pyrimidine-3-carboxamide | 2.84 | Method 3 |

-continued

| Cmpd. # | Structure | Name | AC50 | LCMS ret. time (min.) |
|---|---|---|---|---|
| NCGC00182127-01 | 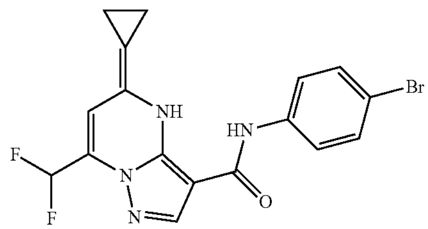 [SMILES: O=C(Nc1ccc(Br)cc1)c1cnn2c1NC(=C1CC1)C=C2C(F)F] | N-(4-bromophenyl)-5-cyclopropylidene-7-(difluoromethyl)-4,5-dihydropyrazolo[1,5-a]pyrimidine-3-carboxamide | | 2.60 Method 3 |
| NCGC00182128-01 | 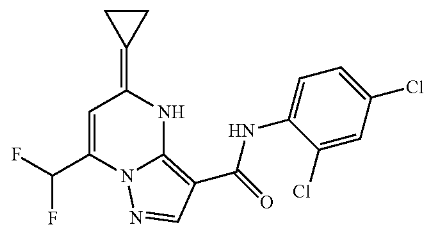 | 5-cyclopropylidene-N-(2,4-dichlorophenyl)-7-(difluoromethyl)-4,5-dihydropyrazolo[1,5-a]pyrimidine-3-carboxamide | | 2.78 Method 3 |
| NCGC00182129-01 | 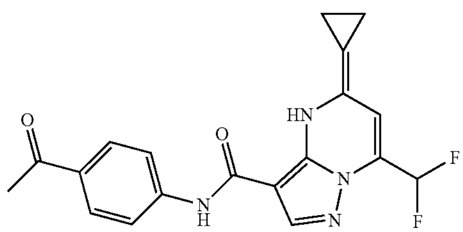 [SMILES: CC(=O)c1ccc(NC(=O)c2cnn3c2NC(=C2CC2)C=C3C(F)F)cc1] | N-(4-acetylphenyl-5-cyclopropylidene-7-(difluoromethyl)-4,5-dihydropyrazolo[1,5-a]pyrimidine-3-carboxamide | | 2.35 Method 3 |
| NCGC00182130-01 | 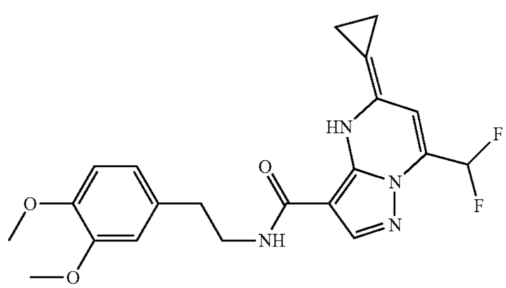 [SMILES: COc1ccc(CCNC(=O)c2cnn3c2NC(=C2CC2)C=C3C(F)F)cc1OC] | 5-cyclopropylidene-7-(difluoromethyl)-N-(3,4-dimethoxyphenethyl)-4,5-dihydropyrazolo[1,5-a]pyrimidine-3-carboxamide | | 2.25 Method 3 |
| NCGC00182131-01 | 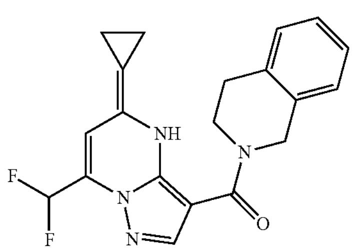 [SMILES: O=C(c1cnn2c1NC(=C1CC1)C=C2C(F)F)N1CCc2ccccc2C1] | (5-cyclopropylidene-7-(difluoromethyl)-4,5-dihydropyrazolo[1,5-a]pyrimidin-3-yl)(3,4-dihydroisoquinolin-2(1H)-yl)methanone | | 2.37 Method 3 |
| NCGC00182134-01 | 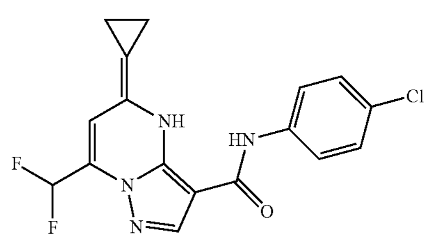 [SMILES: O=C(Nc1ccc(Cl)cc1)c1cnn2c1NC(=C1CC1)C=C2C(F)F] | N-(4-chlorophenyl)-5-cyclopropylidene-7-(difluoromethyl)-4,5-dihydropyrazolo[1,5-a]pyrimidine-3-carboxamide | | 2.57 Method 3 |

-continued

| Cmpd. # | Structure | Name | AC50 | LCMS ret. time (min.) |
|---|---|---|---|---|
| NCGC00182135-01 | 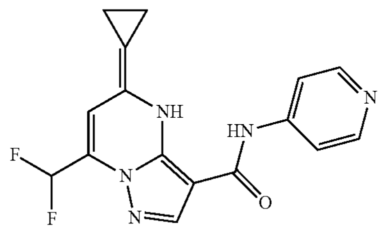 [SMILES: O=C(Nc1ccncc1)c1cnn2c1NC(=C1CC1)C=C2C(F)F] | 5-cyclopropylidene-7-(difluoromethyl)-N-(pyridin-4-yl)-4,5-dihydropyrazolo[1,5-a]pyrimidine-3-carboxamide | | 1.71 Method 3 |
| NCGC00182136-01 | 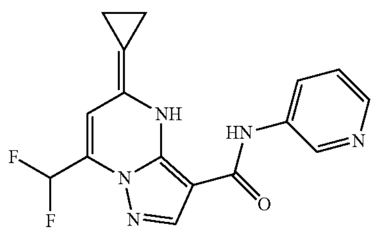 [SMILES: O=C(Nc1cccnc1)c1cnn2c1NC(=C1CC1)C=C2C(F)F] | 5-cyclopropylidene-7-(difluoromethyl)-N-(pyridin-3-yl)-4,5-dihydropyrazolo[1,5-a]pyrimidine-3-carboxamide | | 1.73 Method 3 |
| NCGC00182137-01 | 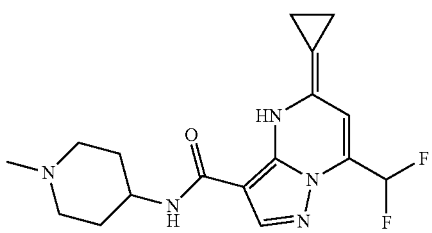 [SMILES: CN1CCC(NC(=O)c2cnn3c2NC(=C2CC2)C=C3C(F)F)CC1] | 5-cyclopropylidene-7-(difluoromethyl)-N-(1-methylpiperidin-4-yl)-4,5-dihydropyrazolo[1,5-a]pyrimidine-3-carboxamide | | 1.65 Method 3 |
| NCGC00182138-01 | 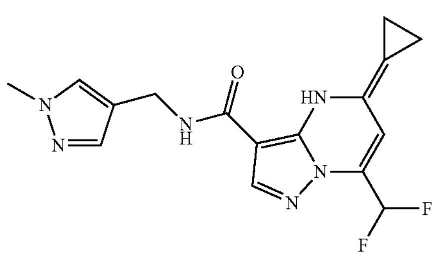 [SMILES: Cn1cc(CNC(=O)c2cnn3c2NC(=C2CC2)C=C3C(F)F)cn1] | 5-cyclopropylidene-7-(difluoromethyl)-N-((1-methyl-1H-pyrazol-4-yl)methyl)-4,5-dihydropyrazolo[1,5-a]pyrimidine-3-carboxamide | | 1.99 Method 3 |
| NCGC00182140-01 | 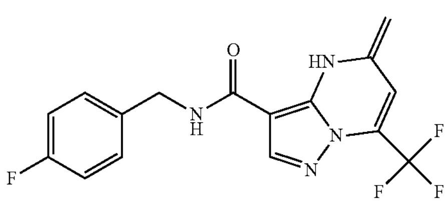 [SMILES: C=C1C=C(C(F)(F)F)n2ncc(C(=O)NCc3ccc(F)cc3)c2N1] | N-(4-fluorobenzyl)-5-methylene-7-(trifluoromethyl)-4,5-dihydropyrazolo[1,5-a]pyrimidine-3-carboxamide | | 2.29 Method 3 |
| NCGC00182143-01 | 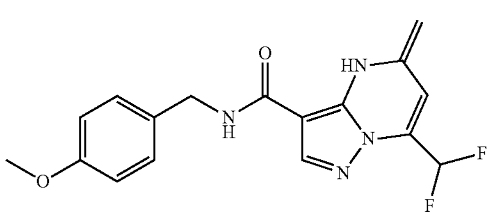 [SMILES: C=C1C=C(C(F)F)n2ncc(C(=O)NCc3ccc(OC)cc3)c2N1] | 7-(difluoromethyl)-N-(4-methoxybenzyl)-5-methylene-4,5-dihydropyrazolo[1,5-a]pyrimidine-3-carboxamide | | 2.21 Method 3 |

| Cmpd. # | Structure | Name | AC50 | LCMS ret. time (min.) |
|---|---|---|---|---|
| NCGC00182149-01 | 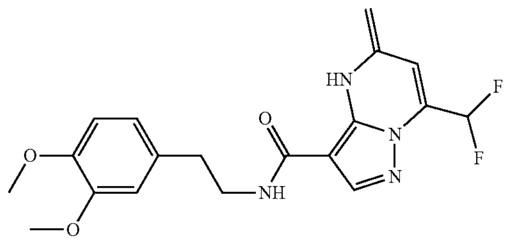 [SMILES: C=C1C=C(C(F)F)n2ncc(C(=O)NCCc3ccc(OC)c(OC)c3)c2N1] | 7-(difluoromethyl)-N-(3,4-dimethoxyphenethyl)-5-methylene-4,5-dihydropyrazolo[1,5-a]pyrimidine-3-carboxamide | | 2.16 Method 3 |
| NCGC00182150-01 | 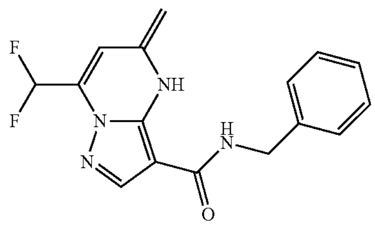 [SMILES: C=C1C=C(C(F)F)n2ncc(C(=O)NCc3ccccc3)c2N1] | N-benzyl-7-(difluoromethyl)-5-methylene-4,5-dihydropyrazolo[1,5-a]pyrimidine-3-carboxamide | | 2.23 Method 3 |
| NCGC00182153-01 | 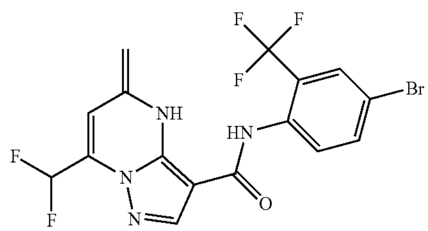 [SMILES: C=C1C=C(C(F)F)n2ncc(C(=O)Nc3ccc(Br)cc3C(F)(F)F)c2N1] | N-(4-bromo-2-(trifluoromethyl)phenyl)-7-(difluoromethyl)-5-methylene-4,5-dihydropyrazolo[1,5-a]pyrimidine-3-carboxamide | | |
| NCGC00182155-01 | 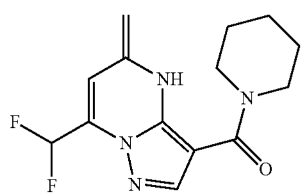 [SMILES: C=C1C=C(C(F)F)n2ncc(C(=O)N3CCCCC3)c2N1] | (7-(difluoromethyl)-5-methylene-4,5-dihydropyrazolo[1,5-a]pyrimidin-3-yl)(piperidin-1-yl)methanone | | 2.09 Method 3 |
| NCGC00182156-01 | 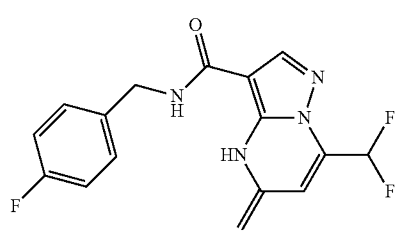 [SMILES: C=C1C=C(C(F)F)n2ncc(C(=O)NCc3ccc(F)cc3)c2N1] | 7-(difluoromethyl)-N-(4-fluorobenzyl)-5-methylene-4,5-dihydropyrazolo[1,5-a]pyrimidine-3-carboxamide | | 2.24 Method 3 |
| NCGC00182157-01 | 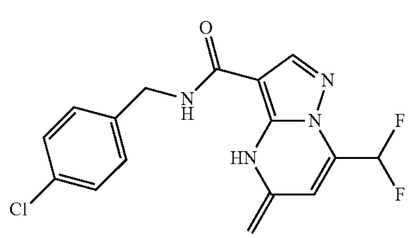 [SMILES: C=C1C=C(C(F)F)n2ncc(C(=O)NCc3ccc(Cl)cc3)c2N1] | N-(4-chlorobenzyl)-7-(difluoromethyl)-5-methylene-4,5-dihydropyrazolo[1,5-a]pyrimidine-3-carboxamide | | 2.34 Method 3 |

| Cmpd. # | Structure | Name | AC50 | LCMS ret. time (min.) |
|---|---|---|---|---|
| NCGC00182158-01 | 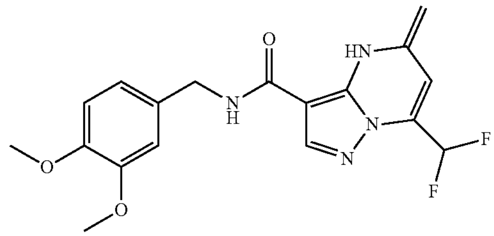 [SMILES: C=C1C=C(C(F)F)n2ncc(C(=O)NCc3ccc(OC)c(OC)c3)c2N1] | 7-(difluoromethyl)-N-(3,4-dimethoxybenzyl)-5-methylene-4,5-dihydropyrazolo[1,5-a]pyrimidine-3-carboxamide | | |
| NCGC00182163-01 | 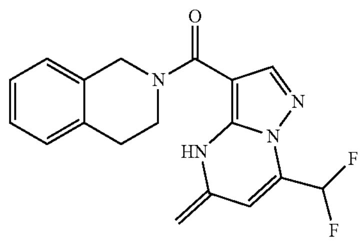 [SMILES: C=C1C=C(C(F)F)n2ncc(C(=O)N3CCc4ccccc4C3)c2N1] | (7-(difluoromethyl)-5-methylene-4,5-dihydropyrazolo[1,5-a]pyrimidin-3-yl)(3,4-dihydroisoquinolin-2(1H)-yl)methanone | | 2.23 Method 3 |
| NCGC00182164-01 | 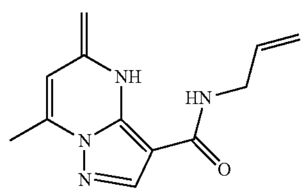 [SMILES: C=CCNC(=O)c1cnn2c1NC(=C)C=C2C] | N-allyl-7-methyl-5-methylene-4,5-dihydropyrazolo[1,5-a]pyrimidine-3-carboxamide | | 2.00 Method 3 |
| NCGC00182168-01 | 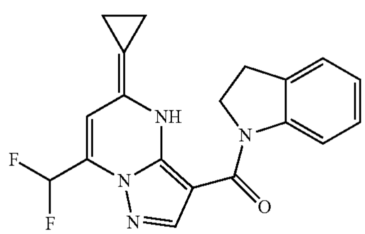 [SMILES: O=C(c1cnn2c1NC(=C1CC1)C=C2C(F)F)N1CCc2ccccc21] | (5-cyclopropylidene-7-(difluoromethyl)-4,5-dihydropyrazolo[1,5-a]pyrimidin-3-yl)(indolin-1-yl)methanone | | 2.39 Method 3 |
| NCGC00182169-01 | 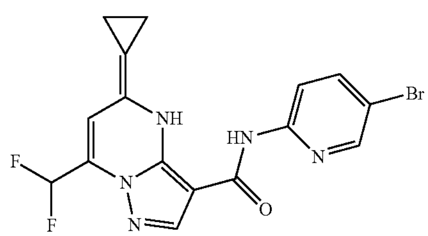 [SMILES: O=C(Nc1ccc(Br)cn1)c1cnn2c1NC(=C1CC1)C=C2C(F)F] | N-(5-bromopyridin-2-yl)-5-cyclopropylidene-7-(difluoromethyl)-4,5-dihydropyrazolo[1,5-a]pyrimidine-3-carboxamide | | 2.62 Method 3 |
| NCGC00182173-01 | 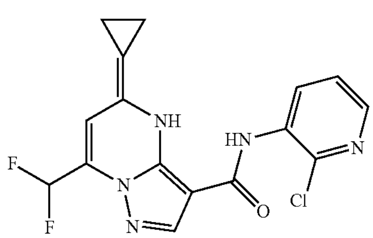 | N-(2-chloropyridin-3-yl)-5-cyclopropylidene-7-(difluoromethyl)-4,5-dihydropyrazolo[1,5-a]pyrimidine-3-carboxamide | | 2.43 Method 3 |

-continued

| Cmpd. # | Structure | Name | AC50 | LCMS ret. time (min.) |
|---|---|---|---|---|
| NCGC00182177-01 | 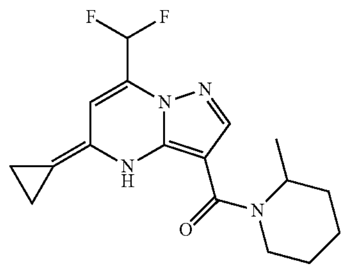 [SMILES: CC1CCCCN1C(=O)c1cnn2c1NC(=C1CC1)C=C2C(F)F] | (5-cyclopropylidene-7-(difluoromethyl)-4,5-dihydropyrazolo[1,5-a]pyrimidin-3-yl)(2-methylpiperidin-1-yl)methanone | | 2.35 Method 3 |
| NCGC00182178-01 | 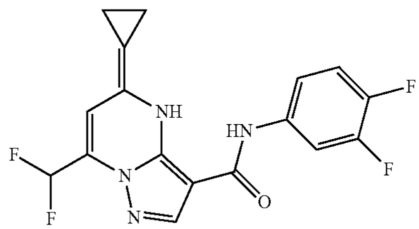 [SMILES: O=C(Nc1ccc(F)c(F)c1)c1cnn2c1NC(=C1CC1)C=C2C(F)F] | 5-cyclopropylidene-7-(difluoromethyl)-N-(3,4-difluorophenyl)-4,5-dihydropyrazolo[1,5-a]pyrimidine-3-carboxamide | | 2.51 Method 3 |
| NCGC00182180-01 | 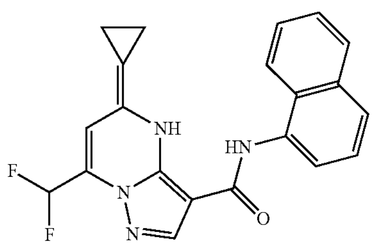 [SMILES: O=C(Nc1cccc2ccccc12)c1cnn2c1NC(=C1CC1)C=C2C(F)F] | 5-cyclopropylidene-7-(difluoromethyl)-N-(naphthalen-1-yl)-4,5-dihydropyrazolo[1,5-a]pyrimidine-3-carboxamide | | 2.58 Method 3 |
| NCGC00182181-01 | 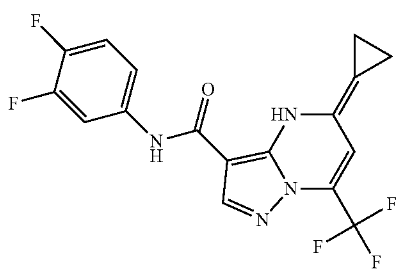 [SMILES: O=C(Nc1ccc(F)c(F)c1)c1cnn2c1NC(=C1CC1)C=C2C(F)(F)F] | 5-cyclopropylidene-N-(3,4-difluorophenyl)-7-(trifluoromethyl)-4,5-dihydropyrazolo(1,5-a]pyrimidine-3-carboxamide | | 2.56 Method 3 |
| NCGC00182183-01 | 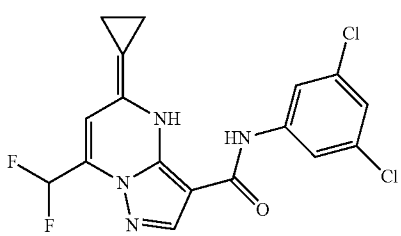 [SMILES: O=C(Nc1cc(Cl)cc(Cl)c1)c1cnn2c1NC(=C1CC1)C=C2C(F)F] | 5-cyclopropylidene-N-(3,5-dichlorophenyl)-7-(difluoromethyl)-4,5-dihydropyrazolo[1,5-a]pyrimidine-3-carboxamide | | 2.77 Method 3 |
| NCGC00182184-01 | 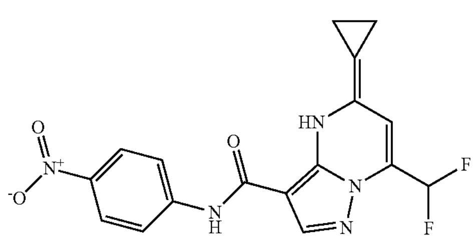 | 5-cyclopropylidene-7-(difluoromethyl)-N-(4-nitrophenyl)-4,5-dihydropyrazolo[1,5-a]pyrimidine-3-carboxamide | | 2.46 Method 3 |

-continued

| Cmpd. # | Structure | Name | AC50 | LCMS ret. time (min.) |
|---|---|---|---|---|
| NCGC00182187-01 | 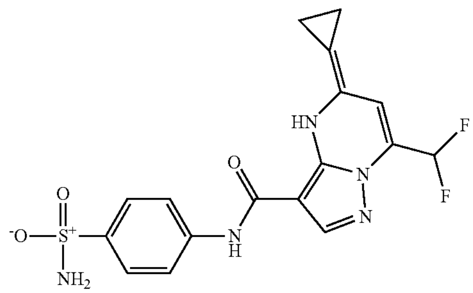 | 5-cyclopropylidene-7-(difluoromethyl)-N-(4-sulfamoylphenyl)-4,5-dihydropyrazolo[1,5-a]pyrimidine-3-carboxamide | | 2.07 Method 3 |
| NCGC00182189-01 | 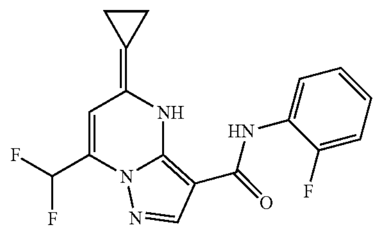 [SMILES: O=C(Nc1ccccc1F)c1cnn2c1NC(=C1CC1)C=C2C(F)F] | 5-cyclopropylidene-7-(difluoromethyl)-N-(2-fluorophenyl)-4,5-dihydropyrazolo[1,5-a]pyrimidine-3-carboxamide | | 2.52 Method 3 |
| NCGC00182191-01 | 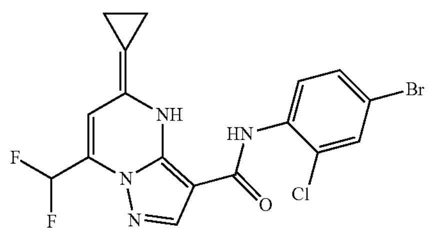 [SMILES: O=C(Nc1ccc(Br)cc1Cl)c1cnn2c1NC(=C1CC1)C=C2C(F)F] | N-(4-bromo-2-chlorophenyl)-5-cyclopropylidene-7-(difluoromethyl)-4,5-dihydropyrazolo[1,5-a]pyrimidine-3-carboxamide | | |
| NCGC00182192-01 | 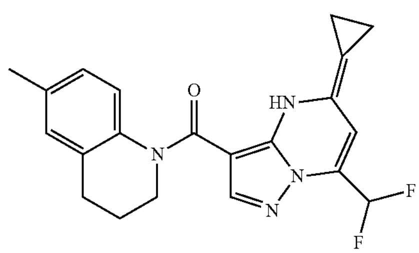 [SMILES: Cc1ccc2c(c1)CCCN2C(=O)c1cnn2c1NC(=C1CC1)C=C2C(F)F] | (5-cyclopropylidene-7-(difluoromethyl)-4,5-dihydropyrazolo[1,5-a]pyrimidin-3-yl)(6-methyl-3,4-dihydroquinolin-1(2H)-yl)methanone | | 2.49 Method 3 |
| NCGC00182193-01 | 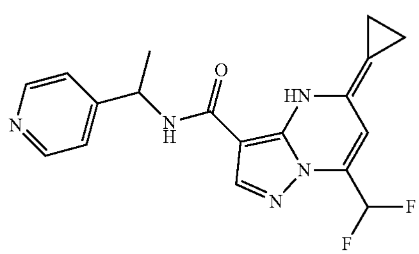 [SMILES: CC(NC(=O)c1cnn2c1NC(=C1CC1)C=C2C(F)F)c1ccncc1] | 5-cyclopropylidene-7-(difluoromethyl)-N-(1-(pyridin-4-yl)ethyl)-4,5-dihydropyrazolo[1,5-a]pyrimidine-3-carboxamide | | 1.71 Method 3 |
| NCGC00182194-01 | 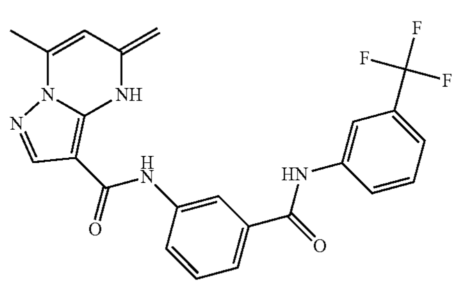 [SMILES: C=C1C=C(C)n2ncc(C(=O)Nc3cccc(C(=O)Nc4cccc(C(F)(F)F)c4)c3)c2N1] | 7-methyl-5-methylene-N-(3-(3-(trifluoromethyl)phenyl-carbamoyl)phenyl)-4,5-dihydropyrazolo[1,5-a]pyrimidine-3-carboxamide | | 2.5 Method 3 |

| Cmpd. # | Structure | Name | AC50 | LCMS ret. time (min.) |
|---|---|---|---|---|
| NCGC00182195-01 | 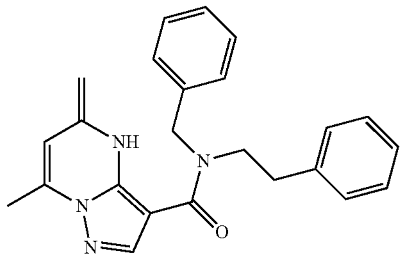 [SMILES: C=C1C=C(C)n2ncc(C(=O)N(CCc3ccccc3)Cc3ccccc3)c2N1] | N-benzyl-7-methyl-5-methylene-N-phenethyl-4,5-dihydropyrazolo[1,5-a]pyrimidine-3-carboxamide | | 2.47 Method 3 |
| NCGC00182196-01 | 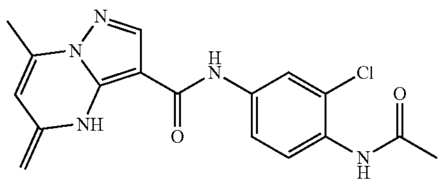 [SMILES: C=C1C=C(C)n2ncc(C(=O)Nc3ccc(NC(C)=O)c(Cl)c3)c2N1] | N-(4-acetamido-3-chlorophenyl)-7-methyl-5-methylene-4,5-dihydropyrazolo[1,5-a]pyrimidine-3-carboxamide | | 2.07 Method 3 |
| NCGC00182199-01 | 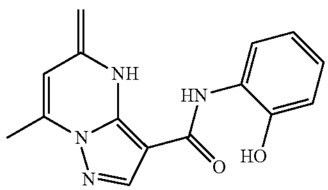 [SMILES: C=C1C=C(C)n2ncc(C(=O)Nc3ccccc3O)c2N1] | N-(2-hydroxyphenyl)-7-methyl-5-methylene-4,5-dihydropyrazolo[1,5-a]pyrimidine-3-carboxamide | | 2.07 Method 3 |
| NCGC00182200-01 | 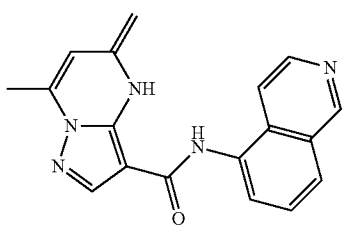 [SMILES: C=C1C=C(C)n2ncc(C(=O)Nc3cccc4cnccc34)c2N1] | N-(isoquinolin-5-yl)-7-methyl-5-methylene-4,5-dihydropyrazolo[1,5-a]pyrimidine-3-carboxamide | | 1.68 Method 3 |
| NCGC00182241-01 | 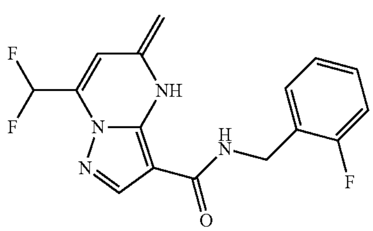 [SMILES: C=C1C=C(C(F)F)n2ncc(C(=O)NCc3ccccc3F)c2N1] | 7-(difluoromethyl)-N-(2-fluorobenzyl)-5-methylene-4,5-dihydropyrazolo[1,5-a]pyrimidine-3-carboxamide | | |
| NCGC00182242-01 | 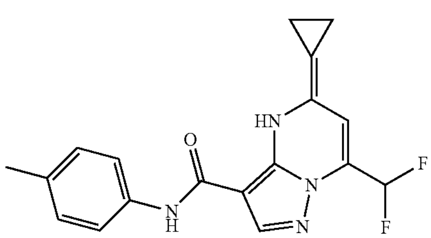 [SMILES: Cc1ccc(NC(=O)c2cnn3c2NC(=C2CC2)C=C3C(F)F)cc1] | 5-cyclopropylidene-7-(difluoromethyl)-N-p-tolyl-4,5-dihydropyrazolo[1,5-a]pyrimidine-3-carboxamide | | |

-continued

| Cmpd. # | Structure | Name | AC50 | LCMS ret. time (min.) |
|---|---|---|---|---|
| NCGC00187966-01 | 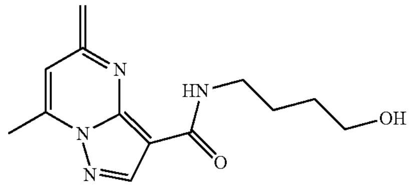 | N-(4-hydroxybutyl)-5,7-dimethylpyrazolo[1,5-a]pyrimidine-3-carboxamide | | 3.717 |
| NCGC00187968-01 | 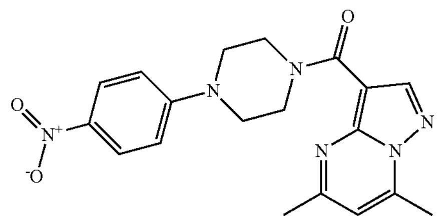 | (5,7-dimethylpyrazolo[1,5-a]pyrimidin-3-yl)(4-(4-nitrophenyl)piperazin-1-yl)methanone | | 5.079 |
| NCGC00187972-01 | 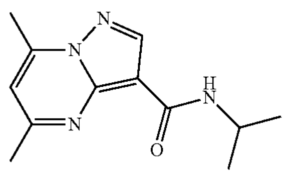 [SMILES: Cc1cc(C)n2ncc(C(=O)NC(C)C)c2n1] | N-isopropyl-5,7-dimethylpyrazolo[1,5-a]pyrimidine-3-carboxamide | | 4.655 |
| NCGC00187973-01 | 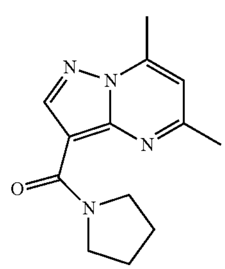 [SMILES: Cc1cc(C)n2ncc(C(=O)N3CCCC3)c2n1] | (5,7-dimethylpyrazolo[1,5-a]pyrimidin-3-yl)(pyrrolidin-1-yl)methanone | | 3.843 |
| NCGC00187974-01 | 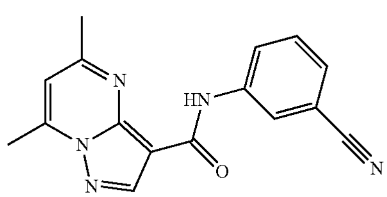 [SMILES: Cc1cc(C)n2ncc(C(=O)Nc3cccc(C#N)c3)c2n1] | N-(3-cyanophenyl)-5,7-dimethylpyrazolo[1,5-a]pyrimidine-3-carboxamide | | 5.472 |
| NCGC00187977-01 | 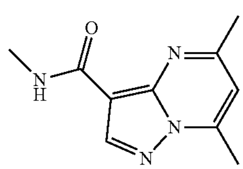 | N,5,7-trimethylpyrazolo[1,5-a]pyrimidine-3-carboxamide | | 3.709 |
| NCGC00187979-01 | 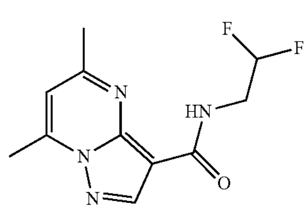 [SMILES: Cc1cc(C)n2ncc(C(=O)NCC(F)F)c2n1] | N-(2,2-difluoroethyl)-5,7-dimethylpyrazolo[1,5-a]pyrimidine-3-carboxamide | | 4.386 |

| Cmpd. # | Structure | Name | AC50 | LCMS ret. time (min.) |
|---|---|---|---|---|
| NCGC00188757-01 | 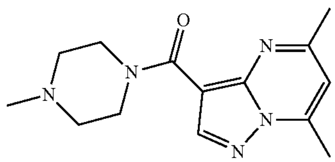 | (5,7-dimethylpyrazolo[1,5-a]pyrimidin-3-yl)(4-methylpiperazin-1-yl)methanone | | 2.543 |
| NCGC00188760-01 | 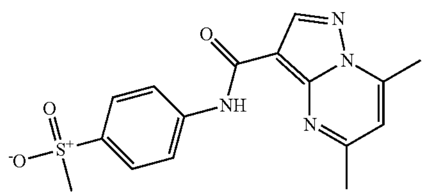 | 5,7-dimethyl-N-(4-(methylsulfonyl)phenyl)pyrazolo[1,5-a]pyrimidine-3-carboxamide | | 4.759 |
| NCGC00188761-01 | 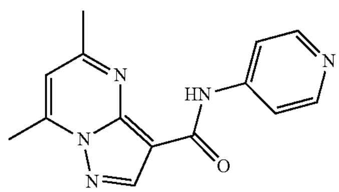 [SMILES: Cc1cc(C)n2ncc(C(=O)Nc3ccncc3)c2n1] | 5,7-dimethyl-N-(pyridin-4-yl)pyrazolo[1,5-a]pyrimidine-3-carboxamide | | 3.326 |
| NCGC00188765-01 | 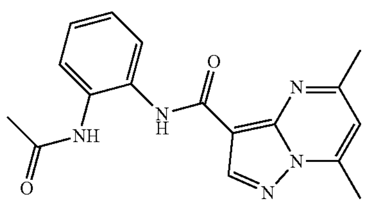 [SMILES: CC(=O)Nc1ccccc1NC(=O)c1cnn2c(C)cc(C)nc12] | N-(2-acetamidophenyl)-5,7-dimethylpyrazolo(1,5-a]pyrimidine-3-carboxamide | | 4.169 |
| NCGC00188767-01 | 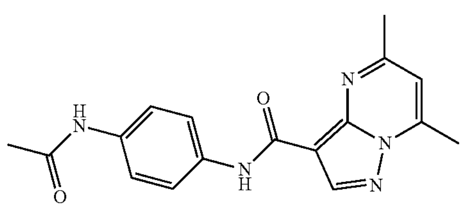 [SMILES: CC(=O)Nc1ccc(NC(=O)c2cnn3c(C)cc(C)nc23)cc1] | N-(4-acetamidophenyl)-5,7-dimethylpyrazolo[1,5-a]pyrimidine-3-carboxamide | | 4.385 |
| NCGC00188775-01 | 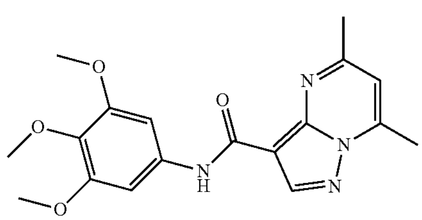 | 5,7-dimethyl-N-(3,4,5-trimethoxyphenyl)pyrazolo[1,5-a]pyrimidine-3-carboxamide | | 5.239 |
| NCGC00188777-01 | 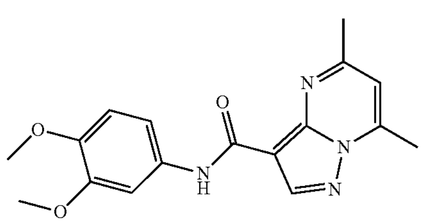 | N-(3,4-dimethoxyphenyl)-5,7-dimethylpyrazolo[1,5-a]pyrimidine-3-carboxamide | | 5.026 |

-continued

| Cmpd. # | Structure | Name | AC50 | LCMS ret. time (min.) |
|---|---|---|---|---|
| NCGC00229709-01 | 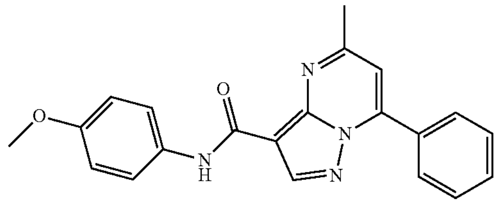 | N-(4-methoxyphenyl)-5-methyl-7-phenylpyrazolo[1,5-a]pyrimidine-3-carboxamide | | 6.165 |
| NCGC00229710-01 | 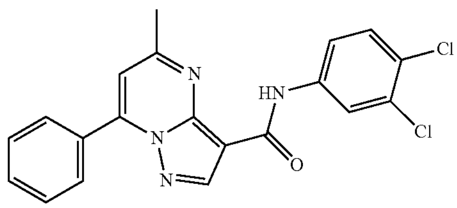 [SMILES: Cc1cc(-c2ccccc2)n2ncc(C(=O)Nc3ccc(Cl)c(Cl)c3)c2n1] | N-(3,4-dichlorophenyl)-5-methyl-7-phenylpyrazolo[1,5-a]pyrimidine-3-carboxamide | | 7.215 |
| NCGC00229720-01 | 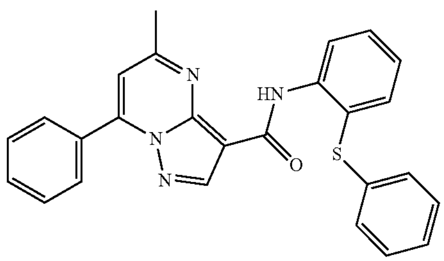 [SMILES: Cc1cc(-c2ccccc2)n2ncc(C(=O)Nc3ccccc3Sc3ccccc3)c2n1] | 5-methyl-7-phenyl-N-(2-(phenylthio)phenyl)pyrazolo[1,5-a]pyrimidine-3-carboxamide | | 7.281 |
| CCB2-5-1 | 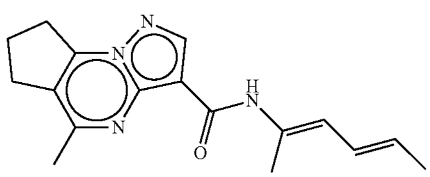 | N-((2E,4E)-hexa-2,4-dien-2-yl)-5-methyl-7,8-dihydro-6H-cyclopenta[e]pyrazolo[1,5-a]pyrimidine-3-carboxamide | | |
| CCB2-6-1 | 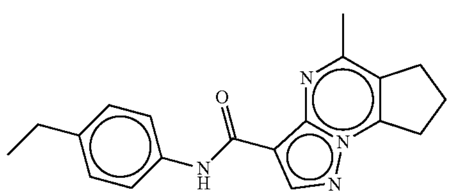 | N-(4-ethylphenyl)-5-methyl-7,8-dihydro-6H-cyclopenta[e]pyrazolo[1,5-a]pyrimidine-3-carboxamide | | |
| CCB2-7-1 | 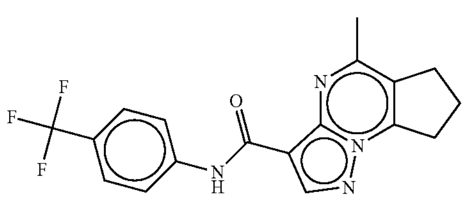 | 5-methyl-N-(4-(trifluoromethyl)phenyl)-7,8-dihydro-6H-cyclopenta[c]pyrazolo[1,5-a]pyrimidine-3-carboxamide | | |
| CGB2-8-1 | 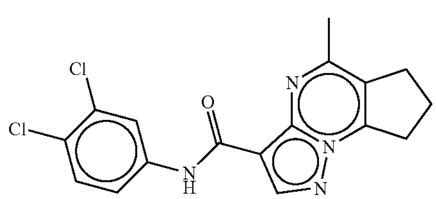 | N-(3,4-dichlorophenyl)-5-methyl-7,8-dihydro-6H-cyclopenta[c]pyrazolo[1,5-a]pyrimidine-3-carboxamide | | |

| Cmpd. # | Structure | Name | AC50 | LCMS ret. time (min.) |
|---|---|---|---|---|
| CGB2-9-1 | 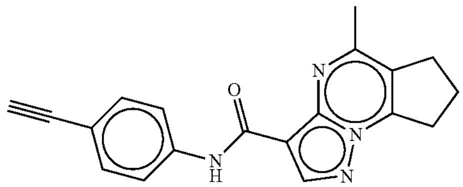 | N-(4-ethynylphenyl)-5-methyl 7,8-dihydro-6H-cyclopenta[e]pyrazolo[1,5-a]pyrimidine-3-carboxamide | | |
| CGB2-10-1 | 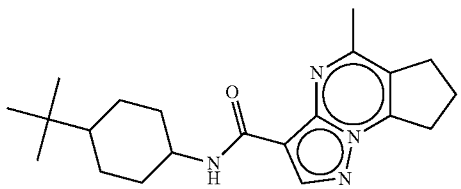 | N-(4-tert-butylcyclohexyl)-5-methyl-7,8-dihydro-6H-cyclopenta[e]pyrazolo[1,5-a]pyrimidine-3-carboxamide | | |
| CGB2-12-1 | 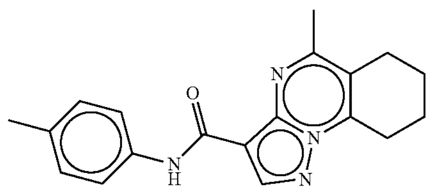 | 5-methyl-N-p-tolyl-6,7,8,9-tetrahydropyrazolo[1,5-a]quinazoline-3-carboxamide | | |
| CGB2-13-1 | 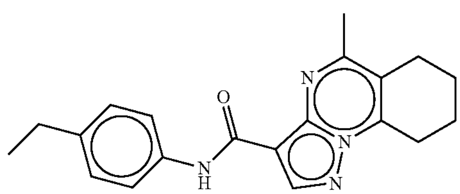 | N-(4-ethylphenyl)-5-methyl-6,7,8,9-tetrahydropyrazolo[1,5 a]quinazoline-3-carboxamide | | |
| CGB2-14-1 | 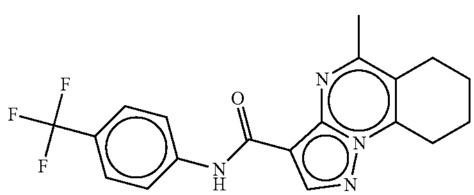 | 5-methyl-N-(4-(trifluoromethyl)phenyl)-6,7,8,9-tetrahydropyrazolo[1,5 a]quinazoline-3-carboxamide | | |
| CGB2-16-1 | 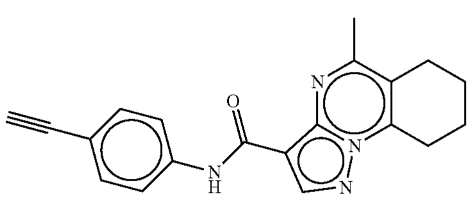 | N-(4-ethynylphenyl)-5-methyl-6,7,8,9-tetrahydropyrazolo[1,5-a]quinazoline-3-carboxamide | | |
| CGB2-17-1 | 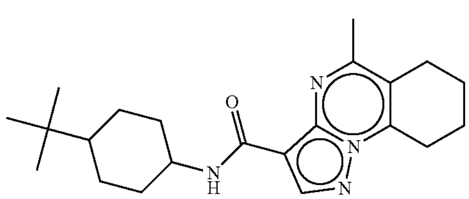 | N-(4-tert-butylcyclohexyl)-5-methyl-6,7,8,9-tetrahydropyrazolo[1,5-a]quinazoline-3-carboxamide | | |

| Cmpd. # | Structure | Name | AC50 | LCMS ret. time (min.) |
|---|---|---|---|---|
| CGB2-18-1 | 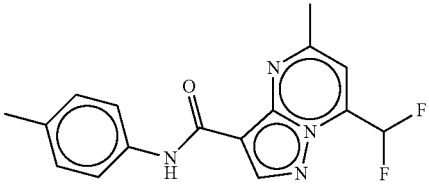 | 7-(difluoromethyl)-5-methyl-N-p-tolylpyrazolo[1,5-a]pyrimidine-3-carboxamide | | |
| CGB2-19-1 | 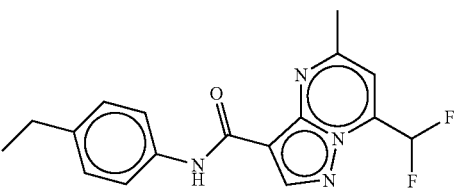 | 7-(difluoromethyl)-N-(4-ethylphenyl)-5-methylpyrazolo[1,5-a]pyrimidine-3-carboxamide | | |
| CGB2-20-1 | 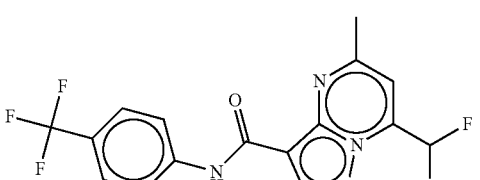 | 7-(difluoromethyl)-5-methyl-N-(4-(trifluoromethyl)phenyl)pyrazolo[1,5-a)pyrimidine-3-carboxamide | | |
| CGB2-21-1 | 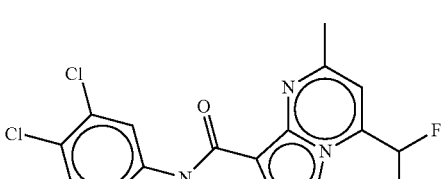 | N-(3,4-dichlorophenyl)-7-(difluoromethyl)-5-methylpyrazolo[1,5-a]pyrimidine-3-carboxamide | | |
| CGB2-22-1 | 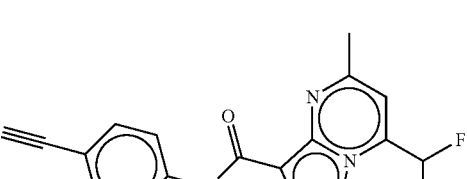 | 7-(difluoromethyl)-N-(4-ethynylphenyl)-5-methylpyrazolo[1,5-a]pyrimidine-3-carboxamide | | |
| CGB2-23-1 | 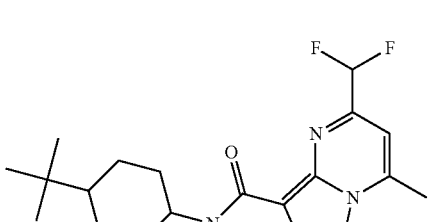 | N-(4-tert-butylcyclohexyl)-5-(difluoromethyl)-7-methylpyrazolo[1,5-a]pyrimidine-3-carboxamide | | |
| CGB2-32-1 | 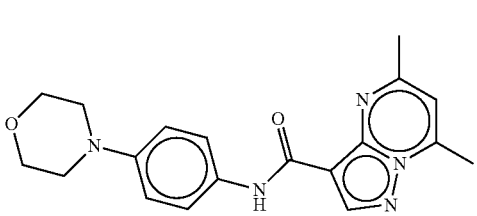 | 5,7-dimethyl-N-(4-morpholinophenyl)pyrazolo[1,5-a]pyrimidine-3-carboxamide | | |

-continued

| Cmpd. # | Structure | Name | AC50 | LCMS ret. time (min.) |
|---|---|---|---|---|
| CGB2-33-1 | 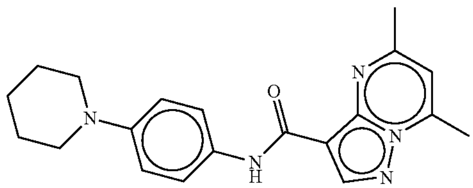 | 5,7-dimethyl-N-(4-(piperidin-1-yl)phenyl)pyrazolo[1,5-a]pyrimidine-3-carboxamide | | |
| CGB2-34-1 | 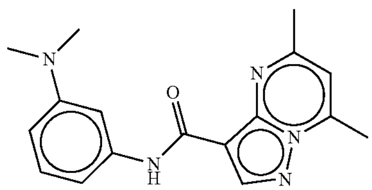 | N-(3-(dimethylamino)phenyl)-5,7-dimethylpyrazolo[1,5-a]pyrimidine-3-carboxamide | | |
| CGB2-35-1 | 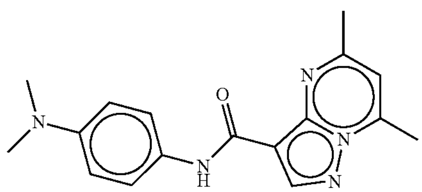 | N-(4-(dimethylamino)phenyl)-5,7-dimethylpyrazolo[1,5-a]pyrimidine-3-carboxamide | | |
| CGB2-36-1 | 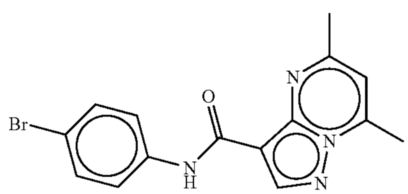 | N-(4-bromophenyl)-5,7-dimethylpyrazolo[1,5-a]pyrimidine-3-carboxamide | | |
| CGB2-39-1 | 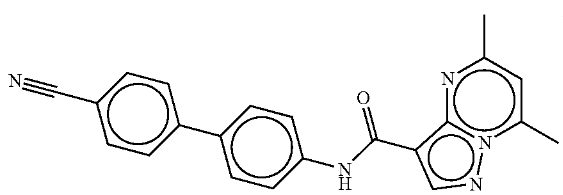 | N-(4'-cyanobiphenyl-4-yl)-5,7-dimethylpyrazolo[1,5-a]pyrimidine-3-carboxamide | | |
| CGB2-41-1 | 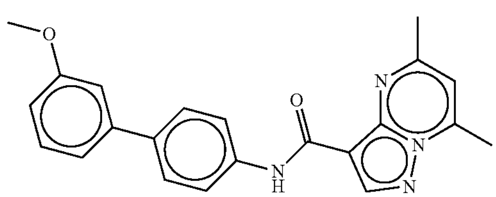 | N-(3'-methoxybiphenyl-4-yl)-5,7-dimethylpyrazolo[1,5-a]pyrimidine-3-carboxamide | | |
| CGB2-42-1 | 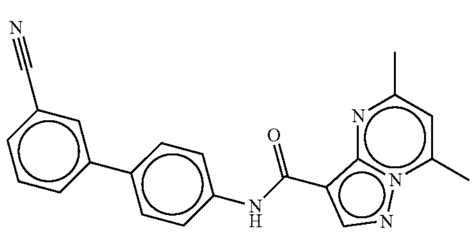 | N-(3'-cyanobiphenyl-4-yl)-5,7-dimethylpyrazolo[1,5-a]pyrimidine-3-carboxamide | | |

-continued

| Cmpd. # | Structure | Name | AC50 | LCMS ret. time (min.) |
|---|---|---|---|---|
| CGB2-43-1 | 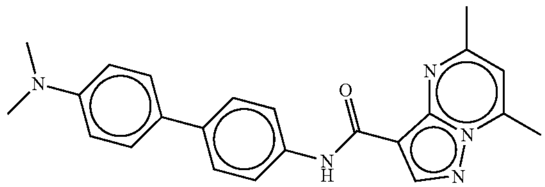 | N-(4'-(dimethylamino)biphenyl-4-yl)-5,7-dimethylpyrazolo[1,5-a]pyrimidine-3-carboxamide | | |
| CGB2-62-1 | 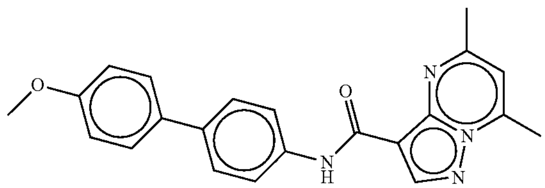 | N-(4'-methoxybiphenyl-1-yl)-5,7-dimethylpyrazolo[1,5-a]pyrimidine-3-carboxamide | | |
| CGB2-63-1 | 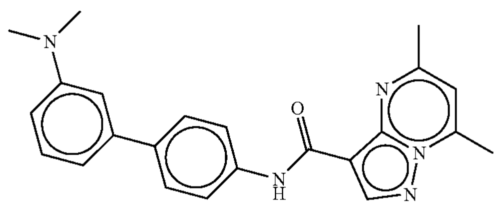 | N-(3'-(dimethylamino)biphenyl-4-yl)-5,7-dimethylpyrazolo[1,5-a]pyrimidine-3-carboxamide | | |
| CGB2-68-1 | 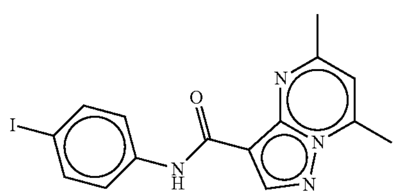 | N-(4-iodophenyl)-5,7-dimethylpyrazolo[1,5-a]pyrimidine-3-carboxamide | | |
| CGB2-55-1 | 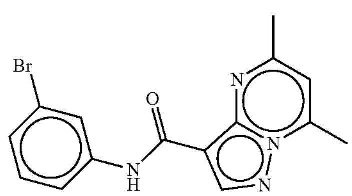 | N-(3-bromophenyl)-5,7-dimethylpyrazolo[1,5-a]pyrimidine-3-carboxamide | | |
| CGB2-56-1 | 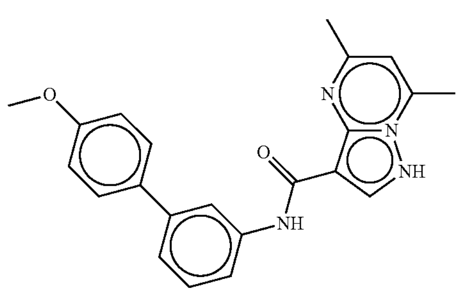 | N-(4'-methoxybiphenyl-3-yl)-5,7-dimethylpyrazolo[1,5-a]pyrimidine-3-carboxamide | | |

| Cmpd. # | Structure | Name | AC50 | LCMS ret. time (min.) |
|---|---|---|---|---|
| CGB2-57-1 | 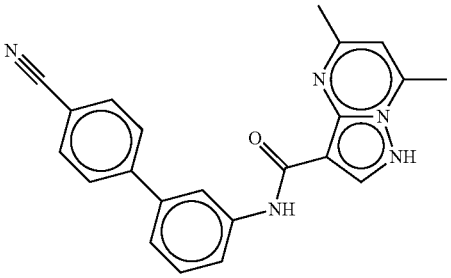 | N-(4'-cyanobiphenyl-3-yl)-5,7-dimethylpyrazolo[1,5-a]pyrimidine-3-carboxamide | | |
| CGB2-58-1 | 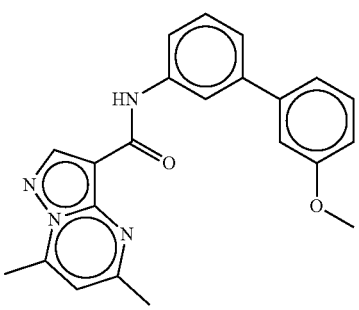 | N-(3'-methylbiphenyl-3-yl)-5,7-dimethylpyrazolo[1,5-a]pyrimidine-3-carboxamide | | |
| CGB2-59-1 | 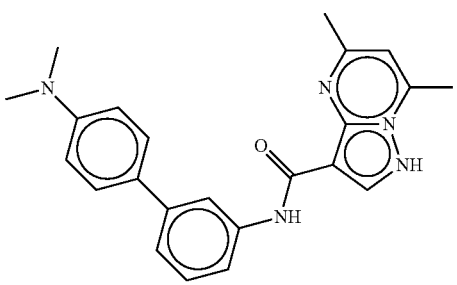 | N-(4'-(dimethylamino)biphenyl-3-yl)-5,7-dimethylpyrazolo[1,5-a]pyrimidine-3-carboxamide | | |
| CGB2-60-1 | 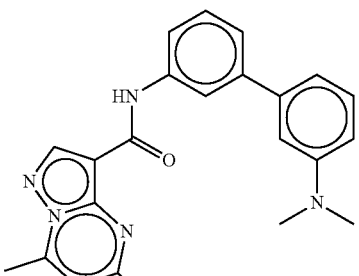 | N-(3'-(dimethylamino)biphenyl-3-yl)-5,7-dimethylpyrazolo[1,5-a]pyrimidine-3-carboxamide | | |
| CGB2-61-1 | 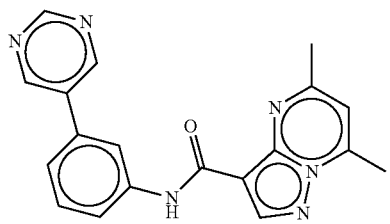 | 5,7-dimethyl-N-(3-(pyrimidin-5-yl)phenyl)pyrazolo[1,5-a]pyrimidine-3-carboxamide | | |

| Cmpd. # | Structure | Name | AC50 | LCMS ret. time (min.) |
|---|---|---|---|---|
| CGB2-67-1 | 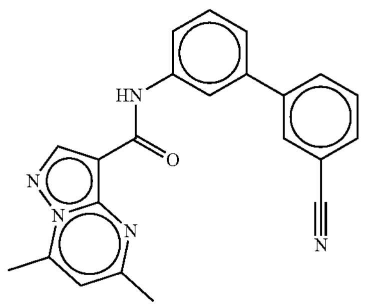 | N-(3'-cyanobiphenyl-3-yl)-5,7-dimethylpyrazolo[1,5-a]pyrimidine-3-carboxamide | | |
| CGB2-64-1 | 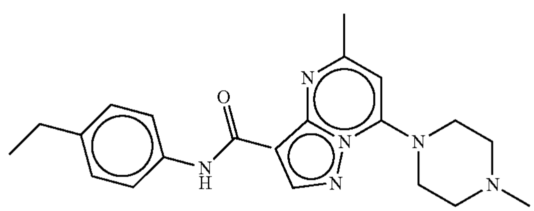 | N-(4-ethylphenyl)-5-methyl-7-(4-methylpiperazin-1-yl)pyrazolo[1,5-a]pyrimidine-3-carboxamide | | |
| CGB2-65-1 | 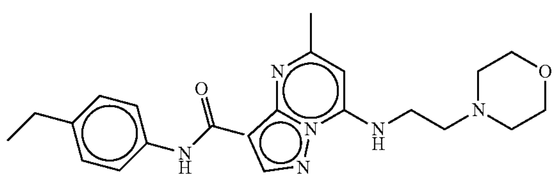 | N-(4-ethylphenyl)-5-methyl-7-(2-morpholinoethylamino)pyrazolo[1,5-a]pyrimidine-3-carboxamide | | |
| CGB2-75-1 | 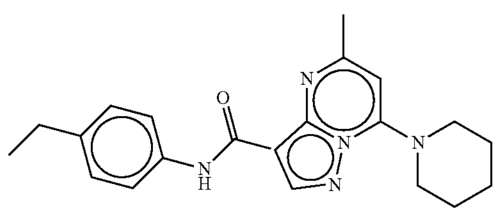 | N-(4-ethylphenyl)-5-methyl-7-(piperidin-1-yl)pyrazolo[1,5-a]pyrimidine-3-carboxamide | | |
| CGB2-77-1 | 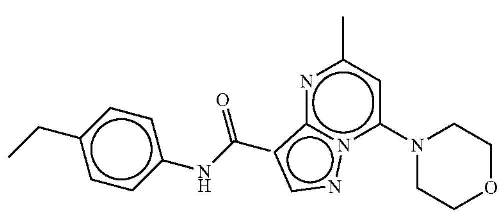 | N-(4-ethylphenyl)-5-methyl-7-morpholinopyrazolo[1,5-a]pyrimidine-3-carboxamide | | |
| CGB2-79-1 | 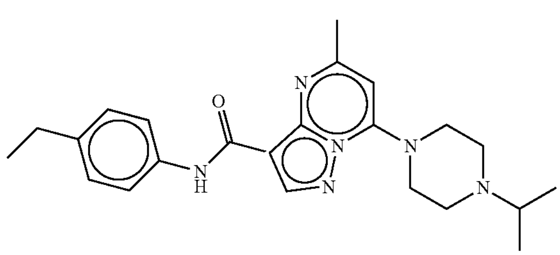 | N-(4-ethylphenyl)-7-(4-isopropylpiperazin-1-yl)-5-methylpyrazolo[1,5-a]pyrimidine-3-carboxamide | | |

| Cmpd. # | Structure | Name | AC50 | LCMS ret. time (min.) |
|---|---|---|---|---|
| CGB2-80-1 | 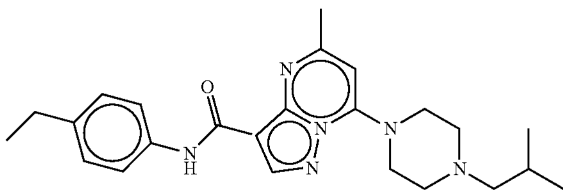 | N-(4-ethylphenyl)-7-(4-isobutylpiperazin-1-yl)-5-methylpyrazolo[1,5-a]pyrimidine-3-carboxamide | | |
| CGB2-81-1 | 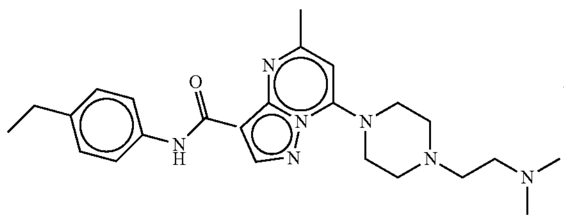 | 7-(4-(2-(dimethylamino)ethyl)piperazin-1-yl)-N-(4-ethylphenyl)-5-methylpyrazolo[1,5-a]pyrimidine-3-carboxamide | | |
| CGB2-82-1 | 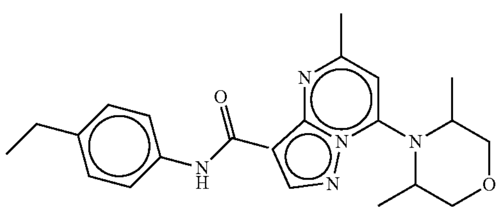 | 7-(3,5-dimethylmorpholino)-N-(4-ethylphenyl)-5-methylpyrazolo[1,5-a]pyrimidine-3-carboxamide | | |
| CGB2-83-1 | 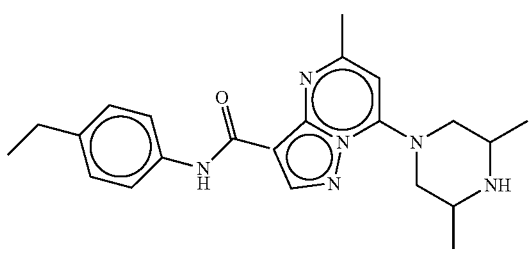 | 7-(3,5-dimethylpiperazin-1-yl)-N-(4-ethylphenyl)-5-methylpyrazolo[1,5-a]pyrimidine-3-carboxamide | | |
| CGB2-70-1 | 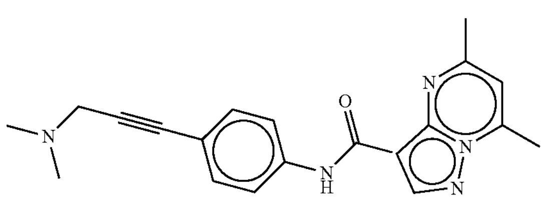 | N-(4-(3-(dimethylamino)prop-1-ynyl)phenyl)-5,7-dimethylpyrazolo[1,5-a]pyrimidine-3-carboxamide | | |

What is claimed is:

1. A method of increasing beta glucocerebrosidase activity in cells of a patient in need thereof, the method comprising providing an effective amount of a compound of Formula (I) or a pharmaceutically acceptable salt thereof to the patient, wherein Formula (I) is:

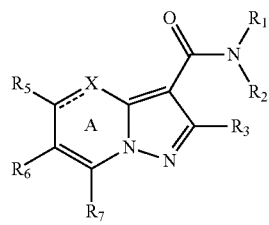

Formula (I)

wherein the ring

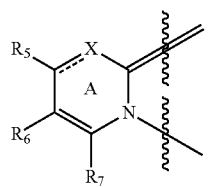

is a ring system of the formula
(i)

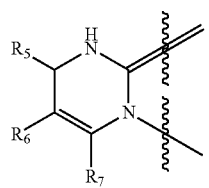

in which $R_5$ is an optionally substituted alkylidene group and $R_6$ and $R_7$ carry the definitions set forth below, or
(ii)

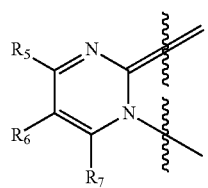

in which $R_5$, $R_6$, and $R_7$ carry the definitions set forth below;

$R_1$ is $C_1$-$C_6$alkyl, $C_2$-$C_6$alkenyl, $C_2$-$C_6$alkynyl, (mono- or bicyclic carbocycle)$C_0$-$C_4$alkyl or (mono- or bicyclic heterocycle)$C_0$-$C_4$alkyl, each of which $R_1$ is unsubstituted or substituted with one or more substituents independently chosen from halogen, hydroxyl, cyano, nitro, amino, —CHO, —COOH, $C_1$-$C_6$alkyl, $C_2$-$C_6$alkenyl, $C_2$-$C_6$alkynyl, $C_1$-$C_6$alkoxy, $C_2$-$C_6$alkanoyl, (mono- or di-$C_1$-$C_6$alkylamino)$C_0$-$C_4$alkyl, mono- or di-$C_1$-$C_6$alkylcarboxamide, $C_1$-$C_6$alkylester, $C_1$-$C_6$alkylthio, $C_1$-$C_6$alkylsulfonyl, $C_1$-$C_2$haloalkyl, and $C_1$-$C_2$haloalkoxy, and with 0 or 1 substituents chosen from Y—Z— where Z is a covalent bond, $C_1$-$C_4$alkylene, $C_2$-$C_4$alkenylene, $C_2$-$C_4$alkynylene, —S—, —O—, —NR—, —C(O)—, —NHC(O)—, or —C(O)NH—, where R is hydrogen or $C_1$-$C_4$alkyl, and Y is phenyl, pyrimidinyl, 5- or 6-membered heterocycloalkyl, or pyridyl, each of which is unsubstituted or substituted with 1 to 3 substituents independently chosen from halogen, hydroxyl, cyano, nitro, amino, $C_1$-$C_4$alkyl, $C_1$-$C_4$alkoxy, mono- or di-$C_1$-$C_4$alkylamino, trifluoromethyl, difluoromethyl, trifluoromethoxy, and phenyl; and $R_2$ is hydrogen, $C_1$-$C_6$alkyl, $C_3$-$C_7$cycloalkyl, (phenyl)$C_0$-$C_2$alkyl; or $R_1$ and $R_2$ are joined to form a 5- to 7-membered heterocycloalkyl ring having 0 or 1 additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$alkyl, and $C_1$-$C_2$alkoxy;

$R_3$ is hydrogen or $C_1$-$C_2$alkyl;

$R_5$ is halogen, hydroxyl, amino, cyano, $C_1$-$C_4$alkyl, vinyl, cyclopropyl, cyclopropylidenyl, $C_1$-$C_4$alkoxy, difluoromethyl, trifluoromethyl, or phenyl;

$R_6$ is hydrogen, halogen, hydroxyl, $C_1$-$C_4$alkyl, or $C_1$-$C_4$alkoxy; and $R_7$ is halogen, hydroxyl, amino, cyano, $C_1$-$C_4$alkyl, $C_1$-$C_4$alkoxy, difluoromethyl, trifluoromethyl, or $R_7$ is phenyl or a 5- to 7-membered heterocycloalkyl ring having 1 or 2 heteroatoms chosen from N, O, and S, each of which $R_7$ is directly attached via a covalent bond or attached via a $C_1$-$C_4$ alkyl, $C_1$-$C_4$alkoxy, or $C_1$-$C_4$alkylamino group, and each of which $R_7$ is unsubstituted or substituted with 1 to 3 substituents independently chosen from halogen, hydroxyl, $C_1$-$C_4$alkyl, $C_1$-$C_4$alkoxy, (mono- and di-$C_1$-$C_2$alkylamino)$C_0$-$C_4$alkyl, $C_1$-$C_2$haloalkyl, and $C_1$-$C_2$haloalkoxy; or $R_6$ and $R_7$ are taken together to form a 5- or 6-membered carbocyclic ring with no additional points of unsaturation, which ring is unsubstituted or substituted with 1 to 3 substituents independently chosen from $C_1$-$C_2$alkyl and $C_1$-$C_2$alkoxy.

2. The method of claim 1, wherein $R_6$ is hydrogen.

3. The method of claim 2, wherein the compound is a compound of the formula

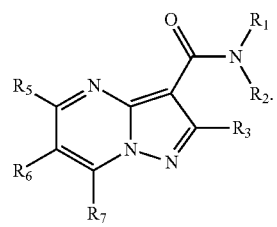

4. The method of claim 2, wherein the compound is a compound of the formula

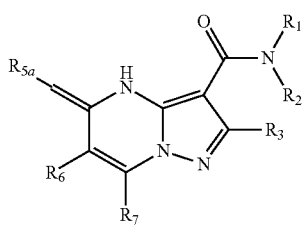

where R$_{5a}$ is hydrogen, C$_1$-C$_4$alkyl, C$_3$-C$_7$cycloalkyl, or 4- to 7-membered carbon-attached heterocycloalkyl, having 1 or 2 heteroatoms independently chosen from N, S, and O.

5. The method of claim 3, wherein
R$_2$ is hydrogen or methyl;
R$_5$ is C$_1$-C$_4$alkyl or difluoromethyl; and
R$_7$ is C$_1$-C$_4$alkyl, difluoromethyl, or phenyl.

6. The method of claim 3, wherein
R$_5$ and R$_7$ are both methyl; or
R$_5$ is methyl and R$_7$ is phenyl; or
one of R$_5$ and R$_7$ is methyl and the other is difluoromethyl.

7. The method of claim 6, wherein
R$_1$ is phenyl, cyclohexyl, naphthyl, tetrahydronaphthyl, or dihydroindenyl,
each of which is unsubstituted or substituted with one or more substituents independently chosen from halogen, hydroxyl, cyano, nitro, amino, —CHO, —COOH, C$_1$-C$_6$alkyl, C$_2$-C$_6$alkanoyl, mono- or di-C$_1$-C$_6$alkylamino, mono- or di-C$_1$-C$_6$alkylcarboxamide, C$_1$-C$_6$alkylthio, C$_1$-C$_6$alkylsulfonyl, C$_1$-C$_2$haloalkyl, and C$_1$-C$_2$haloalkoxy, and with 0 or 1 substituents chosen from Y—Z— where Z is a covalent bond, C$_1$-C$_4$alkylene, —S—, —O—, —NR—, —C(O)—, —NHC(O)—, or —C(O)NH—, where R is hydrogen or C$_1$-C$_4$alkyl, and Y is phenyl or pyridyl, each of which is unsubstituted or substituted with 1 to 3 substituents independently chosen from halogen, hydroxyl, cyano, nitro, amino, C$_1$-C$_4$alkyl, and C$_1$-C$_4$alkoxy.

8. The method of claim 6, wherein
R$_1$ is phenyl, substituted with at least one substituent chosen from cyano, trifluoromethyl, and CH$_3$C(O)NH—, or
R$_1$ is cyclohexyl, substituted with at least one trifluoromethyl, or C$_3$-C$_6$alkyl; or
R$_1$ is dihydroindenyl, substituted with one or more substituents independently chosen from halogen, hydroxyl, cyano, nitro, amino, —CHO, —COOH, C$_1$-C$_4$alkyl, C$_2$-C$_4$alkanoyl, mono- or di-C$_1$-C$_4$alkylamino, C$_1$-C$_2$haloalkyl, and C$_1$-C$_2$haloalkoxy.

9. The method of claim 1, wherein the compound is
N-(4-ethynylphenyl)-5,7-dimethylpyrazolo[1,5-a]pyrimidine-3-carboxamide;
N-(4-bromophenyl)-5,7-dimethylpyrazolo[1,5-a]pyrimidine-3-carboxamide;
N-(4-bromo-2-fluorophenyl)-5-cyclopropylidene-7-(difluoromethyl)-4,5-dihydropyrazolo[1,5-a]pyrimidine-3-carboxamide;
5-cyclopropylidene-7-(difluoromethyl)-N-(3,4-dimethylphenyl)-4,5-dihydropyrazolo[1,5-a]pyrimidine-3-carboxamide;
5-cyclopropylidene-7-(difluoromethyl)-N-(2,5-difluorophenyl)-4,5-dihydropyrazolo[1,5-a]pyrimidine-3-carboxamide;
5-cyclopropylidene-7-(difluoromethyl)-N-(2,3-dihydro-1H-inden-5-yl)-4,5-dihydropyrazolo[1,5-a]pyrimidine-3-carboxamide;
N-(4-tert-butylcyclohexyl)-5,7-dimethylpyrazolo[1,5-a]pyrimidine-3-carboxamide;
N-(4-tert-butylcyclohexyl)-5-methyl-7-phenylpyrazolo[1,5-a]pyrimidine-3-carboxamide;
5-cyclopropylidene-7-(difluoromethyl)-N-(2-(phenylthio)phenyl)-4,5-dihydropyrazolo[1,5-a]pyrimidine-3-carboxamide;
7-(difluoromethyl)-N-(3-ethylphenyl)-5-methylene-4,5-dihydropyrazolo[1,5-a]pyrimidine-3-carboxamide;
N-(4-tert-butylcyclohexyl)-5-cyclopropylidene-7-(difluoromethyl)-4,5-dihydropyrazolo[1,5-a]pyrimidine-3-carboxamide;
N-(4-(diethylamino)phenyl)-7-(difluoromethyl)-5-methylene-4,5-dihydropyrazolo[1,5-a]pyrimidine-3-carboxamide;
N-cyclohexyl-5-cyclopropylidene-7-(difluoromethyl)-4,5-dihydropyrazolo[1,5-a]pyrimidine-3-carboxamide;
5-cyclopropylidene-7-(difluoromethyl)-N-(3-(phenylamino)phenyl)-4,5-dihydropyrazolo[1,5-a]pyrimidine-3-carboxamide;
N-(2-bromophenyl)-5-cyclopropylidene-7-(difluoromethyl)-4,5-dihydropyrazolo[1,5-a]pyrimidine-3-carboxamide;
5-cyclopropylidene-7-(difluoromethyl)-N-(2-(phenylthio)phenyl)-4,5-dihydropyrazolo[1,5-a]pyrimidine-3-carboxamide;
5-cyclopropylidene-N-(2-(phenylthio)phenyl)-7-(trifluoromethyl)-4,5-dihydropyrazolo[1,5-a]pyrimidine-3-carboxamide;
5-cyclopropylidene-7-(difluoromethyl)-N-(1,2,3,4-tetrahydronaphthalen-1-yl)-4,5-dihydropyrazolo[1,5-a]pyrimidine-3-carboxamide;
5,7-dimethyl-N-(2-(phenylthio)phenyl)pyrazolo[1,5-a]pyrimidine-3-carboxamide;
N-(4-cyanophenyl)-5,7-dimethylpyrazolo[1,5-a]pyrimidine-3-carboxamide;
N-(4-tert-butylcyclohexyl)-5,7-dimethylpyrazolo[1,5-a]pyrimidine-3-carboxamide;
N,N-dicyclohexyl-5-cyclopropylidene-7-(difluoromethyl)-4,5-dihydropyrazolo[1,5-a]pyrimidine-3-carboxamide;
N-(4-bromophenyl)-5-cyclopropylidene-7-(difluoromethyl)-4,5-dihydropyrazolo[1,5-a]pyrimidine-3-carboxamide;
5-cyclopropylidene-N-(2,4-dichlorophenyl)-7-(difluoromethyl)-4,5-dihydropyrazolo[1,5-a]pyrimidine-3-carboxamide;
N-(4-acetylphenyl)-5-cyclopropylidene-7-(difluoromethyl)-4,5-dihydropyrazolo[1,5-a]pyrimidine-3-carboxamide;
N-(4-chlorophenyl)-5-cyclopropylidene-7-(difluoromethyl)-4,5-dihydropyrazolo[1,5-a]pyrimidine-3-carboxamide;
N-(4-bromo-2-(trifluoromethyl)phenyl)-7-(difluoromethyl)-5-methylene-4,5-dihydropyrazolo[1,5-a]pyrimidine-3-carboxamide;
5-cyclopropylidene-7-(difluoromethyl)-N-(3,4-difluorophenyl)-4,5-dihydropyrazolo[1,5-a]pyrimidine-3-carboxamide;
5-cyclopropylidene-7-(difluoromethyl)-N-(naphthalen-1-yl)-4,5-dihydropyrazolo[1,5-a]pyrimidine-3-carboxamide;

5-cyclopropylidene-N-(3,4-difluorophenyl)-7-(trifluoromethyl)-4,5-dihydropyrazolo[1,5-a]pyrimidine-3-carboxamide;
5-cyclopropylidene-N-(3,5-dichlorophenyl)-7-(difluoromethyl)-4,5-dihydropyrazolo[1,5-a]pyrimidine-3-carboxamide;
5-cyclopropylidene-7-(difluoromethyl)-N-(4-nitrophenyl)-4,5-dihydropyrazolo[1,5-a]pyrimidine-3-carboxamide;
5-cyclopropylidene-7-(difluoromethyl)-N-(2-fluorophenyl)-4,5-dihydropyrazolo[1,5-a]pyrimidine-3-carboxamide;
N-(4-bromo-2-chlorophenyl)-5-cyclopropylidene-7-(difluoromethyl)-4,5-dihydropyrazolo[1,5-a]pyrimidine-3-carboxamide;
7-methyl-5-methylene-N-(3-(3-(trifluoromethyl)phenylcarbamoyl)phenyl)-4,5-dihydropyrazolo[1,5-a]pyrimidine-3-carboxamide;
N-(4-acetamido-3-chlorophenyl)-7-methyl-5-methylene-4,5-dihydropyrazolo[1,5-a]pyrimidine-3-carboxamide;
N-(2-hydroxyphenyl)-7-methyl-5-methylene-4,5-dihydropyrazolo[1,5-a]pyrimidine-3-carboxamide;
5-cyclopropylidene-7-(difluoromethyl)-N-p-tolyl-4,5-dihydropyrazolo[1,5-a]pyrimidine-3-carboxamide;
N-(3-cyanophenyl)-5,7-dimethylpyrazolo[1,5-a]pyrimidine-3-carboxamide;
5,7-dimethyl-N-(4-(methylsulfonyl)phenyl)pyrazolo[1,5-a]pyrimidine-3-carboxamide;
N-(2-acetamidophenyl)-5,7-dimethylpyrazolo[1,5-a]pyrimidine-3-carboxamide;
N-(4-acetamidophenyl)-5,7-dimethylpyrazolo[1,5-a]pyrimidine-3-carboxamide;
5-methyl-7-phenyl-N-(2-(phenylthio)phenyl)pyrazolo[1,5-a]pyrimidine-3-carboxamide;
N-(4-ethylphenyl)-5-methyl-7,8-dihydro-6H-cyclopenta[e]pyrazolo[1,5-a]pyrimidine-3-carboxamide;
5-methyl-N-(4-(trifluoromethyl)phenyl)-7,8-dihydro-6H-cyclopenta[e]pyrazolo[1,5-a]pyrimidine-3-carboxamide;
N-(3,4-dichlorophenyl)-5-methyl-7,8-dihydro-6H-cyclopenta[e]pyrazolo[1,5-a]pyrimidine-3-carboxamide;
N-(4-ethynylphenyl)-5-methyl-7,8-dihydro-6H-cyclopenta[e]pyrazolo[1,5-a]pyrimidine-3-carboxamide;
N-(4-tert-butylcyclohexyl)-5-methyl-7,8-dihydro-6H-cyclopenta[e]pyrazolo[1,5-a]pyrimidine-3-carboxamide;
5-methyl-N-p-tolyl-6,7,8,9-tetrahydropyrazolo[1,5-a]quinazoline-3-carboxamide;
N-(4-ethylphenyl)-5-methyl-6,7,8,9-tetrahydropyrazolo[1,5-a]quinazoline-3-carboxamide;
5-methyl-N-(4-(trifluoromethyl)phenyl)-6,7,8,9-tetrahydropyrazolo[1,5-a]quinazoline-3-carboxamide;
N-(4-ethynylphenyl)-5-methyl-6,7,8,9-tetrahydropyrazolo[1,5-a]quinazoline-3-carboxamide;
N-(4-tert-butylcyclohexyl)-5-methyl-6,7,8,9-tetrahydropyrazolo[1,5-a]quinazoline-3-carboxamide;
7-(difluoromethyl)-5-methyl-N-p-tolylpyrazolo[1,5-a]pyrimidine-3-carboxamide;
7-(difluoromethyl)-5-methyl-N-(4-(trifluoromethyl)phenyl)pyrazolo[1,5-a]pyrimidine-3-carboxamide;
N-(3,4-dichlorophenyl)-7-(difluoromethyl)-5-methylpyrazolo[1,5-a]pyrimidine-3-carboxamide;
7-(difluoromethyl)-N-(4-ethynylphenyl)-5-methylpyrazolo[1,5-a]pyrimidine-3-carboxamide;
N-(4-tert-butylcyclohexyl)-5-(difluoromethyl)-7-methylpyrazolo[1,5-a]pyrimidine-3-carboxamide;
5,7-dimethyl-N-(4-(piperidin-1-yl)phenyl)pyrazolo[1,5-a]pyrimidine-3-carboxamide;
N-(3-(dimethylamino)phenyl)-5,7-dimethylpyrazolo[1,5-a]pyrimidine-3-carboxamide;
N-(4-(dimethylamino)phenyl)-5,7-dimethylpyrazolo[1,5-a]pyrimidine-3-carboxamide;
N-(4-bromophenyl)-5,7-dimethylpyrazolo[1,5-a]pyrimidine-3-carboxamide;
N-(4'-cyanobiphenyl-4-yl)-5,7-dimethylpyrazolo[1,5-a]pyrimidine-3-carboxamide;
N-(3'-methoxybiphenyl-4-yl)-5,7-dimethylpyrazolo[1,5-a]pyrimidine-3-carboxamide;
N-(3'-cyanobiphenyl-4-yl)-5,7-dimethylpyrazolo[1,5-a]pyrimidine-3-carboxamide;
N-(4'-(dimethylamino)biphenyl-4-yl)-5,7-dimethylpyrazolo[1,5-a]pyrimidine-3-carboxamide;
N-(4'-methoxybiphenyl-4-yl)-5,7-dimethylpyrazolo[1,5-a]pyrimidine-3-carboxamide;
N-(3'-(dimethylamino)biphenyl-4-yl)-5,7-dimethylpyrazolo[1,5-a]pyrimidine-3-carboxamide;
N-(4-iodophenyl)-5,7-dimethylpyrazolo[1,5-a]pyrimidine-3-carboxamide;
N-(3-bromophenyl)-5,7-dimethylpyrazolo[1,5-a]pyrimidine-3-carboxamide;
N-(4'-methoxybiphenyl-3-yl)-5,7-dimethylpyrazolo[1,5-a]pyrimidine-3-carboxamide;
N-(4'-cyanobiphenyl-3-yl)-5,7-dimethylpyrazolo[1,5-a]pyrimidine-3-carboxamide;
N-(3'-methoxybiphenyl-3-yl)-5,7-dimethylpyrazolo[1,5-a]pyrimidine-3-carboxamide;
N-(4'-(dimethylamino)biphenyl-3-yl)-5,7-dimethylpyrazolo[1,5-a]pyrimidine-3-carboxamide;
N-(3'-(dimethylamino)biphenyl-3-yl)-5,7-dimethylpyrazolo[1,5-a]pyrimidine-3-carboxamide;
5,7-dimethyl-N-(3-(pyrimidin-5-yl)phenyl)pyrazolo[1,5-a]pyrimidine-3-carboxamide;
N-(3'-cyanobiphenyl-3-yl)-5,7-dimethylpyrazolo[1,5-a]pyrimidine-3-carboxamide;
N-(4-ethylphenyl)-5-methyl-7-(4-methylpiperazin-1-yl)pyrazolo[1,5-a]pyrimidine-3-carboxamide;
N-(4-ethylphenyl)-5-methyl-7-(2-morpholinoethylamino)pyrazolo[1,5-a]pyrimidine-3-carboxamide;
N-(4-ethylphenyl)-5-methyl-7-(piperidin-1-yl)pyrazolo[1,5-a]pyrimidine-3-carboxamide;
N-(4-ethylphenyl)-5-methyl-7-morpholinopyrazolo[1,5-a]pyrimidine-3-carboxamide;
N-(4-ethylphenyl)-7-(4-isopropylpiperazin-1-yl)-5-methylpyrazolo[1,5-a]pyrimidine-3-carboxamide;
N-(4-ethylphenyl)-7-(4-isobutylpiperazin-1-yl)-5-methylpyrazolo[1,5-a]pyrimidine-3-carboxamide;
7-(4-(2-(dimethylamino)ethyl)piperazin-1-yl)-N-(4-ethylphenyl)-5-methylpyrazolo[1,5-a]pyrimidine-3-carboxamide;
7-(3,5-dimethylmorpholino)-N-(4-ethylphenyl)-5-methylpyrazolo[1,5-a]pyrimidine-3-carboxamide; or 7-(3,5-dimethylpiperazin-1-yl)-N-(4-ethylphenyl)-5-methylpyrazolo[1,5-a]pyrimidine-3-carboxamide; or a pharmaceutically acceptable salt of the compound salts thereof.

10. The method of claim 9, wherein the compound is N-(4-ethynylphenyl)-5,7-dimethylpyrazolo[1,5-a]pyrimidine-3-carboxamide (NCGC00188758-01);
N-(4-ethylphenyl)-5-methyl-7-(4-methylpiperazin-1-yl)pyrazolo[1,5-a]pyrimidine-3-carboxamide (CGB2-64-1);
N-(4-ethylphenyl)-5-methyl-7-(2-morpholinoethylamino)pyrazolo[1,5-a]pyrimidine-3-carboxamide (CGB2-65-1);

((N-(4-ethylphenyl)-5-methyl-7-(piperidin-1-yl)pyrazolo[1,5-a]pyrimidine-3-carboxamide (CGB2-75-1);

N-(4-ethylphenyl)-5-methyl-7-morpholinopyrazolo[1,5-a]pyrimidine-3-carboxamide (CGB2-77-1);

N-(4-ethylphenyl)-7-(4-isopropylpiperazin-1-yl)-5-methylpyrazolo[1,5-a]pyrimidine-3-carboxamide (CGB2-79-1);

N-(4-ethylphenyl)-7-(4-isobutylpiperazin-1-yl)-5-methylpyrazolo[1,5-a]pyrimidine-3-carboxamide (CGB2-80-1);

7-(4-(2-(dimethylamino)ethyl)piperazin-1-yl)-N-(4-ethylphenyl)-5-methylpyrazolo[1,5-a]pyrimidine-3-carboxamide (CGB2-81-1);

7-(3,5-dimethylmorpholino)-N-(4-ethylphenyl)-5-methylpyrazolo[1,5-a]pyrimidine-3-carboxamide (CGB2-82-1); or 7-(3,5-dimethylpiperazin-1-yl)-N-(4-ethylphenyl)-5-methylpyrazolo[1,5-a]pyrimidine-3-carboxamide (CGB2-83-1); or a pharmaceutically acceptable salt of the compounds.

11. A method of treating or preventing the symptoms of Gaucher disease in a patient in need thereof, the method comprising providing an effective amount of a compound or a pharmaceutically acceptable salt thereof to the patient, wherein the compound is N-(4-ethynylphenyl)-5,7-dimethylpyrazolo[1,5-a]pyrimidine-3-carboxamide;

N-(4-bromophenyl)-5,7-dimethylpyrazolo[1,5-a]pyrimidine-3-carboxamide;

N-(4-bromo-2-fluorophenyl)-5-cyclopropylidene-7-(difluoromethyl)-4,5-dihydropyrazolo[1,5-a]pyrimidine-3-carboxamide;

5-cyclopropylidene-7-(difluoromethyl)-N-(3,4-dimethylphenyl)-4,5-dihydropyrazolo[1,5-a]pyrimidine-3-carboxamide;

5-cyclopropylidene-7-(difluoromethyl)-N-(2,5-difluorophenyl)-4,5-dihydropyrazolo[1,5-a]pyrimidine-3-carboxamide;

5-cyclopropylidene-7-(difluoromethyl)-N-(2,3-dihydro-1H-inden-5-yl)-4,5-dihydropyrazolo[1,5-a]pyrimidine-3-carboxamide;

N-(4-tert-butylcyclohexyl)-5,7-dimethylpyrazolo[1,5-a]pyrimidine-3-carboxamide;

N-(4-tert-butylcyclohexyl)-5-methyl-7-phenylpyrazolo[1,5-a]pyrimidine-3-carboxamide;

5-cyclopropylidene-7-(difluoromethyl)-N-(2-(phenylthio)phenyl)-4,5-dihydropyrazolo[1,5-a ]pyrimidine-3-carboxamide;

7-(difluoromethyl)-N-(3-ethylphenyl)-5-methylene-4,5-dihydropyrazolo[1,5-a]pyrimidine-3-carboxamide;

N-(4-tert-butylcyclohexyl)-5-cyclopropylidene-7-(difluoromethyl)-4,5-dihydropyrazolo[1,5-a ]pyrimidine-3-carboxamide;

N-(4-(diethylamino)phenyl)-7-(difluoromethyl)-5-methylene-4,5-dihydropyrazolo[1,5-a ]pyrimidine-3-carboxamide;

N-cyclohexyl-5-cyclopropylidene-7-(difluoromethyl)-4,5-dihydropyrazolo[1,5-a]pyrimidine-3-carboxamide;

5-cyclopropylidene-7-(difluoromethyl)-N-(3-(phenylamino)phenyl)-4,5-dihydropyrazolo[1,5-a ]pyrimidine-3-carboxamide;

N-(2-bromophenyl)-5-cyclopropylidene-7-(difluoromethyl)-4,5-dihydropyrazolo[1,5-a ]pyrimidine-3-carboxamide;

5-cyclopropylidene-7-(difluoromethyl)-N-(2-(phenylthio)phenyl)-4,5-dihydropyrazolo[1,5-a ]pyrimidine-3-carboxamide;

5-cyclopropylidene-N-(2-(phenylthio)phenyl)-7-(trifluoromethyl)-4,5-dihydropyrazolo[1,5-a ]pyrimidine-3-carboxamide;

5-cyclopropylidene-7-(difluoromethyl)-N-(1,2,3,4-tetrahydronaphthalen-1-yl)-4,5-dihydropyrazolo[1,5-a]pyrimidine-3-carboxamide;

5,7-dimethyl-N-(2-(phenylthio)phenyl)pyrazolo[1,5-a]pyrimidine-3-carboxamide;

N-(4-cyanophenyl)-5,7-dimethylpyrazolo[1,5-a]pyrimidine-3-carboxamide;

N-(4-tert-butylcyclohexyl)-5,7-dimethylpyrazolo[1,5-a]pyrimidine-3-carboxamide;

N,N-dicyclohexyl-5-cyclopropylidene-7-(difluoromethyl)-4,5-dihydropyrazolo[1,5-a ]pyrimidine-3-carboxamide;

N-(4-bromophenyl)-5-cyclopropylidene-7-(difluoromethyl)-4,5-dihydropyrazolo[1,5-a]pyrimidine-3-carboxamide;

5-cyclopropylidene-N-(2,4-dichlorophenyl)-7-(difluoromethyl)-4,5-dihydropyrazolo[1,5-a]pyrimidine-3-carboxamide;

N-(4-acetylphenyl)-5-cyclopropylidene-7-(difluoromethyl)-4,5-dihydropyrazolo[1,5-a]pyrimidine-3-carboxamide;

N-(4-chlorophenyl)-5-cyclopropylidene-7-(difluoromethyl)-4,5-dihydropyrazolo[1,5-a]pyrimidine-3-carboxamide;

N-(4-bromo-2-(trifluoromethyl)phenyl)-7-(difluoromethyl)-5-methylene-4,5-dihydropyrazolo[1,5-a]pyrimidine-3-carboxamide;

5-cyclopropylidene-7-(difluoromethyl)-N-(3,4-difluorophenyl)-4,5-dihydropyrazolo[1,5-a]pyrimidine-3-carboxamide;

5-cyclopropylidene-7-(difluoromethyl)-N-(naphthalen-1-yl)-4,5-dihydropyrazolo[1,5-a]pyrimidine-3-carboxamide;

5-cyclopropylidene-N-(3,4-difluorophenyl)-7-(trifluoromethyl)-4,5-dihydropyrazolo[1,5-a]pyrimidine-3-carboxamide;

5-cyclopropylidene-N-(3,5-dichlorophenyl)-7-(difluoromethyl)-4,5-dihydropyrazolo[1,5-a]pyrimidine-3-carboxamide;

5-cyclopropylidene-7-(difluoromethyl)-N-(4-nitrophenyl)-4,5-dihydropyrazolo[1,5-a]pyrimidine-3-carboxamide;

5-cyclopropylidene-7-(difluoromethyl)-N-(2-fluorophenyl)-4,5-dihydropyrazolo[1,5-a]pyrimidine-3-carboxamide;

N-(4-bromo-2-chlorophenyl)-5-cyclopropylidene-7-(difluoromethyl)-4,5-dihydropyrazolo[1,5-a]pyrimidine-3-carboxamide;

7-methyl-5-methylene-N-(3-(3-(trifluoromethyl)phenylcarbamoyl)phenyl)-4,5-dihydropyrazolo[1,5-a]pyrimidine-3-carboxamide;

N-(4-acetamido-3-chlorophenyl)-7-methyl-5-methylene-4,5-dihydropyrazolo[1,5-a]pyrimidine-3-carboxamide;

N-(2-hydroxyphenyl)-7-methyl-5-methylene-4,5-dihydropyrazolo[1,5-a]pyrimidine-3-carboxamide;

5-cyclopropylidene-7-(difluoromethyl)-N-p-tolyl-4,5-dihydropyrazolo[1,5-a]pyrimidine-3-carboxamide;

N-(3-cyanophenyl)-5,7-dimethylpyrazolo[1,5-a]pyrimidine-3-carboxamide;
5,7-dimethyl-N-(4-(methylsulfonyl)phenyl)pyrazolo[1,5-a]pyrimidine-3-carboxamide;
N-(2-acetamidophenyl)-5,7-dimethylpyrazolo[1,5-a]pyrimidine-3-carboxamide;
N-(4-acetamidophenyl)-5,7-dimethylpyrazolo[1,5-a]pyrimidine-3-carboxamide;
5-methyl-7-phenyl-N-(2-(phenylthio)phenyl)pyrazolo[1,5-a]pyrimidine-3-carboxamide;
N-(4-ethylphenyl)-5-methyl-7,8-dihydro-6H-cyclopenta[e]pyrazolo[1,5-a]pyrimidine-3-carboxamide;
5-methyl-N-(4-(trifluoromethyl)phenyl)-7,8-dihydro-6H-cyclopenta[e]pyrazolo[1,5-a]pyrimidine-3-carboxamide;
N-(3,4-dichlorophenyl)-5-methyl-7,8-dihydro-6H-cyclopenta[e]pyrazolo[1,5-a]pyrimidine-3-carboxamide;
N-(4-ethynylphenyl)-5-methyl-7,8-dihydro-6H-cyclopenta[e]pyrazolo[1,5-a]pyrimidine-3-carboxamide;
N-(4-tert-butylcyclohexyl)-5-methyl-7,8-dihydro-6H-cyclopenta[e]pyrazolo[1,5-a]pyrimidine-3-carboxamide;
5-methyl-N-p-tolyl-6,7,8,9-tetrahydropyrazolo[1,5-a]quinazoline-3-carboxamide;
N-(4-ethylphenyl)-5-methyl-6,7,8,9-tetrahydropyrazolo[1,5-a]quinazoline-3-carboxamide;
5-methyl-N-(4-(trifluoromethyl)phenyl)-6,7,8,9-tetrahydropyrazolo[1,5-a]quinazoline-3-carboxamide;
N-(4-ethynylphenyl)-5-methyl-6,7,8,9-tetrahydropyrazolo[1,5-a]quinazoline-3-carboxamide;
N-(4-tert-butylcyclohexyl)-5-methyl-6,7,8,9-tetrahydropyrazolo[1,5-a]quinazoline-3-carboxamide;
7-(difluoromethyl)-5-methyl-N-p-tolylpyrazolo[1,5-a]pyrimidine-3-carboxamide;
7-(difluoromethyl)-5-methyl-N-(4-(trifluoromethyl)phenyl)pyrazolo[1,5-a]pyrimidine-3-carboxamide;
N-(3,4-dichlorophenyl)-7-(difluoromethyl)-5-methylpyrazolo[1,5-a]pyrimidine-3-carboxamide;
7-(difluoromethyl)-N-(4-ethynylphenyl)-5-methylpyrazolo[1,5-a]pyrimidine-3-carboxamide;
N-(4-tert-butylcyclohexyl)-5-(difluoromethyl)-7-methylpyrazolo[1,5-a]pyrimidine-3-carboxamide;
5,7-dimethyl-N-(4-(piperidin-1-yl)phenyl)pyrazolo[1,5-a]pyrimidine-3-carboxamide;
N-(3-(dimethylamino)phenyl)-5,7-dimethylpyrazolo[1,5-a]pyrimidine-3-carboxamide;
N-(4-(dimethylamino)phenyl)-5,7-dimethylpyrazolo[1,5-a]pyrimidine-3-carboxamide;
N-(4-bromophenyl)-5,7-dimethylpyrazolo[1,5-a]pyrimidine-3-carboxamide;
N-(4'-cyanobiphenyl-4-yl)-5,7-dimethylpyrazolo[1,5-a]pyrimidine-3-carboxamide;
N-(3'-methoxybiphenyl-4-yl)-5,7-dimethylpyrazolo[1,5-a]pyrimidine-3-carboxamide;
N-(3'-cyanobiphenyl-4-yl)-5,7-dimethylpyrazolo[1,5-a]pyrimidine-3-carboxamide;
N-(4'-(dimethylamino)biphenyl-4-yl)-5,7-dimethylpyrazolo[1,5-a]pyrimidine-3-carboxamide;
N-(4'-methoxybiphenyl-4-yl)-5,7-dimethylpyrazolo[1,5-a]pyrimidine-3-carboxamide;
N-(3'-(dimethylamino)biphenyl-4-yl)-5,7-dimethylpyrazolo[1,5-a]pyrimidine-3-carboxamide;
N-(4-iodophenyl)-5,7-dimethylpyrazolo[1,5-a]pyrimidine-3-carboxamide;
N-(3-bromophenyl)-5,7-dimethylpyrazolo[1,5-a]pyrimidine-3-carboxamide;
N-(4'-methoxybiphenyl-3-yl)-5,7-dimethylpyrazolo[1,5-a]pyrimidine-3-carboxamide;
N-(4'-cyanobiphenyl-3-yl)-5,7-dimethylpyrazolo[1,5-a]pyrimidine-3-carboxamide;
N-(3'-methoxybiphenyl-3-yl)-5,7-dimethylpyrazolo[1,5-a]pyrimidine-3-carboxamide;
N-(4'-(dimethylamino)biphenyl-3-yl)-5,7-dimethylpyrazolo[1,5-a]pyrimidine-3-carboxamide;
N-(3'-(dimethylamino)biphenyl-3-yl)-5,7-dimethylpyrazolo[1,5-a]pyrimidine-3-carboxamide;
5,7-dimethyl-N-(3-(pyrimidin-5-yl)phenyl)pyrazolo[1,5-a]pyrimidine-3-carboxamide;
N-(3'-cyanobiphenyl-3-yl)-5,7-dimethylpyrazolo[1,5-a]pyrimidine-3-carboxamide;
N-(4-ethylphenyl)-5-methyl-7-(4-methylpiperazin-1-yl)pyrazolo[1,5-a]pyrimidine-3-carboxamide;
N-(4-ethylphenyl)-5-methyl-7-(2-morpholinoethylamino)pyrazolo[1,5-a]pyrimidine-3-carboxamide;
N-(4-ethylphenyl)-5-methyl-7-(piperidin-1-yl)pyrazolo[1,5-a]pyrimidine-3-carboxamide;
N-(4-ethylphenyl)-5-methyl-7-morpholinopyrazolo[1,5-a]pyrimidine-3-carboxamide;
N-(4-ethylphenyl)-7-(4-isopropylpiperazin-1-yl)-5-methylpyrazolo[1,5-a]pyrimidine-3-carboxamide;
N-(4-ethylphenyl)-7-(4-isobutylpiperazin-1-yl)-5-methylpyrazolo[1,5-a]pyrimidine-3-carboxamide;
7-(4-(2-(dimethylamino)ethyl)piperazin-1-yl)-N-(4-ethylphenyl)-5-methylpyrazolo[1,5-a]pyrimidine-3-carboxamide;
7-(3,5-dimethylmorpholino)-N-(4-ethylphenyl)-5-methylpyrazolo[1,5-a]pyrimidine-3-carboxamide; or
7-(3,5-dimethylpiperazin-1-yl)-N-(4-ethylphenyl)-5-methylpyrazolo[1,5-a]pyrimidine-3-carboxamide; or a pharmaceutically acceptable salt of the compound.

12. The method of claim 11, wherein the compound is N-(4-ethynylphenyl)-5,7-dimethylpyrazolo[1,5-a]pyrimidine-3-carboxamide (NCGC00188758-01);
N-(4-ethylphenyl)-5-methyl-7-(4-methylpiperazin-1-yl)pyrazolo[1,5-a]pyrimidine-3-carboxamide (CGB2-64-1);
N-(4-ethylphenyl)-5-methyl-7-(2-morpholinoethylamino)pyrazolo[1,5-a]pyrimidine-3-carboxamide (CGB2-65-1);
((N-(4-ethylphenyl)-5-methyl-7-(piperidin-1-yl)pyrazolo[1,5-a]pyrimidine-3-carboxamide (CGB2-75-1);
N-(4-ethylphenyl)-5-methyl-7-morpholinopyrazolo[1,5-a]pyrimidine-3-carboxamide (CGB2-77-1);
N-(4-ethylphenyl)-7-(4-isopropylpiperazin-1-yl)-5-methylpyrazolo[1,5-a]pyrimidine-3-carboxamide (CGB2-79-1);
N-(4-ethylphenyl)-7-(4-isobutylpiperazin-1-yl)-5-methylpyrazolo[1,5-a]pyrimidine-3-carboxamide (CGB2-80-1);
7-(4-(2-(dimethylamino)ethyl)piperazin-1-yl)-N-(4-ethylphenyl)-5-methylpyrazolo[1,5-a]pyrimidine-3-carboxamide (CGB2-81-1);
(7-(3,5-dimethylmorpholino)-N-(4-ethylphenyl)-5-methylpyrazolo[1,5-a]pyrimidine-3-carboxamide (CGB2-82-1); or 7-(3,5-dimethylpiperazin-1-yl)-N-(4-ethylphenyl)-5-methylpyrazolo[1,5-a]pyrimidine-3-carboxamide (CGB2-83-1); or a pharmaceutically acceptable salt of the compound.

13. A method of treating or preventing the symptoms of Gaucher disease in a patient in need thereof, the method comprising providing an effective amount of a compound of Formula (I) or a pharmaceutically acceptable salt thereof to the patient, wherein Formula (I) is:

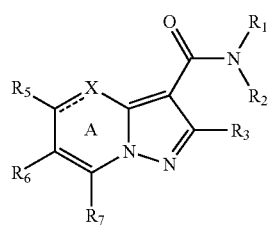

wherein the ring

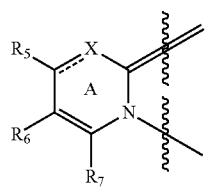

is a ring system of the formula
(i)

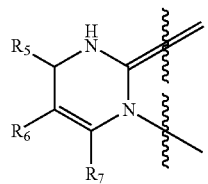

in which $R_5$ is an optionally substituted alkylidene group and $R_6$ and $R_7$ carry the definitions set forth below, or
(ii)

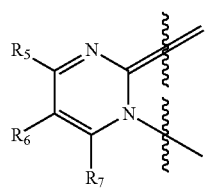

in which $R_5$, $R_6$, and $R_7$ carry the definitions set forth below;

$R_1$ is $C_1$-$C_6$alkyl, $C_2$-$C_6$alkenyl, $C_2$-$C_6$alkynyl, (mono- or bicyclic carbocycle)$C_0$-$C_4$alkyl or (mono- or bicyclic heterocycle)$C_0$-$C_4$alkyl, each of which $R_1$ is unsubstituted or substituted with one or more substituents independently chosen from halogen, hydroxyl, cyano, nitro, amino, —CHO, —COOH, $C_1$-$C_6$alkyl, $C_2$-$C_6$alkenyl, $C_2$-$C_6$alkynyl, $C_1$-$C_6$alkoxy, $C_2$-$C_6$alkanoyl, (mono- and di-$C_1$-$C_6$alkylamino)$C_0$-$C_4$alkyl, mono- and di-$C_1$-$C_6$alkylcarboxamide, $C_1$-$C_6$alkylester, $C_1$-$C_6$alkylthio, $C_1$-$C_6$alkylsulfonyl, $C_1$-$C_2$haloalkyl, and $C_1$-$C_2$haloalkoxy, and with 0 or 1 substituents chosen from Y—Z— where Z is a covalent bond, $C_1$-$C_4$alkylene, $C_2$-$C_4$alkenylene, $C_2$-$C_4$alkynylene, —S—, —O—, —NR—, —C(O)—, —NHC(O)—, or —C(O)NH—, where R is hydrogen or $C_1$-$C_4$alkyl, and Y is phenyl, pyrimidinyl, 5- or 6-membered heterocycloalkyl, or pyridyl, each of which is unsubstituted or substituted with 1 to 3 substituents independently chosen from halogen, hydroxyl, cyano, nitro, amino, $C_1$-$C_4$alkyl, $C_1$-$C_4$alkoxy, mono- or di-$C_1$-$C_4$alkylamino, trifluoromethyl, difluoromethyl, trifluoromethoxy, and phenyl; and $R_2$ is hydrogen, $C_1$-$C_6$alkyl, $C_3$-$C_7$cycloalkyl, (phenyl)$C_0$-$C_2$alkyl; or $R_1$ and $R_2$ are joined to form a 5- to 7-membered heterocycloalkyl ring having 0 or 1 additional heteroatoms chosen from N, O, and S, which 5- to 7-membered heterocycloalkyl ring is optionally fused to a phenyl or pyridyl; which 5- to 7-membered heterocycloalkyl ring is unsubstituted or substituted with one or more substituents independently chosen from halogen, hydroxyl, $C_1$-$C_2$alkyl, and $C_1$-$C_2$alkoxy;

$R_3$ is hydrogen or $C_1$-$C_2$alkyl;

$R_5$ is halogen, hydroxyl, amino, cyano, vinyl, cyclopropyl, cyclopropylidenyl, $C_1$-$C_4$alkyl, $C_1$-$C_4$alkoxy, difluoromethyl, trifluoromethyl, or phenyl;

$R_6$ is hydrogen, halogen, hydroxyl, $C_1$-$C_4$alkyl, or $C_1$-$C_4$alkoxy; and $R_7$ is halogen, hydroxyl, amino, cyano, $C_1$-$C_4$alkyl, $C_1$-$C_4$alkoxy, difluoromethyl, trifluoromethyl, or $R_7$ is phenyl or a 5- to 7-membered heterocycloalkyl ring having 1 or 2 heteroatoms chosen from N, O, and S, each of which $R_7$ is directly attached via a covalent bond or attached via a $C_1$-$C_4$ alkyl, $C_1$-$C_4$alkoxy, or $C_1$-$C_4$alkylamino group, and each of which $R_7$ is unsubstituted or substituted with 1 to 3 substituents independently chosen from halogen, hydroxyl, $C_1$-$C_4$alkyl, $C_1$-$C_4$alkoxy, (mono- and di-$C_1$-$C_2$alkylamino)$C_0$-$C_4$alkyl, $C_1$-$C_2$haloalkyl, and $C_1$-$C_2$haloalkoxy;

or $R_6$ and $R_7$ are taken together to form a 5- or 6-membered carbocyclic ring with no additional points of unsaturation, which ring is unsubstituted or substituted with 1 to 3 substituents independently chosen from $C_1$-$C_2$alkyl and $C_1$-$C_2$alkoxy.

14. The method of claim 13, wherein $R_6$ is hydrogen.

15. The method of claim 14, wherein the compound is a compound of the formula

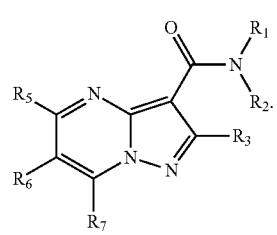

16. The method of claim 14, wherein the compound is a compound of the formula

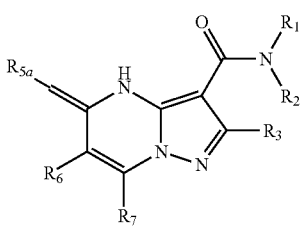

where R$_{5a}$ is hydrogen, C$_1$-C$_4$alkyl, C$_3$-C$_7$cycloalkyl, or 4- to 7-membered carbon-attached heterocycloalkyl, having 1 or 2 heteroatoms independently chosen from N, S, and O.

17. The method of claim 15, wherein
R$_2$ is hydrogen or methyl;
R$_5$ is C$_1$-C$_4$alkyl or difluoromethyl; and
R$_7$ is C$_1$-C$_4$alkyl, difluoromethyl, or phenyl.

18. The method of claim 17, wherein
R$_5$ and R$_7$ are both methyl; or
R$_5$ is methyl and R$_7$ is phenyl; or
one of R$_5$ and R$_7$ is methyl and the other is difluoromethyl.

19. The method of claim 18, wherein
R$_1$ is phenyl, cyclohexyl, naphthyl, tetrahydronaphthyl, or dihydroindenyl, each of which is unsubstituted or substituted with one or more substituents independently chosen from halogen, hydroxyl, cyano, nitro, amino, —CHO, —COOH, C$_1$-C$_6$alkyl, C$_2$-C$_6$alkanoyl, mono- or di-C$_1$-C$_6$alkylamino, mono- or di-C$_1$-C$_6$alkylcarboxamide, C$_1$-C$_6$alkylthio, C$_1$-C$_6$alkylsulfonyl, C$_1$-C$_2$haloalkyl, and C$_1$-C$_2$haloalkoxy, and with 0 or 1 substituents chosen from Y—Z— where Z is a covalent bond, C$_1$-C$_4$alkylene, —S—, —O—, —NR—, —C(O)—, —NHC(O)—, or —C(O)NH—, where R is hydrogen or C$_1$-C$_4$alkyl, and Y is phenyl or pyridyl, each of which is unsubstituted or substituted with 1 to 3 substituents independently chosen from halogen, hydroxyl, cyano, nitro, amino, C$_1$-C$_4$alkyl, and C$_1$-C$_4$alkoxy.

20. The method of claim 18, wherein
R$_1$ is phenyl, substituted with at least one substituent chosen from cyano, trifluoromethyl, and CH$_3$C(O)NH—, or
R$_1$ is cyclohexyl, substituted with at least one trifluoromethyl, or C$_3$-C$_6$alkyl; or
R$_1$ is dihydroindenyl, substituted with one or more substituents independently chosen from halogen, hydroxyl, cyano, nitro, amino, —CHO, —COOH, C$_1$-C$_4$alkyl, C$_2$-C$_4$alkanoyl, mono- or di-C$_1$-C$_4$alkylamino, C$_1$-C$_2$haloalkyl, and C$_1$-C$_2$haloalkoxy.

* * * * *